(12) United States Patent
Dixit et al.

(10) Patent No.: US 12,215,143 B2
(45) Date of Patent: Feb. 4, 2025

(54) ANTI-POLYUBIQUITIN MULTISPECIFIC ANTIBODIES

(71) Applicant: Genentech, Inc., South San Francisco, CA (US)

(72) Inventors: Vishva Dixit, Los Altos, CA (US); Marissa Matsumoto, Foster City, CA (US); Erick Castellanos, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 350 days.

(21) Appl. No.: 17/576,344

(22) Filed: Jan. 14, 2022

(65) Prior Publication Data

US 2022/0242938 A1    Aug. 4, 2022

Related U.S. Application Data

(60) Division of application No. 16/211,669, filed on Dec. 6, 2018, now Pat. No. 11,274,145, which is a continuation of application No. PCT/US2017/038940, filed on Jun. 23, 2017.

(60) Provisional application No. 62/354,305, filed on Jun. 24, 2016.

(51) Int. Cl.
    *C07K 16/18* (2006.01)
    *C12N 15/62* (2006.01)
    *G01N 33/68* (2006.01)

(52) U.S. Cl.
    CPC .............. *C07K 16/18* (2013.01); *C12N 15/62* (2013.01); *G01N 33/68* (2013.01); *G01N 33/6857* (2013.01); *C07K 2317/31* (2013.01); *C07K 2317/41* (2013.01); *C07K 2317/52* (2013.01); *C07K 2317/526* (2013.01); *C07K 2317/565* (2013.01); *C07K 2317/626* (2013.01); *G01N 2440/36* (2013.01)

(58) Field of Classification Search
    CPC ................................................. C07K 2317/31
    USPC ...................................................... 424/136.1
    See application file for complete search history.

(56) References Cited

U.S. PATENT DOCUMENTS

| | | | |
|---|---|---|---|
| 7,763,245 B2 | 7/2010 | Gordon et al. | |
| 8,133,488 B2 | 3/2012 | Kelley et al. | |
| 8,603,475 B2 | 12/2013 | Gordon et al. | |
| 8,992,919 B2 * | 3/2015 | Dixit ..................... | G01N 33/68 424/134.1 |
| 9,081,015 B2 | 7/2015 | Kelley et al. | |
| 9,321,844 B2 | 4/2016 | Kelley et al. | |
| 9,365,642 B2 | 6/2016 | Kelley et al. | |
| 9,487,578 B2 | 11/2016 | Gordon et al. | |
| 9,556,262 B2 | 1/2017 | Dixit et al. | |
| 10,035,849 B2 | 7/2018 | Kelley et al. | |
| 10,100,105 B2 | 10/2018 | Dixit et al. | |
| 10,738,106 B2 | 8/2020 | Kelley et al. | |
| 2007/0218069 A1 | 9/2007 | Gordon et al. | |
| 2009/0191209 A1 | 7/2009 | Kelley et al. | |
| 2011/0256133 A1 | 10/2011 | Dixit et al. | |
| 2013/0058955 A1 | 3/2013 | Kelley et al. | |
| 2016/0304591 A1 | 10/2016 | Kelley et al. | |
| 2019/0100578 A1 | 4/2019 | Dixit et al. | |
| 2019/0153471 A1 | 5/2019 | Paul et al. | |

FOREIGN PATENT DOCUMENTS

| | | |
|---|---|---|
| WO | 2011130499 A1 | 10/2011 |
| WO | 2013022848 A1 | 2/2013 |
| WO | 2015187428 A1 | 12/2015 |

OTHER PUBLICATIONS

U.S. Appl. No. 18/587,851, filed Feb. 2024, Matsumoto; Marissa.*
Yau et al., (Cell 171, 918-933 Nov. 2, 2017).*
Goncharov et al., Sci. Signal. 17, eabn1101 (2024) Jan. 16, 2024.*
Stolz et al.Trends Cell Biol Jan. 2018;28(1): 1-3. doi: 10.1016/j.tcb.2017.11.005. Epub Nov. 27, 2017.*
Behrends et al., "Constructing and decoding unconventional ubiquitin chains," Nat. Struct. Mol. Biol. (18)(5), pp. 520-528 (2011).
Carter, P.J., "Potent Antibody Therapeutics by Design" Nat Rev Immunol, 6, pp. 343-357 (2006).
Casset et al., "A peptide mimetic of an anti-CD4 monoclonal antibody by rational design," (BBRC 307, pp. 198-205 (2003).
Chen et al., "Selection and Analysis of an Optimized Anti-VEGF Antibody: Crystal Structure of an Affinity-matured Fab in Complex with Antigen," J. Mol. Bio. 293, pp. 865-881 (1999).
International Search Report and Written Opinion of International Application No. PCT/US2017/038940, dated Oct. 27, 2017 (18 pages).
Lamminmaki et al., "Crystal Structure of a Recombinant Anti-estradiol Fab Fragment in Complex with 17B-Estradiol," IBC 276, pp. 36687-36694 (2001).
Maccallum et al., "Antibody-antigen Interactions: Contact Analysis and Binding Site Topography," J. Mol. Biol. 262, pp. 732-745 (1996).
Matsumoto et al., "Engineering and Structural Characterization of a Linear Polybiquitin-Specific Antibody," J. Mol. Biol. 418, pp. 134-144 (2018).
Matsumoto et al., "K11-Linked Polyubiquitination in Cell Cycle Control Revealed by a K11 Linkage-Specific Antibody," Molec. Cell 39, pp. 477-484 (2010).
Milstein et al., "Hybrid Hybridomas and their use in immunohisochemistry" Nature (305(6), pp. 537-540 (1983).
Newton et al., "Ubiquitin Chain Editing Revealed by Polyubiquitin Linkage-Specific Antibodies," Cell, (134)(4), pp. 668-678, (2008).
Newton et al., "Using Linkage-Specific Monoclonal Antibodies to Analyze Cellular Ubiquitylation," Methods in Molecular Biology 832, pp. 185-196 (2012).

(Continued)

*Primary Examiner* — Lynn A Bristol
(74) *Attorney, Agent, or Firm* — McNeill PLLC

(57) ABSTRACT

The invention provides antibodies that bind mixed-topology polyubiquitin and multispecific anti-polyubiquitin antibodies, and methods of using the same.

15 Claims, 5 Drawing Sheets
Specification includes a Sequence Listing.

(56) References Cited

OTHER PUBLICATIONS

Padlan et al., "Structure of an anti-body-antigen complex: Crystal structure of the HyHEL-10 Fab-lysozyme complex," PNAS 86, pp. 5938-5942 (1989).
Pascalis et al., Grafting of "Abbreviated" Complementarity-Determining Regions Containing Specificity-Determining Residues Essential for Ligand Contact to Engineer a Less Immunogenic Humaized Monoclonal Antibody, The Journal of Immunology (169), pp. 3076-3084 (2002).
Rudikoff et al. "Single amino acid substitution altering antigen-binding specificity," PNAS USA 79, p. 1979-1983 (1982).
Vajdos et al. "Comprehensive Functional Maps of the Antigen-binding Site of an Anti-ErbB2 Antibody Obtained with Shotgun Scanning Mutagenesis," J. Mol. Biol. 320, pp. 415-428 (2002).
Wu et al., "Humanization of Murine Monoclonal Antibody by Simultaneous Optimization of Framework and CDR Residues," J. Mol. Biol. 294, pp. 151-162 (1999).
Yau et al., "Assembly and Function of Heterotypic Ubiquitin Chains in Cell-Cycle and Protein Quality Control," CellPress 171, pp. 918-933 (2017).
Zuin et al. "Ubiquitin Signaling: Extreme Conservation as a Source of Diversity," Cells 3, pp. 690-710 (2014).

\* cited by examiner

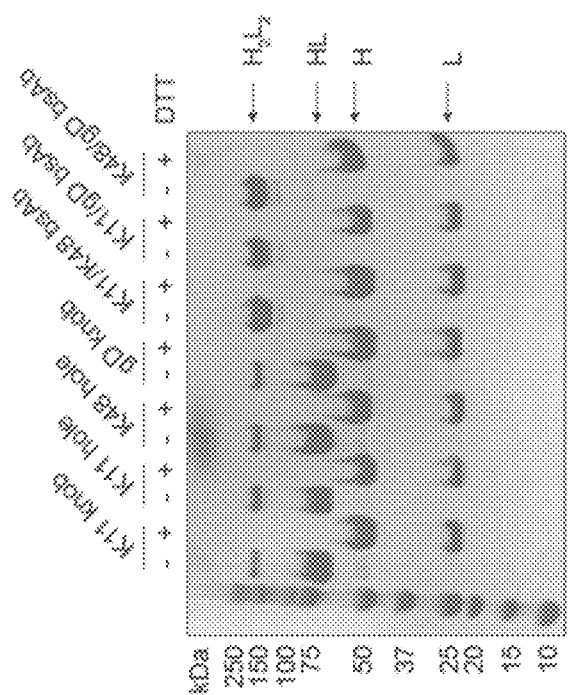
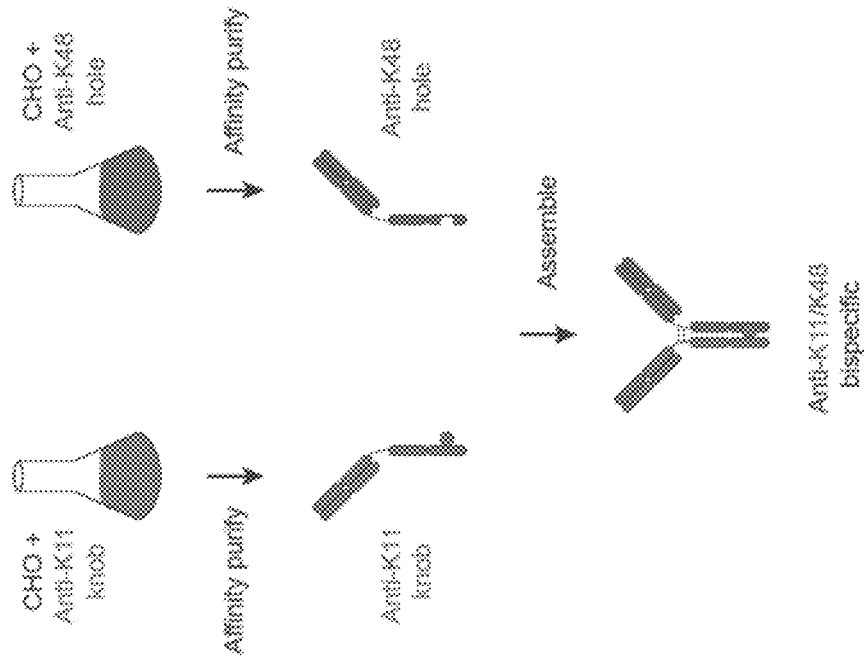
FIG. 1a-b

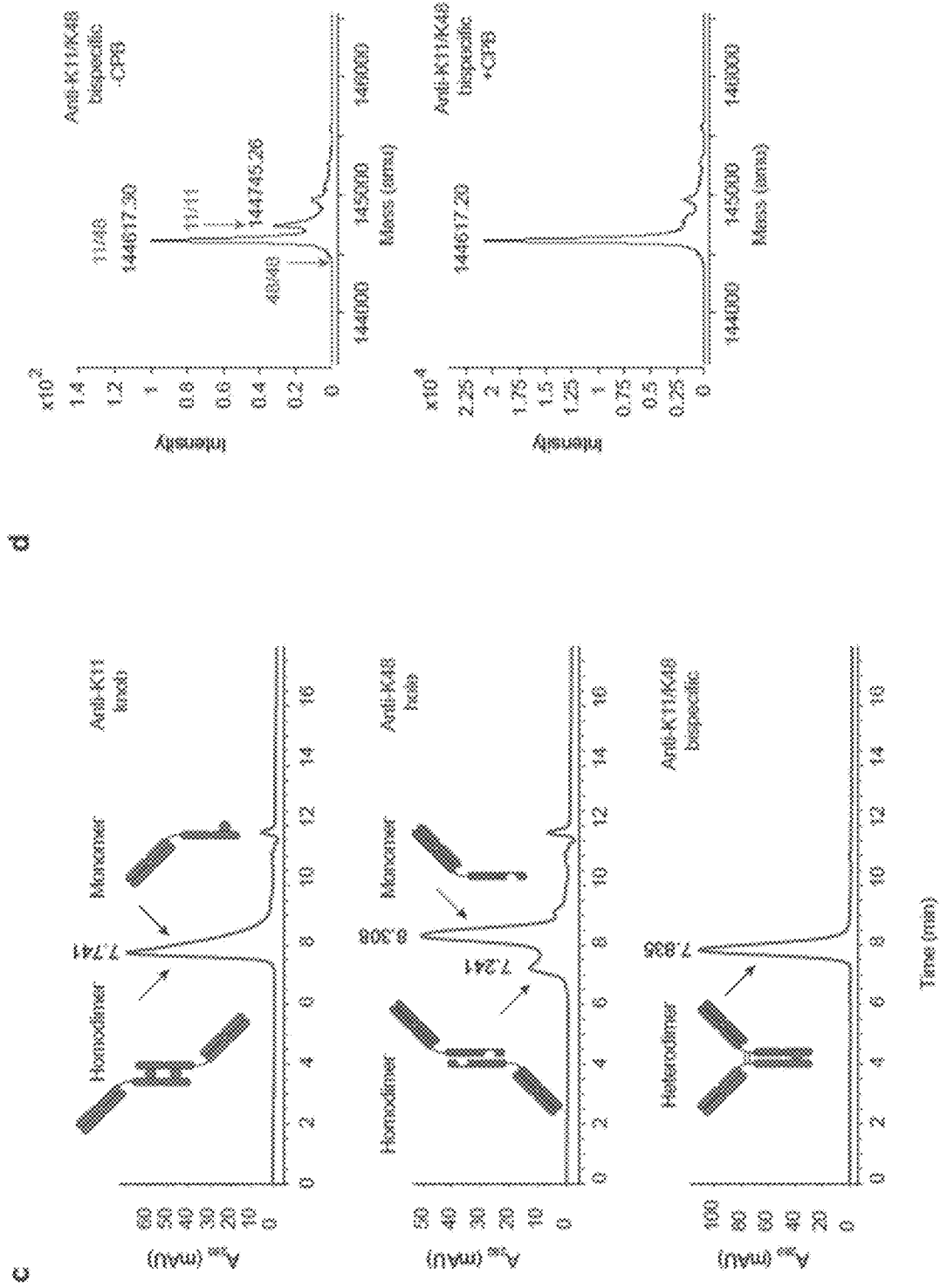
FIG. 1c-d

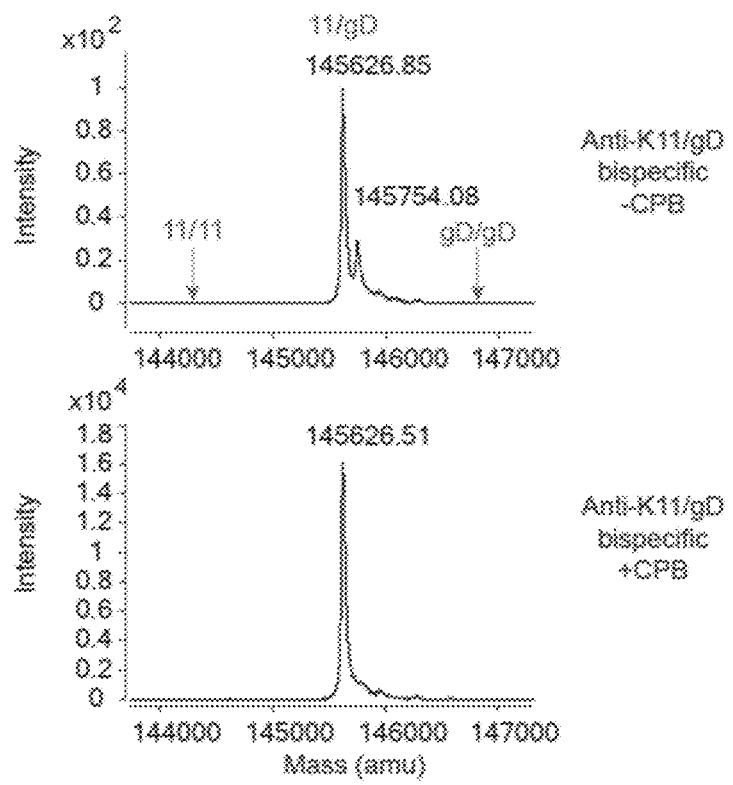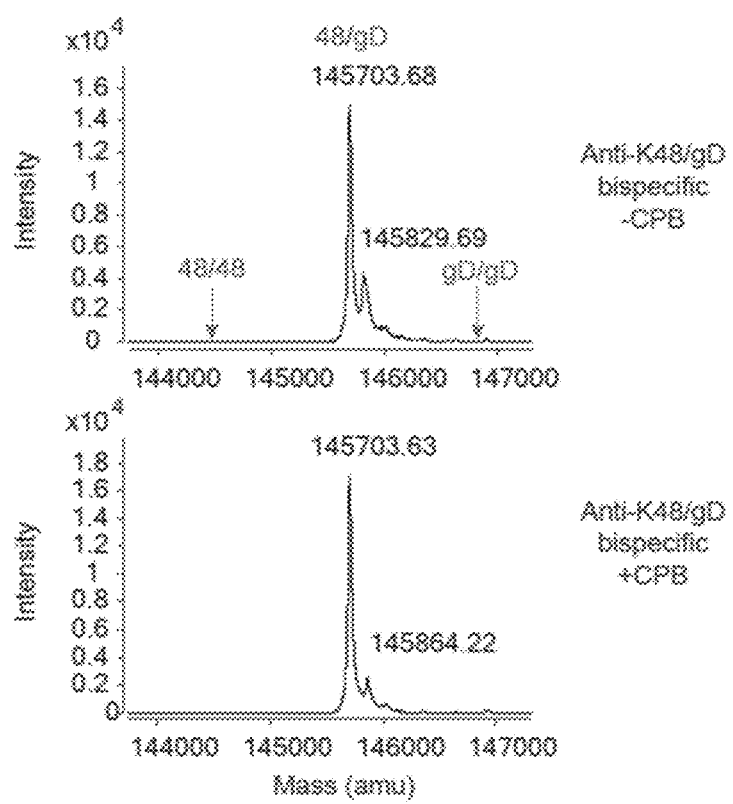
FIG. 2c

SEQUENCE LISTING

<160> NUMBER OF SEQ ID NOS: 56

<210> SEQ ID NO 1
<211> LENGTH: 233
<212> TYPE: PRT
<213> ORGANISM: Artificial Sequence
<220> FEATURE:
<223> OTHER INFORMATION: anti-K11 LC

<400> SEQUENCE: 1

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ile Val
        35                  40                  45

Gly Thr Phe Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Thr
```

```
            100                 105                 110
Thr Pro Pro Thr Phe Gly Gln Gly Thr Lys Val Glu Ile Lys Arg Thr
            115                 120                 125
Val Ala Ala Pro Ser Val Phe Ile Phe Pro Pro Ser Asp Glu Gln Leu
            130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
            195                 200                 205
Lys Val Tyr Ala Cys Glu Val Thr His Gln Gly Leu Ser Ser Pro Val
210                 215                 220
Thr Lys Ser Phe Asn Arg Gly Glu Cys
225                 230

<210> SEQ ID NO 2
<211> LENGTH: 214
<212> TYPE: PRT
<213> ORGANISM: Artificial Sequence
<220> FEATURE:
<223> OTHER INFORMATION: anti-K11 mature LC

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ile Val Gly Thr Phe
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 3
<211> LENGTH: 469
<212> TYPE: PRT
<213> ORGANISM: Artificial Sequence
<220> FEATURE:
<223> OTHER INFORMATION: anti-K11 knob HC

<400> SEQUENCE: 3

```
Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Ser Tyr Ile Ser Trp Val Arg Gln Ala Pro Gly Lys Gly Leu
    50                  55                  60

Glu Trp Val Ala Ala Ile Asn Pro Ala Gly Gly Tyr Thr Tyr Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Glu Trp Tyr Phe Gly Gly Tyr Val Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
```

```
                370                 375                 380
Val Ser Leu Trp Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys
465

<210> SEQ ID NO 4
<211> LENGTH: 450
<212> TYPE: PRT
<213> ORGANISM: Artificial Sequence
<220> FEATURE:
<223> OTHER INFORMATION: anti-K11 mature knob HC

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
                20                  25                  30

Tyr Ile Ser Trp Val Arg Gln Ala Pro Gly Lys Gly Leu Glu Trp Val
            35                  40                  45

Ala Ala Ile Asn Pro Ala Gly Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Phe Gly Tyr Val Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
                    260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Trp Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 5
<211> LENGTH: 469
<212> TYPE: PRT
<213> ORGANISM: Artificial Sequence
<220> FEATURE:
<223> OTHER INFORMATION: anti-K11 hole HC

<400> SEQUENCE: 5

Met Gly Trp Ser Cys Ile Ile Leu Phe Leu Val Ala Thr Ala Thr Gly
1               5                   10                  15
Ala Tyr Ala Glu Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Asn Ser Tyr Ile Ser Trp Val Arg Gln Ala Pro Gly Lys Gly Leu
    50                  55                  60
Glu Trp Val Ala Ala Ile Asn Pro Ala Gly Gly Tyr Thr Tyr Tyr Ala
65                  70                  75                  80
Asp Ser Val Lys Gly Arg Phe Thr Ile Ser Ala Asp Thr Ser Lys Asn
                85                  90                  95
Thr Ala Tyr Leu Gln Met Asn Ser Leu Arg Ala Glu Asp Thr Ala Val
            100                 105                 110
Tyr Tyr Cys Ala Arg Glu Trp Tyr Phe Gly Gly Tyr Val Met Asp Tyr
        115                 120                 125
Trp Gly Gln Gly Thr Leu Val Thr Val Ser Ser Ala Ser Thr Lys Gly
    130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
```

```
                165                 170                 175
Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 6
<211> LENGTH: 450
<212> TYPE: PRT
<213> ORGANISM: Artificial Sequence
<220> FEATURE:
<223> OTHER INFORMATION: anti-K11 mature hole HC

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Tyr Ile Ser Trp Val Arg Gln Ala Pro Gly Lys Gly Leu Glu Trp Val
            35                  40                  45

Ala Ala Ile Asn Pro Ala Gly Gly Tyr Thr Tyr Tyr Ala Asp Ser Val
```

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Trp Tyr Phe Gly Gly Tyr Val Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Ser Cys Ala Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
450

<210> SEQ ID NO 7
```

```
<211> LENGTH: 107
<212> TYPE: PRT
<213> ORGANISM: Artificial Sequence
<220> FEATURE:
<223> OTHER INFORMATION: anti-K11 LCVR

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Val Gly Thr Phe
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: Artificial Sequence
<220> FEATURE:
<223> OTHER INFORMATION: anti-K11 HCVR

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Tyr Ile Ser Trp Val Arg Gln Ala Pro Gly Lys Gly Leu Glu Trp Val
        35                  40                  45

Ala Ala Ile Asn Pro Ala Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Phe Gly Tyr Val Met Asp Tyr Trp Gly Gln
            100                 105                 110

Gly Thr Leu Val Thr Val Ser Ser
        115                 120

<210> SEQ ID NO 9
<211> LENGTH: 11
<212> TYPE: PRT
<213> ORGANISM: Artificial Sequence
<220> FEATURE:
<223> OTHER INFORMATION: anti-K11 HVR-L1

<400> SEQUENCE: 9

Arg Ala Ser Gln Ile Val Gly Thr Phe Val Ala
1               5                   10

<210> SEQ ID NO 10
<211> LENGTH: 7
```

```
<212> TYPE: PRT
<213> ORGANISM: Artificial Sequence
<220> FEATURE:
<223> OTHER INFORMATION: anti-K11 HVR-L2

<400> SEQUENCE: 10

Ser Ala Ser Phe Leu Tyr Ser
1               5

<210> SEQ ID NO 11
<211> LENGTH: 9
<212> TYPE: PRT
<213> ORGANISM: Artificial Sequence
<220> FEATURE:
<223> OTHER INFORMATION: anti-K11 HVR-L3

<400> SEQUENCE: 11

Gln Gln Ser Tyr Thr Thr Pro Pro Thr
1               5

<210> SEQ ID NO 12
<211> LENGTH: 10
<212> TYPE: PRT
<213> ORGANISM: Artificial Sequence
<220> FEATURE:
<223> OTHER INFORMATION: anti-K11 HVR-H1

<400> SEQUENCE: 12

Gly Phe Thr Phe Ser Asn Ser Tyr Ile Ser
1               5                   10

<210> SEQ ID NO 13
<211> LENGTH: 17
<212> TYPE: PRT
<213> ORGANISM: Artificial Sequence
<220> FEATURE:
<223> OTHER INFORMATION: anti-K11 HVR-H2

<400> SEQUENCE: 13

Ala Ile Asn Pro Ala Gly Gly Tyr Thr Tyr Tyr Ala Asp Ser Val Lys
1               5                   10                  15

Gly

<210> SEQ ID NO 14
<211> LENGTH: 13
<212> TYPE: PRT
<213> ORGANISM: Artificial Sequence
<220> FEATURE:
<223> OTHER INFORMATION: anti-K11 HVR-H3

<400> SEQUENCE: 14

Ala Arg Glu Trp Tyr Phe Gly Gly Tyr Val Met Asp Tyr
1               5                   10

<210> SEQ ID NO 15
<211> LENGTH: 234
<212> TYPE: PRT
<213> ORGANISM: Artificial Sequence
<220> FEATURE:
<223> OTHER INFORMATION: anti-K48 LC

<400> SEQUENCE: 15

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30
```

-continued

Ser Val Gly Asp Arg Val Thr Ile Thr Cys Arg Ala Ser Gln Ser Val
         35                  40                  45

Ser Ser Ala Val Ala Trp Tyr Gln Gln Lys Pro Gly Lys Ala Pro Lys
 50                  55                  60

Leu Leu Ile Tyr Ser Ala Ser Ser Leu Tyr Ser Gly Val Pro Ser Arg
 65                  70                  75                  80

Phe Ser Gly Ser Arg Ser Gly Thr Asp Phe Thr Leu Thr Ile Ser Ser
                 85                  90                  95

Leu Gln Pro Glu Asp Phe Ala Thr Tyr Tyr Cys Gln Gln Ser Ser Tyr
            100                 105                 110

Ser Ser Leu Ile Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 16
<211> LENGTH: 215
<212> TYPE: PRT
<213> ORGANISM: Artificial Sequence
<220> FEATURE:
<223> OTHER INFORMATION: anti-K48 mature LC

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Ser Leu
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

-continued

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 17
<211> LENGTH: 468
<212> TYPE: PRT
<213> ORGANISM: Artificial Sequence
<220> FEATURE:
<223> OTHER INFORMATION: anti-K48 knob HC

<400> SEQUENCE: 17

Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Ser Tyr Ser Ser Met His Trp Val Arg Gln Ala Pro Gly Lys Gly Leu
    50                  55                  60

Glu Trp Val Ala Ser Ile Tyr Ser Tyr Ser Tyr Thr Ser Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Ser Tyr Ser Tyr His Leu Gly Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 18
<211> LENGTH: 449
<212> TYPE: PRT
<213> ORGANISM: Artificial Sequence
<220> FEATURE:
<223> OTHER INFORMATION: anti-K48 mature knob HC

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Met His Trp Val Arg Gln Ala Pro Gly Lys Gly Leu Glu Trp Val
        35                  40                  45

Ala Ser Ile Tyr Ser Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Ser Tyr His Leu Gly Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Trp
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 19
<211> LENGTH: 468
<212> TYPE: PRT
<213> ORGANISM: Artificial Sequence
<220> FEATURE:
<223> OTHER INFORMATION: anti-K48 hole HC

<400> SEQUENCE: 19

Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Ser Tyr Ser Ser Met His Trp Val Arg Gln Ala Pro Gly Lys Gly Leu
    50                  55                  60

Glu Trp Val Ala Ser Ile Tyr Ser Tyr Tyr Tyr Thr Ser Tyr Ala
65                  70                  75                  80

Asp Ser Val Lys Gly Arg Phe Thr Ile Ser Ala Asp Thr Ser Lys Asn
            85                  90                  95
```

```
Thr Ala Tyr Leu Gln Met Asn Ser Leu Arg Ala Glu Asp Thr Ala Val
            100                 105                 110

Tyr Tyr Cys Ala Arg Ser Tyr Ser Tyr His Leu Gly Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Ser Cys Ala Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Val Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 20
<211> LENGTH: 449
<212> TYPE: PRT
<213> ORGANISM: Artificial Sequence
<220> FEATURE:
<223> OTHER INFORMATION: anti-K48 mature hole HC
```

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Met His Trp Val Arg Gln Ala Pro Gly Lys Gly Leu Glu Trp Val
        35                  40                  45

Ala Ser Ile Tyr Ser Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Ser Tyr Ser Tyr His Leu Gly Met Asp Tyr Trp Gly Gln Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Ser
    355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
```

-continued

```
                405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 21
<211> LENGTH: 108
<212> TYPE: PRT
<213> ORGANISM: Artificial Sequence
<220> FEATURE:
<223> OTHER INFORMATION: anti-K48 LCVR

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Ser Leu
                85                  90                  95

Ile Thr Phe Gly Gln Gly Thr Lys Val Glu Ile Lys
            100                 105
```

<210> SEQ ID NO 22
<211> LENGTH: 119
<212> TYPE: PRT
<213> ORGANISM: Artificial Sequence
<220> FEATURE:
<223> OTHER INFORMATION: anti-K48 HCVR

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Ser Met His Trp Val Arg Gln Ala Pro Gly Lys Gly Leu Glu Trp Val
        35                  40                  45

Ala Ser Ile Tyr Ser Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Ser Tyr His Leu Gly Met Asp Tyr Trp Gly Gln Gly
            100                 105                 110

Thr Leu Val Thr Val Ser Ser
        115
```

<210> SEQ ID NO 23
<211> LENGTH: 11
<212> TYPE: PRT

```
<213> ORGANISM: Artificial Sequence
<220> FEATURE:
<223> OTHER INFORMATION: anti-K48 HVR-L1

<400> SEQUENCE: 23

Arg Ala Ser Gln Ser Val Ser Ser Ala Val Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: anti-K48 HVR-L2

<400> SEQUENCE: 24

Ser Ala Ser Ser Leu Tyr Ser
1               5

<210> SEQ ID NO 25
<211> LENGTH: 10
<212> TYPE: PRT
<213> ORGANISM: Artificial Sequence
<220> FEATURE:
<223> OTHER INFORMATION: anti-K48 HVR-L3

<400> SEQUENCE: 25

Gln Gln Ser Ser Tyr Ser Ser Leu Ile Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: anti-K48 HVR-H1

<400> SEQUENCE: 26

Gly Phe Asn Ile Ser Tyr Ser Ser Met His
1               5                   10

<210> SEQ ID NO 27
<211> LENGTH: 17
<212> TYPE: PRT
<213> ORGANISM: Artificial Sequence
<220> FEATURE:
<223> OTHER INFORMATION: anti-K48 HVR-H2

<400> SEQUENCE: 27

Ser Ile Tyr Ser Tyr Tyr Ser Tyr Thr Ser Tyr Ala Asp Ser Val Lys
1               5                   10                  15
Gly

<210> SEQ ID NO 28
<211> LENGTH: 12
<212> TYPE: PRT
<213> ORGANISM: Artificial Sequence
<220> FEATURE:
<223> OTHER INFORMATION: anti-K48 HVR-H3

<400> SEQUENCE: 28

Ala Arg Ser Tyr Ser Tyr His Leu Gly Met Asp Tyr
1               5                   10

<210> SEQ ID NO 29
<211> LENGTH: 235
```

```
<212> TYPE: PRT
<213> ORGANISM: Artificial Sequence
<220> FEATURE:
<223> OTHER INFORMATION: anti-K63 LC

<400> SEQUENCE: 29

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Val
        35                  40                  45

Ser Ser Ala Val Ala Trp Tyr Gln Gln Lys Pro Gly Glu Ala Pro Lys
    50                  55                  60

Leu Leu Ile Tyr Ser Ala Arg Ser Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Ser
            100                 105                 110

Tyr Ser Ser Leu Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 30
<211> LENGTH: 216
<212> TYPE: PRT
<213> ORGANISM: Artificial Sequence
<220> FEATURE:
<223> OTHER INFORMATION: anti-K63 mature LC

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Glu Ala Pro Lys Leu Leu Ile
        35                  40                  45

Tyr Ser Ala Arg Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Ser Ser
                85                  90                  95
```

```
Leu Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 31
<211> LENGTH: 469
<212> TYPE: PRT
<213> ORGANISM: Artificial Sequence
<220> FEATURE:
<223> OTHER INFORMATION: anti-K63 knob HC

<400> SEQUENCE: 31

Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Val
        35                  40                  45

Lys Thr Gly Leu Ile His Trp Val Arg Gln Ala Pro Gly Lys Gly Leu
    50                  55                  60

Glu Trp Val Ala Tyr Ile Thr Pro Tyr Tyr Gly Ser Thr Ser Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Glu Tyr Tyr Arg Trp Tyr Thr Ala Ile Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240
```

```
Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Trp Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 32
<211> LENGTH: 450
<212> TYPE: PRT
<213> ORGANISM: Artificial Sequence
<220> FEATURE:
<223> OTHER INFORMATION: anti-K63 mature knob HC

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Lys Thr Gly
            20                  25                  30

Leu Ile His Trp Val Arg Gln Ala Pro Gly Lys Gly Leu Glu Trp Val
        35                  40                  45

Ala Tyr Ile Thr Pro Tyr Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Tyr Tyr Arg Trp Tyr Thr Ala Ile Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 33
<211> LENGTH: 469
<212> TYPE: PRT
<213> ORGANISM: Artificial Sequence
<220> FEATURE:
<223> OTHER INFORMATION: anti-K63 hole HC

<400> SEQUENCE: 33

Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30
```

-continued

Pro Gly Gly Ser Leu Arg Leu Ser Cys Ala Ala Ser Gly Phe Asn Val
            35                  40                  45

Lys Thr Gly Leu Ile His Trp Val Arg Gln Ala Pro Gly Lys Gly Leu
 50                  55                  60

Glu Trp Val Ala Tyr Ile Thr Pro Tyr Gly Ser Thr Ser Tyr Ala
 65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110

Tyr Tyr Cys Ala Arg Glu Tyr Tyr Arg Trp Tyr Thr Ala Ile Asp Tyr
                115                 120                 125

Trp Gly Gln Gly Thr Leu Val Thr Val Ser Ser Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
            370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
                420                 425                 430

Thr Val Asp Lys Ser Arg Trp Gln Gln Gly Asn Val Phe Ser Cys Ser
            435                 440                 445

```
Val Met His Glu Ala Leu His Asn His Tyr Thr Gln Lys Ser Leu Ser
    450                 455                 460

Leu Ser Pro Gly Lys
465

<210> SEQ ID NO 34
<211> LENGTH: 450
<212> TYPE: PRT
<213> ORGANISM: Artificial Sequence
<220> FEATURE:
<223> OTHER INFORMATION: anti-K63 mature hole HC

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Lys Thr Gly
            20                  25                  30

Leu Ile His Trp Val Arg Gln Ala Pro Gly Lys Gly Leu Glu Trp Val
        35                  40                  45

Ala Tyr Ile Thr Pro Tyr Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Tyr Tyr Arg Trp Tyr Thr Ala Ile Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Ser Cys Ala Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 35
<211> LENGTH: 109
<212> TYPE: PRT
<213> ORGANISM: Artificial Sequence
<220> FEATURE:
<223> OTHER INFORMATION: anti-K63 LCVR

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Glu Ala Pro Lys Leu Leu Ile
        35                  40                  45

Tyr Ser Ala Arg Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Ser Ser
                85                  90                  95

Leu Phe Thr Phe Gly Gln Gly Thr Lys Val Glu Ile Lys
            100                 105

<210> SEQ ID NO 36
<211> LENGTH: 120
<212> TYPE: PRT
<213> ORGANISM: Artificial Sequence
<220> FEATURE:
<223> OTHER INFORMATION: anti-K63 HCVR

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Lys Thr Gly
            20                  25                  30

Leu Ile His Trp Val Arg Gln Ala Pro Gly Lys Gly Leu Glu Trp Val
        35                  40                  45

Ala Tyr Ile Thr Pro Tyr Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
            85                  90                  95

Ala Arg Glu Tyr Tyr Arg Trp Tyr Thr Ala Ile Asp Tyr Trp Gly Gln
        100                 105                 110

Gly Thr Leu Val Thr Val Ser Ser
        115                 120

<210> SEQ ID NO 37
<211> LENGTH: 11
<212> TYPE: PRT
<213> ORGANISM: Artificial Sequence
<220> FEATURE:
<223> OTHER INFORMATION: anti-K63 HVR-L1

<400> SEQUENCE: 37

Arg Ala Ser Gln Ser Val Ser Ser Ala Val Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: anti-K63 HVR-L2

<400> SEQUENCE: 38

Ser Ala Arg Ser Leu Tyr Ser
1               5

<210> SEQ ID NO 39
<211> LENGTH: 11
<212> TYPE: PRT
<213> ORGANISM: Artificial Sequence
<220> FEATURE:
<223> OTHER INFORMATION: anti-K63 HVR-L3

<400> SEQUENCE: 39

Gln Gln Tyr Ser Ser Tyr Ser Ser Leu Phe Thr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: anti-K63 HVR-H1

<400> SEQUENCE: 40

Gly Phe Asn Val Lys Thr Gly Leu Ile His
1               5                   10

<210> SEQ ID NO 41
<211> LENGTH: 17
<212> TYPE: PRT
<213> ORGANISM: Artificial Sequence
<220> FEATURE:
<223> OTHER INFORMATION: anti-K63 HVR-H2

<400> SEQUENCE: 41

Tyr Ile Thr Pro Tyr Tyr Gly Ser Thr Ser Tyr Ala Asp Ser Val Lys
1               5                   10                  15

Gly

<210> SEQ ID NO 42

```
<211> LENGTH: 13
<212> TYPE: PRT
<213> ORGANISM: Artificial Sequence
<220> FEATURE:
<223> OTHER INFORMATION: anti-K63 HVR-H3

<400> SEQUENCE: 42

Ala Arg Glu Tyr Tyr Arg Trp Tyr Thr Ala Ile Asp Tyr
1               5                   10

<210> SEQ ID NO 43
<211> LENGTH: 233
<212> TYPE: PRT
<213> ORGANISM: Artificial Sequence
<220> FEATURE:
<223> OTHER INFORMATION: anti-linear LC

<400> SEQUENCE: 43

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Ser Thr Ala Val Ala Trp Tyr Gln Gln Lys Pro Gly Lys Ala Pro Lys
    50                  55                  60

Leu Leu Ile Tyr Ser Ala Lys Phe Leu Tyr Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 44
<211> LENGTH: 214
<212> TYPE: PRT
<213> ORGANISM: Artificial Sequence
<220> FEATURE:
<223> OTHER INFORMATION: anti-linear mature LC

<400> SEQUENCE: 44

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Lys Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 468
<212> TYPE: PRT
<213> ORGANISM: Artificial Sequence
<220> FEATURE:
<223> OTHER INFORMATION: anti-linear knob HC

<400> SEQUENCE: 45

Met Gly Trp Ser Cys Ile Ile Leu Phe Leu Val Ala Thr Ala Thr Gly
1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Thr Tyr Ile Ser Trp Val Arg Gln Ala Pro Gly Lys Gly Leu
    50                  55                  60

Glu Trp Val Ala Ser Ile Thr Pro Ser Ser Gly Gln Thr Asp Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Thr Trp Leu Leu Arg Trp Val Met Asp Leu Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 46
<211> LENGTH: 449
<212> TYPE: PRT
<213> ORGANISM: Artificial Sequence
<220> FEATURE:
<223> OTHER INFORMATION: anti-linear mature knob HC

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Tyr Ile Ser Trp Val Arg Gln Ala Pro Gly Lys Gly Leu Glu Trp Val
        35                  40                  45

```
Ala Ser Ile Thr Pro Ser Ser Gly Gln Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Trp Leu Leu Arg Trp Val Met Asp Leu Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 47
```

```
<211> LENGTH: 468
<212> TYPE: PRT
<213> ORGANISM: Artificial Sequence
<220> FEATURE:
<223> OTHER INFORMATION: anti-linear hole HC

<400> SEQUENCE: 47
```

| | | | | | | | | | | | | | | | |
|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| 1 | | | | 5 | | | | | 10 | | | | | 15 | |
| Ala | Tyr | Ala | Glu | Val | Gln | Leu | Val | Glu | Ser | Gly | Gly | Gly | Leu | Val | Gln |
| | | | 20 | | | | | 25 | | | | | 30 | | |
| Pro | Gly | Gly | Ser | Leu | Arg | Leu | Ser | Cys | Ala | Ala | Ser | Gly | Phe | Thr | Phe |
| | | 35 | | | | | 40 | | | | | 45 | | | |
| Ser | Asn | Thr | Tyr | Ile | Ser | Trp | Val | Arg | Gln | Ala | Pro | Gly | Lys | Gly | Leu |
| | 50 | | | | | 55 | | | | | 60 | | | | |
| Glu | Trp | Val | Ala | Ser | Ile | Thr | Pro | Ser | Ser | Gly | Gln | Thr | Asp | Tyr | Ala |
| 65 | | | | | 70 | | | | | 75 | | | | | 80 |
| Asp | Ser | Val | Lys | Gly | Arg | Phe | Thr | Ile | Ser | Ala | Asp | Thr | Ser | Lys | Asn |
| | | | | 85 | | | | | 90 | | | | | 95 | |
| Thr | Ala | Tyr | Leu | Gln | Met | Asn | Ser | Leu | Arg | Ala | Glu | Asp | Thr | Ala | Val |
| | | | 100 | | | | | 105 | | | | | 110 | | |
| Tyr | Tyr | Cys | Ala | Arg | Thr | Trp | Leu | Leu | Arg | Trp | Val | Met | Asp | Leu | Trp |
| | | 115 | | | | | 120 | | | | | 125 | | | |
| Gly | Gln | Gly | Thr | Leu | Val | Thr | Val | Ser | Ser | Ala | Ser | Thr | Lys | Gly | Pro |
| | 130 | | | | | 135 | | | | | 140 | | | | |
| Ser | Val | Phe | Pro | Leu | Ala | Pro | Ser | Ser | Lys | Ser | Thr | Ser | Gly | Gly | Thr |
| 145 | | | | | 150 | | | | | 155 | | | | | 160 |
| Ala | Ala | Leu | Gly | Cys | Leu | Val | Lys | Asp | Tyr | Phe | Pro | Glu | Pro | Val | Thr |
| | | | | 165 | | | | | 170 | | | | | 175 | |
| Val | Ser | Trp | Asn | Ser | Gly | Ala | Leu | Thr | Ser | Gly | Val | His | Thr | Phe | Pro |
| | | | 180 | | | | | 185 | | | | | 190 | | |
| Ala | Val | Leu | Gln | Ser | Ser | Gly | Leu | Tyr | Ser | Leu | Ser | Ser | Val | Val | Thr |
| | | | 195 | | | | | 200 | | | | | 205 | | |
| Val | Pro | Ser | Ser | Ser | Leu | Gly | Thr | Gln | Thr | Tyr | Ile | Cys | Asn | Val | Asn |
| | 210 | | | | | 215 | | | | | 220 | | | | |
| His | Lys | Pro | Ser | Asn | Thr | Lys | Val | Asp | Lys | Lys | Val | Glu | Pro | Lys | Ser |
| 225 | | | | | 230 | | | | | 235 | | | | | 240 |
| Cys | Asp | Lys | Thr | His | Thr | Cys | Pro | Pro | Cys | Pro | Ala | Pro | Glu | Leu | Leu |
| | | | | 245 | | | | | 250 | | | | | 255 | |
| Gly | Gly | Pro | Ser | Val | Phe | Leu | Phe | Pro | Pro | Lys | Pro | Lys | Asp | Thr | Leu |
| | | | 260 | | | | | 265 | | | | | 270 | | |
| Met | Ile | Ser | Arg | Thr | Pro | Glu | Val | Thr | Cys | Val | Val | Val | Asp | Val | Ser |
| | | 275 | | | | | 280 | | | | | 285 | | | |
| His | Glu | Asp | Pro | Glu | Val | Lys | Phe | Asn | Trp | Tyr | Val | Asp | Gly | Val | Glu |
| | 290 | | | | | 295 | | | | | 300 | | | | |
| Val | His | Asn | Ala | Lys | Thr | Lys | Pro | Arg | Glu | Glu | Gln | Tyr | Asn | Ser | Thr |
| 305 | | | | | 310 | | | | | 315 | | | | | 320 |
| Tyr | Arg | Val | Val | Ser | Val | Leu | Thr | Val | Leu | His | Gln | Asp | Trp | Leu | Asn |
| | | | | 325 | | | | | 330 | | | | | 335 | |
| Gly | Lys | Glu | Tyr | Lys | Cys | Lys | Val | Ser | Asn | Lys | Ala | Leu | Pro | Ala | Pro |
| | | | 340 | | | | | 345 | | | | | 350 | | |
| Ile | Glu | Lys | Thr | Ile | Ser | Lys | Ala | Lys | Gly | Gln | Pro | Arg | Glu | Pro | Gln |
| | | | 355 | | | | | 360 | | | | | 365 | | |
| Val | Tyr | Thr | Leu | Pro | Pro | Ser | Arg | Glu | Glu | Met | Thr | Lys | Asn | Gln | Val |
| | 370 | | | | | 375 | | | | | 380 | | | | |

```
Ser Leu Ser Cys Ala Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Val Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 48
<211> LENGTH: 449
<212> TYPE: PRT
<213> ORGANISM: Artificial Sequence
<220> FEATURE:
<223> OTHER INFORMATION: anti-linear mature hole HC

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Tyr Ile Ser Trp Val Arg Gln Ala Pro Gly Lys Gly Leu Glu Trp Val
        35                  40                  45

Ala Ser Ile Thr Pro Ser Ser Gly Gln Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Trp Leu Leu Arg Trp Val Met Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 49
<211> LENGTH: 107
<212> TYPE: PRT
<213> ORGANISM: Artificial Sequence
<220> FEATURE:
<223> OTHER INFORMATION: anti-linear LCVR

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Lys Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 50
<211> LENGTH: 119
<212> TYPE: PRT
<213> ORGANISM: Artificial Sequence
<220> FEATURE:
<223> OTHER INFORMATION: anti-linear HCVR

<400> SEQUENCE: 50

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Thr
            20                  25                  30

Tyr Ile Ser Trp Val Arg Gln Ala Pro Gly Lys Gly Leu Glu Trp Val
        35                  40                  45

Ala Ser Ile Thr Pro Ser Gly Gln Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Trp Leu Leu Arg Trp Val Met Asp Leu Trp Gly Gln Gly
            100                 105                 110

Thr Leu Val Thr Val Ser Ser
        115
```

```
<210> SEQ ID NO 51
<211> LENGTH: 11
<212> TYPE: PRT
<213> ORGANISM: Artificial Sequence
<220> FEATURE:
<223> OTHER INFORMATION: anti-linear HVR-L1

<400> SEQUENCE: 51

Arg Ala Ser Gln Asp Val Ser Thr Ala Val Ala
1               5                   10

<210> SEQ ID NO 52
<211> LENGTH: 7
<212> TYPE: PRT
<213> ORGANISM: Artificial Sequence
<220> FEATURE:
<223> OTHER INFORMATION: anti-linear HVR-L2

<400> SEQUENCE: 52

Ser Ala Lys Phe Leu Tyr Ser
1               5

<210> SEQ ID NO 53
<211> LENGTH: 9
<212> TYPE: PRT
<213> ORGANISM: Artificial Sequence
<220> FEATURE:
<223> OTHER INFORMATION: anti-linear HVR-L3

<400> SEQUENCE: 53

Gln Gln Ser Tyr Thr Thr Pro Pro Thr
1               5

<210> SEQ ID NO 54
<211> LENGTH: 10
<212> TYPE: PRT
<213> ORGANISM: Artificial Sequence
<220> FEATURE:
<223> OTHER INFORMATION: anti-linear HVR-H1

<400> SEQUENCE: 54

Gly Phe Thr Phe Ser Asn Thr Tyr Ile Ser
1               5                   10

<210> SEQ ID NO 55
<211> LENGTH: 17
<212> TYPE: PRT
<213> ORGANISM: Artificial Sequence
```

```
<220> FEATURE:
<223> OTHER INFORMATION: anti-linear HVR-H2

<400> SEQUENCE: 55

Ser Ile Thr Pro Ser Ser Gly Gln Thr Asp Tyr Ala Asp Ser Val Lys
1               5                   10                  15
Gly

<210> SEQ ID NO 56
<211> LENGTH: 12
<212> TYPE: PRT
<213> ORGANISM: Artificial Sequence
<220> FEATURE:
<223> OTHER INFORMATION: anti-linear HVR-H3

<400> SEQUENCE: 56

Ala Arg Thr Trp Leu Leu Arg Trp Val Met Asp Leu
1               5                   10
```

ANTI-POLYUBIQUITIN MULTISPECIFIC ANTIBODIES

CROSS-REFERENCE TO RELATED APPLICATIONS

This application is a divisional of U.S. application Ser. No. 16/211,669 filed Dec. 6, 2018, which is a continuation of International Application No. PCT/US2017/038940 filed Jun. 23, 2017, which claims the benefit of priority of U.S. Provisional Application No. 62/354,305, filed Jun. 24, 2016, all of which are incorporated by reference herein in their entirety for any purpose.

FIELD OF THE INVENTION

The present invention relates to anti-polyubiquitin multispecific antibodies and methods of making and using the same.

INTRODUCTION AND SUMMARY

Ubiquitin is a small protein that has important regulatory roles in a wide variety of cellular pathways. The best known of these is ubiquitin's role in protein degradation, where covalent attachment of ubiquitin to a target protein enables that targeted protein to be recognized and destroyed by the 26S proteasome (see Wilkinson, *Semin. Cell Devel. Biol.* 11(3): 141-148 (2000)). The covalent attachment of ubiquitin, a 76 amino acid protein, to a target protein is a three-step enzymatic process (Pickart, *Annu. Rev. Biochem.* 70: 503-533 (2001)). First, ubiquitin-activating enzyme E1 forms an ubiquitin-E1 thioester in an ATP-dependent reaction. The ubiquitin is transferred from the ubiquitin-E1 thioester to a member of the ubiquitin-conjugating enzyme (E2) family in the second step. In the third step, with the assistance of a ubiquitin-protein ligase (E3), an isopeptide bond is formed between the carboxyl terminus of ubiquitin and the ε-amino group of a lysine residue on the target protein. Enzymes termed deubiquitinases remove ubiquitin moieties from target proteins (Guterman and Glickman, *Curr. Prot. Pep. Sci.* 5: 201-210 (2004)).

Ubiquitin contains seven lysine residues (Lys6, Lys11, Lys27, Lys33, Lys29, Lys48, and Lys63), and thus ubiquitin itself may serve as a target protein for ubiquitination (Peng et al., *Nat. Biotechnol.* 21: 921-926 (2003); Pickart and Fushman, *Curr. Opin. Chem. Biol.* 8:610-616 (2004)). The molecule produced upon ubiquitination of a ubiquitin protein is termed a polyubiquitin molecule, and may comprise two or more ubiquitin moieties. Ubiquitination of ubiquitin may theoretically occur at any of the seven lysine residues (Peng et al., *Nat. Biotechnol.* 21: 921-926 (2003)), so that different species of polyubiquitins exist having isopeptide bonds to different lysine residues within ubiquitin. Polyubiquitin chains with internal isopeptide linkages at all seven lysine residues have been reported. Iwai and Tokunaga, *EMBO Reports* 10:706-713 (2009).

Additionally, linear polyubiquitin linkages form in which the C-terminal glycine of ubiquitin is conjugated to the α-amino group of the N-terminal methionine of another ubiquitin molecule. Iwai and Tokunaga, *EMBO Reports* 10:706-713 (2009). Linear polyubiquitin is formed via the linear ubiquitin chain assembly complex (LUBAC) which is composed of two ring finger proteins, HOIL-1L and HOIP. Tokunaga et al., *Nat. Cell Biol.* 11:123-132 (2009). It is believed that genetically encoded, unanchored linear polyubiquitin does not exist in cells as its C-terminus is vulnerable to cleavage by isopeptidase T. Iwai and Tokunaga, *EMBO Reports* 10:706-713 (2009). This observation suggests that linear polyubiquitin is assembled onto a substrate protein post-translationally and that conjugated linear polyubiquitin molecules are potential modulators of protein activity and function. Id. For example, linear polyubiquitination of the NF-κB essential modulator (NEMO) has been shown to play a role in NF-κB activation. Id.

Polyubiquitin chains comprising two or more Ub to Ub linkages (three or more ubiquitin monomers) can have homogeneous or mixed topology. A chain is homogenous if the same residue is modified during the successive steps of elongation, as in the case of uniformly linear (or Met1-), Lys11-, Lys48-, or Lys63-linked chains, while a chain has mixed topology if there are different linkages at different positions in the chain. Komander and Rape, *Annu. Rev. Biochem.* 81:203-29 (2012). A mixed chain may be (but is not necessarily) branched, wherein the same monomer has at least three different linkages (such as linkages to three other ubiquitin monomers, or a linkage to a substrate polypeptide and linkages to two other ubiquitin monomers). Id. Mixed topology chains have been reported in the contexts of NF-κB signaling and protein trafficking. Id.; see also Refs. 7-10 therein. Additionally, the same protein can be polyubiquitinated at two or more positions with at least first and second polyubiquitins, with the first and second polyubiquitins having different linkages.

The traditional method for determining linkages of trypsin digest and LC-MS/MS is not believed to be feasible with branched chains. Cleavage by trypsin after additional lysine and arginine residues between K11 and K48 in the primary sequence of ubiquitin prevents identification of the modified K11 and K48 within a single peptide.

Indirect approaches for detecting branched polyubiquitin chains have been described. In order to demonstrate the existence of branched chains, a combination of K11R and K48R ubiquitin mutants and an engineered ubiquitin containing an inserted TEV cleavage site were used as well as chimeric E2 enzymes to reprogram the specificity of linkages synthesized by the anaphase-promoting complex/cyclosome. See Meyer, H. J. & Rape, M. *Cell* 157, 910-921 (2014).

Multispecific antibodies that bind mixed-topology polyubiquitin and/or have specificity for different polyubiquitin linkages could provide benefits such as simplifying the detection of mixed-topology polyubiquitin chains or proteins polyubiquitinated with polyubiquitins having different linkages, facilitating further examination of the role of such chains in protein degradation and regulation, targeting and modulating mixed-topology polyubiquitin in pathways that involve it, or at least a useful choice.

Provided herein are multispecific anti-polyubiquitin antibodies and immunoconjugates and methods of using the same. The antibodies can be useful for detection procedures such as immunohistochemistry, Western blotting, immunoprecipitation, ELISA, etc., and functional assays.

Provided herein is an antibody with a greater avidity for a mixed-topology polyubiquitin than a single-topology polyubiquitin, wherein the mixed-topology polyubiquitin comprises a first linkage and a second linkage, wherein the first linkage and the second linkage differ from one another. Also provided herein is a multispecific antibody that binds a mixed-topology polyubiquitin comprising a first linkage and a second linkage, the antibody comprising a first antigen recognition site specific for the first linkage, and a second antigen recognition site specific for the second linkage, wherein the first linkage and the second linkage differ from one another.

In some embodiments, an antibody provided herein comprises a first VH/VL unit specific for the first linkage, and a second VH/VL unit specific for the second linkage. In some embodiments, the antibody is a knob-in-hole bispecific antibody; a bispecific antibody comprising a leucine zipper; a cross-linked pair of antibodies; an antibody Fc-heterodimeric molecule; a diabody; a triabody; a tetrabody; a single-chain Fv dimer; a trispecific antibody; an octopus antibody; or a dual acting FAb.

In some embodiments, the first linkage or the second linkage is a K11 linkage.
the first linkage or the second linkage is a K48 linkage.
the first linkage or the second linkage is a K63-linkage.
the first linkage or the second linkage is a C-terminal to N-terminal-linkage.
the first linkage and the second linkage are: a K11 linkage and a K48 linkage; a K11 linkage and a K63 linkage; a K11 linkage and a C- to N-terminal linkage; a K48 linkage and a K63 linkage; a K48 linkage and a C- to N-terminal linkage; or a K63 linkage and a C- to N-terminal linkage.

In some embodiments, the antibody comprises a first half antibody that comprises: a) (i) HVR-L1 comprising the amino acid sequence of SEQ ID NO: 9, (ii) HVR-L2 comprising the amino acid sequence of SEQ ID NO: 10, (iii) HVR-L3 comprising the amino acid sequence of SEQ ID NO: 11, (iv) HVR-H1 comprising the amino acid sequence of SEQ ID NO: 12, (v) HVR-H2 comprising the amino acid sequence of SEQ ID NO: 13, and (vi) HVR-H3 comprising the amino acid sequence of SEQ ID NO: 14; b) (i) HVR-L1 comprising the amino acid sequence of SEQ ID NO: 23, (ii) HVR-L2 comprising the amino acid sequence of SEQ ID NO: 24, (iii) HVR-L3 comprising the amino acid sequence of SEQ ID NO: 25, (iv) HVR-H1 comprising the amino acid sequence of SEQ ID NO: 26, (v) HVR-H2 comprising the amino acid sequence of SEQ ID NO: 27, and (vi) HVR-H3 comprising the amino acid sequence of SEQ ID NO: 28; c) (i) HVR-L1 comprising the amino acid sequence of SEQ ID NO: 37, (ii) HVR-L2 comprising the amino acid sequence of SEQ ID NO: 38, (iii) HVR-L3 comprising the amino acid sequence of SEQ ID NO: 39, (iv) HVR-H1 comprising the amino acid sequence of SEQ ID NO: 40, (v) HVR-H2 comprising the amino acid sequence of SEQ ID NO: 41, and (vi) HVR-H3 comprising the amino acid sequence of SEQ ID NO: 42; or d) (i) HVR-L1 comprising the amino acid sequence of SEQ ID NO: 51, (ii) HVR-L2 comprising the amino acid sequence of SEQ ID NO: 52, (iii) HVR-L3 comprising the amino acid sequence of SEQ ID NO: 53, (iv) HVR-H1 comprising the amino acid sequence of SEQ ID NO: 54, (v) HVR-H2 comprising the amino acid sequence of SEQ ID NO: 55, and (vi) HVR-H3 comprising the amino acid sequence of SEQ ID NO: 56.

In some embodiments, the antibody comprises a second half antibody that comprises: a) (i) HVR-L1 comprising the amino acid sequence of SEQ ID NO: 9, (ii) HVR-L2 comprising the amino acid sequence of SEQ ID NO: 10, (iii) HVR-L3 comprising the amino acid sequence of SEQ ID NO: 11, (iv) HVR-H1 comprising the amino acid sequence of SEQ ID NO: 12, (v) HVR-H2 comprising the amino acid sequence of SEQ ID NO: 13, and (vi) HVR-H3 comprising the amino acid sequence of SEQ ID NO: 14; b) (i) HVR-L1 comprising the amino acid sequence of SEQ ID NO: 23, (ii) HVR-L2 comprising the amino acid sequence of SEQ ID NO: 24, (iii) HVR-L3 comprising the amino acid sequence of SEQ ID NO: 25, (iv) HVR-H1 comprising the amino acid sequence of SEQ ID NO: 26, (v) HVR-H2 comprising the amino acid sequence of SEQ ID NO: 27, and (vi) HVR-H3 comprising the amino acid sequence of SEQ ID NO: 28; c) (i) HVR-L1 comprising the amino acid sequence of SEQ ID NO: 37, (ii) HVR-L2 comprising the amino acid sequence of SEQ ID NO: 38, (iii) HVR-L3 comprising the amino acid sequence of SEQ ID NO: 39, (iv) HVR-H1 comprising the amino acid sequence of SEQ ID NO: 40, (v) HVR-H2 comprising the amino acid sequence of SEQ ID NO: 41, and (vi) HVR-H3 comprising the amino acid sequence of SEQ ID NO: 42; or d) (i) HVR-L1 comprising the amino acid sequence of SEQ ID NO: 51, (ii) HVR-L2 comprising the amino acid sequence of SEQ ID NO: 52, (iii) HVR-L3 comprising the amino acid sequence of SEQ ID NO: 53, (iv) HVR-H1 comprising the amino acid sequence of SEQ ID NO: 54, (v) HVR-H2 comprising the amino acid sequence of SEQ ID NO: 55, and (vi) HVR-H3 comprising the amino acid sequence of SEQ ID NO: 56, wherein the HVRs of the second half antibody are not identical to the HVRs of the first half antibody.

In some embodiments, the antibody comprises first and second half antibodies, wherein: a) one of the first and second half antibodies comprises (i) HVR-L1 comprising the amino acid sequence of SEQ ID NO: 9, (ii) HVR-L2 comprising the amino acid sequence of SEQ ID NO: 10, (iii) HVR-L3 comprising the amino acid sequence of SEQ ID NO: 11, (iv) HVR-H1 comprising the amino acid sequence of SEQ ID NO: 12, (v) HVR-H2 comprising the amino acid sequence of SEQ ID NO: 13, and (vi) HVR-H3 comprising the amino acid sequence of SEQ ID NO: 14, and the other of the first and second half antibodies comprises (i) HVR-L1 comprising the amino acid sequence of SEQ ID NO: 23, (ii) HVR-L2 comprising the amino acid sequence of SEQ ID NO: 24, (iii) HVR-L3 comprising the amino acid sequence of SEQ ID NO: 25, (iv) HVR-H1 comprising the amino acid sequence of SEQ ID NO: 26, (v) HVR-H2 comprising the amino acid sequence of SEQ ID NO: 27, and (vi) HVR-H3 comprising the amino acid sequence of SEQ ID NO: 28; b) one of the first and second half antibodies comprises (i) HVR-L1 comprising the amino acid sequence of SEQ ID NO: 9, (ii) HVR-L2 comprising the amino acid sequence of SEQ ID NO: 10, (iii) HVR-L3 comprising the amino acid sequence of SEQ ID NO: 11, (iv) HVR-H1 comprising the amino acid sequence of SEQ ID NO: 12, (v) HVR-H2 comprising the amino acid sequence of SEQ ID NO: 13, and (vi) HVR-H3 comprising the amino acid sequence of SEQ ID NO: 14, and the other of the first and second half antibodies comprises (i) HVR-L1 comprising the amino acid sequence of SEQ ID NO: 37, (ii) HVR-L2 comprising the amino acid sequence of SEQ ID NO: 38, (iii) HVR-L3 comprising the amino acid sequence of SEQ ID NO: 39, (iv) HVR-H1 comprising the amino acid sequence of SEQ ID NO: 40, (v) HVR-H2 comprising the amino acid sequence of SEQ ID NO: 41, and (vi) HVR-H3 comprising the amino acid sequence of SEQ ID NO: 42; c) one of the first and second half antibodies comprises (i) HVR-L1 comprising the amino acid sequence of SEQ ID NO: 9, (ii) HVR-L2 comprising the amino acid sequence of SEQ ID NO: 10, (iii) HVR-L3 comprising the amino acid sequence of SEQ ID NO: 11, (iv) HVR-H1 comprising the amino acid sequence of SEQ ID NO: 12, (v) HVR-H2 comprising the amino acid sequence of SEQ ID NO: 13, and (vi) HVR-H3 comprising the amino acid sequence of SEQ ID NO: 14, and the other of the first and second half antibodies comprises (i) HVR-L1 comprising the amino acid sequence of SEQ ID NO: 51, (ii) HVR-L2 comprising the amino acid sequence of SEQ ID NO: 52, (iii) HVR-L3 comprising the amino acid sequence of SEQ ID NO: 53, (iv) HVR-H1 comprising the amino acid sequence of SEQ ID NO: 54, (v) HVR-H2 comprising the amino acid sequence of SEQ ID NO: 55, and (vi) HVR-H3 comprising the amino acid sequence of SEQ ID NO: 56; d) one of the first and second half antibodies comprises (i) HVR-L1 comprising the amino acid sequence of SEQ ID NO: 23, (ii) HVR-L2 comprising the amino acid sequence of SEQ ID NO: 24, (iii) HVR-L3 comprising the amino acid sequence of SEQ ID NO: 25, (iv) HVR-H1 comprising the amino acid sequence of SEQ ID NO: 26, (v) HVR-H2 comprising the amino acid sequence of SEQ ID NO: 27, and (vi) HVR-H3 comprising the amino acid sequence of SEQ ID NO: 28, and the other of the first and second half antibodies comprises (i) HVR-L1 comprising the amino acid sequence of SEQ ID NO: 37, (ii) HVR-L2 comprising the amino acid sequence of SEQ ID NO: 38, (iii) HVR-L3 comprising the amino acid sequence of SEQ ID NO: 39, (iv) HVR-H1 comprising the amino acid sequence of SEQ ID NO: 40, (v) HVR-H2 comprising the amino acid sequence of SEQ ID NO: 41, and (vi) HVR-H3 comprising the amino acid sequence of SEQ ID NO: 42; e) one of the first and second half antibodies comprises (i) HVR-L1 comprising the amino acid sequence of SEQ ID NO: 23, (ii) HVR-L2 comprising the amino acid sequence of SEQ ID NO: 24, (iii) HVR-L3 comprising the amino acid sequence of SEQ ID NO: 25, (iv) HVR-H1 comprising the amino acid sequence of SEQ ID NO: 26, (v) HVR-H2 comprising the amino acid sequence of SEQ ID NO: 27, and (vi) HVR-H3 comprising the amino acid sequence of SEQ ID NO: 28, and the other of the first and second half antibodies comprises (i) HVR-L1 comprising the amino acid sequence of SEQ ID NO: 51, (ii) HVR-L2 comprising the amino acid sequence of SEQ ID NO: 52, (iii) HVR-L3 comprising the amino acid sequence of SEQ ID NO: 53, (iv) HVR-H1 comprising the amino acid sequence of SEQ ID NO: 54, (v) HVR-H2 comprising the amino acid sequence of SEQ ID NO: 55, and (vi) HVR-H3 comprising the amino acid sequence of SEQ ID NO: 56; or f) one of the first and second half antibodies comprises (i) HVR-L1 comprising the amino acid sequence of SEQ ID NO: 37, (ii) HVR-L2 comprising the amino acid sequence of SEQ ID NO: 38, (iii) HVR-L3 comprising the amino acid sequence of SEQ ID NO: 39, (iv) HVR-H1 comprising the amino acid sequence of SEQ ID NO: 40, (v) HVR-H2 comprising the amino acid sequence of SEQ ID NO: 41, and (vi) HVR-H3 comprising the amino acid sequence of SEQ ID NO: 42, and the other of the first and second half antibodies comprises (i) HVR-L1 comprising the amino acid sequence of SEQ ID NO: 51, (ii) HVR-L2 comprising the amino acid sequence of SEQ ID NO: 52, (iii) HVR-L3 comprising the amino acid sequence of SEQ ID NO: 53, (iv) HVR-H1 comprising the amino acid sequence of SEQ ID NO: 54, (v) HVR-H2 comprising the amino acid sequence of SEQ ID NO: 55, and (vi) HVR-H3 comprising the amino acid sequence of SEQ ID NO: 56.

In some embodiments, the antibody comprises first and second half antibodies, wherein the first half antibody comprises a) a VL sequence with at least about 95% sequence identity to SEQ ID NO: 7 and a VH sequence with at least about 95% sequence identity to SEQ ID NO: 8; b) a VL sequence with at least about 95% sequence identity to SEQ ID NO: 21 and a VH sequence with at least about 95% sequence identity to SEQ ID NO: 22; c) a VL sequence with at least about 95% sequence identity to SEQ ID NO: 35 and a VH sequence with at least about 95% sequence identity to SEQ ID NO: 36; or d) a VL sequence with at least about 95% sequence identity to SEQ ID NO: 49 and a VH sequence with at least about 95% sequence identity to SEQ ID NO: 50.

In some embodiments, the antibody comprises first and second half antibodies, wherein the second half antibody comprises a) a VL sequence with at least about 95% sequence identity to SEQ ID NO: 7 and a VH sequence with at least about 95% sequence identity to SEQ ID NO: 8; b) a VL sequence with at least about 95% sequence identity to SEQ ID NO: 21 and a VH sequence with at least about 95% sequence identity to SEQ ID NO: 22; c) a VL sequence with at least about 95% sequence identity to SEQ ID NO: 35 and a VH sequence with at least about 95% sequence identity to SEQ ID NO: 36; or d) a VL sequence with at least about 95% sequence identity to SEQ ID NO: 49 and a VH sequence with at least about 95% sequence identity to SEQ ID NO: 50; wherein the VL and VH sequences of the second half antibody are not identical to the VL and VH sequences of the first half antibody.

In some embodiments, the antibody comprises first and second half antibodies, wherein: a) one of the first and second half antibodies comprises a VL sequence with at least about 95% sequence identity to SEQ ID NO: 7 and a VH sequence with at least about 95% sequence identity to SEQ ID NO: 8, and the other of the first and second half antibodies comprises a VL sequence with at least about 95% sequence identity to SEQ ID NO: 21 and a VH sequence with at least about 95% sequence identity to SEQ ID NO: 22; b) one of the first and second half antibodies comprises a VL sequence with at least about 95% sequence identity to SEQ ID NO: 7 and a VH sequence with at least about 95% sequence identity to SEQ ID NO: 8, and the other of the first and second half antibodies comprises a VL sequence with at least about 95% sequence identity to SEQ ID NO: 35 and a VH sequence with at least about 95% sequence identity to SEQ ID NO: 36; c) one of the first and second half antibodies comprises a VL sequence with at least about 95% sequence identity to SEQ ID NO: 7 and a VH sequence with at least about 95% sequence identity to SEQ ID NO: 8, and the other of the first and second half antibodies comprises a VL sequence with at least about 95% sequence identity to SEQ ID NO: 49 and a VH sequence with at least about 95% sequence identity to SEQ ID NO: 50; d) one of the first and second half antibodies comprises a VL sequence with at least about 95% sequence identity to SEQ ID NO: 21 and a VH sequence with at least about 95% sequence identity to SEQ ID NO: 22, and the other of the first and second half antibodies comprises a VL sequence with at least about 95% sequence identity to SEQ ID NO: 35 and a VH sequence with at least about 95% sequence identity to SEQ ID NO: 36; e) one of the first and second half antibodies comprises a VL sequence with at least about 95% sequence identity to SEQ ID NO: 21 and a VH sequence with at least about 95% sequence identity to SEQ ID NO: 22, and the other of the first and second half antibodies comprises a VL sequence with at least about 95% sequence identity to SEQ ID NO: 49 and a VH sequence with at least about 95% sequence identity to SEQ ID NO: 50; or f) one of the first and second half antibodies comprises a VL sequence with at least about 95% sequence identity to SEQ ID NO: 35 and a VH sequence with at least about 95% sequence identity to SEQ ID NO: 36, and the other of the first and second half antibodies comprises a VL sequence with at least about 95% sequence identity to SEQ ID NO: 49 and a VH sequence with at least about 95% sequence identity to SEQ ID NO: 50.

In some embodiments, the antibody comprises first and second half antibodies, wherein the first half antibody comprises a) a VL sequence of SEQ ID NO: 7 and a VH sequence of SEQ ID NO: 8; b) a VL sequence of SEQ ID NO: 21 and a VH sequence of SEQ ID NO: 22; c) a VL sequence of SEQ ID NO: 35 and a VH sequence of SEQ ID NO: 36; or d) a VL sequence of SEQ ID NO: 49 and a VH sequence of SEQ ID NO: 50.

In some embodiments, the antibody comprises first and second half antibodies, wherein the second half antibody comprises a) a VL sequence of SEQ ID NO: 7 and a VH sequence of SEQ ID NO: 8; b) a VL sequence of SEQ ID NO: 21 and a VH sequence of SEQ ID NO: 22; c) a VL sequence of SEQ ID NO: 35 and a VH sequence of SEQ ID NO: 36; or d) a VL sequence of SEQ ID NO: 49 and a VH sequence of SEQ ID NO: 50; wherein the VL and VH sequences of the second half antibody are not identical to the VL and VH sequences of the first half antibody.

In some embodiments, the antibody comprises first and second half antibodies, wherein: a) one of the first and second half antibodies comprises a VL sequence of SEQ ID NO: 7 and a VH sequence of SEQ ID NO: 8, and the other of the first and second half antibodies comprises a VL sequence of SEQ ID NO: 21 and a VH sequence of SEQ ID NO: 22; b) one of the first and second half antibodies comprises a VL sequence of SEQ ID NO: 7 and a VH sequence of SEQ ID NO: 8, and the other of the first and second half antibodies comprises a VL sequence of SEQ ID NO: 35 and a VH sequence of SEQ ID NO: 36; c) one of the first and second half antibodies comprises a VL sequence of SEQ ID NO: 7 and a VH sequence of SEQ ID NO: 8, and the other of the first and second half antibodies comprises a VL sequence of SEQ ID NO: 49 and a VH sequence of SEQ ID NO: 50; d) one of the first and second half antibodies comprises a VL sequence of SEQ ID NO: 21 and a VH sequence of SEQ ID NO: 22, and the other of the first and second half antibodies comprises a VL sequence of SEQ ID NO: 35 and a VH sequence of SEQ ID NO: 36; e) one of the first and second half antibodies comprises a VL sequence of SEQ ID NO: 21 and a VH sequence of SEQ ID NO: 22, and the other of the first and second half antibodies comprises a VL sequence of SEQ ID NO: 49 and a VH sequence of SEQ ID NO: 50; or f) one of the first and second half antibodies comprises a VL sequence of SEQ ID NO: 35 and a VH sequence of SEQ ID NO: 36, and the other of the first and second half antibodies comprises a VL sequence of SEQ ID NO: 49 and a VH sequence of SEQ ID NO: 50.

In some embodiments, the antibody is a monoclonal antibody. In some embodiments, the antibody is a mouse, rabbit, human, humanized, or chimeric antibody. In some embodiments, the antibody is an IgG antibody. In some embodiments, the antibody is an IgG1, IgG2a, IgG2b, IgG3, or IgG4 antibody. In some embodiments, the antibody is an IgG1 or IgG4 antibody.

In some embodiments, the antibody comprises first and second half antibodies, wherein the first half antibody comprises a first heavy chain constant region comprising a knob mutation and the second half antibody comprises a second heavy chain constant region comprising a hole mutation; or wherein the first half antibody comprises a first heavy chain constant region comprising a hole mutation and the second half antibody comprises a second heavy chain constant region comprising a knob mutation.

In some embodiments, the antibody is an IgG1 antibody and wherein the knob mutation comprises a T366W mutation. In some embodiments, the antibody is an IgG1 antibody and wherein the hole mutation comprises at least one, at least two, or three mutations selected from T366S, L368A, and Y407V. In some embodiments, the antibody is an IgG4 antibody and wherein the knob mutation comprises a T366W mutation. In some embodiments, the antibody is an IgG4 antibody and wherein the hole mutation comprises at least one, at least two, or three mutations selected from T366S, L368A, and Y407V mutations.

In some embodiments, the antibody comprises first and second half antibodies, wherein the first half antibody comprises a) a light chain sequence having at least about 95% sequence identity to SEQ ID NO: 2; b) a light chain sequence having at least about 95% sequence identity to SEQ ID NO: 16; c) a light chain sequence having at least about 95% sequence identity to SEQ ID NO: 30; or d) a light chain sequence having at least about 95% sequence identity to SEQ ID NO: 44.

In some embodiments, the antibody comprises first and second half antibodies, wherein the first half antibody comprises a) a heavy chain sequence having at least about 95% sequence identity to SEQ ID NO: 4; b) a heavy chain sequence having at least about 95% sequence identity to SEQ ID NO: 18; c) a heavy chain sequence having at least about 95% sequence identity to SEQ ID NO: 32; or d) a heavy chain sequence having at least about 95% sequence identity to SEQ ID NO: 46, optionally wherein a C-terminal lysine is missing from one or more heavy chains.

In some embodiments, the antibody comprises first and second half antibodies, wherein the first half antibody comprises a) a light chain sequence having at least about 95% sequence identity to SEQ ID NO: 2 and a heavy chain sequence having at least about 95% sequence identity to SEQ ID NO: 4; b) a light chain sequence having at least about 95% sequence identity to SEQ ID NO: 16 and a heavy chain sequence having at least about 95% sequence identity to SEQ ID NO: 18; c) a light chain sequence having at least about 95% sequence identity to SEQ ID NO: 30 and a heavy chain sequence having at least about 95% sequence identity to SEQ ID NO: 32; or d) a light chain sequence having at least about 95% sequence identity to SEQ ID NO: 44 and a heavy chain sequence having at least about 95% sequence identity to SEQ ID NO: 46, optionally wherein a C-terminal lysine is missing from one or more heavy chains.

In some embodiments, the antibody comprises first and second half antibodies, wherein the first half antibody comprises a) a heavy chain sequence having at least about 95% sequence identity to SEQ ID NO: 6; b) a heavy chain sequence having at least about 95% sequence identity to SEQ ID NO: 20; c) a heavy chain sequence having at least about 95% sequence identity to SEQ ID NO: 34; or d) a heavy chain sequence having at least about 95% sequence identity to SEQ ID NO: 48, optionally wherein a C-terminal lysine is missing from one or more heavy chains.

In some embodiments, the antibody comprises first and second half antibodies, wherein the first half antibody comprises a) a light chain sequence having at least about 95% sequence identity to SEQ ID NO: 2 and a heavy chain sequence having at least about 95% sequence identity to SEQ ID NO: 6; b) a light chain sequence having at least about 95% sequence identity to SEQ ID NO: 16 and a heavy chain sequence having at least about 95% sequence identity to SEQ ID NO: 20; c) a light chain sequence having at least about 95% sequence identity to SEQ ID NO: 30 and a heavy chain sequence having at least about 95% sequence identity to SEQ ID NO: 34; or d) a light chain sequence having at least about 95% sequence identity to SEQ ID NO: 44 and a heavy chain sequence having at least about 95% sequence identity to SEQ ID NO: 48, optionally wherein a C-terminal lysine is missing from one or more heavy chains.

In some embodiments, the antibody comprises first and second half antibodies, wherein the second half antibody comprises a) a light chain sequence having at least about 95% sequence identity to SEQ ID NO: 2; b) a light chain sequence having at least about 95% sequence identity to SEQ ID NO: 16; c) a light chain sequence having at least about 95% sequence identity to SEQ ID NO: 30; or d) a light chain sequence having at least about 95% sequence identity to SEQ ID NO: 44; wherein the light chain and heavy chain sequences of the second half antibody are not identical to the light chain and heavy chain sequences of the first half antibody.

In some embodiments, the antibody comprises first and second half antibodies, wherein the second half antibody comprises a) a heavy chain sequence having at least about 95% sequence identity to SEQ ID NO: 4; b) a heavy chain sequence having at least about 95% sequence identity to SEQ ID NO: 18; c) a heavy chain sequence having at least about 95% sequence identity to SEQ ID NO: 32; or d) a heavy chain sequence having at least about 95% sequence identity to SEQ ID NO: 46; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a light chain sequence having at least about 95% sequence identity to SEQ ID NO: 2 and a heavy chain sequence having at least about 95% sequence identity to SEQ ID NO: 4; b) a light chain sequence having at least about 95% sequence identity to SEQ ID NO: 16 and a heavy chain sequence having at least about 95% sequence identity to SEQ ID NO: 18; c) a light chain sequence having at least about 95% sequence identity to SEQ ID NO: 30 and a heavy chain sequence having at least about 95% sequence identity to SEQ ID NO: 32; or d) a light chain sequence having at least about 95% sequence identity to SEQ ID NO: 44 and a heavy chain sequence having at least about 95% sequence identity to SEQ ID NO: 46; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a heavy chain sequence having at least about 95% sequence identity to SEQ ID NO: 6; b) a heavy chain sequence having at least about 95% sequence identity to SEQ ID NO: 20; c) a heavy chain sequence having at least about 95% sequence identity to SEQ ID NO: 34; or d) a heavy chain sequence having at least about 95% sequence identity to SEQ ID NO: 48; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a light chain sequence having at least about 95% sequence identity to SEQ ID NO: 2 and a heavy chain sequence having at least about 95% sequence identity to SEQ ID NO: 6; b) a light chain sequence having at least about 95% sequence identity to SEQ ID NO: 16 and a heavy chain sequence having at least about 95% sequence identity to SEQ ID NO: 20; c) a light chain sequence having at least about 95% sequence identity to SEQ ID NO: 30 and a heavy chain sequence having at least about 95% sequence identity to SEQ ID NO: 34; or d) a light chain sequence having at least about 95% sequence identity to SEQ ID NO: 44 and a heavy chain sequence having at least about 95% sequence identity to SEQ ID NO: 48; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein: a) one of the first and second half antibodies comprises a light chain sequence having at least about 95% sequence identity to SEQ ID NO: 2 and a heavy chain sequence having at least about 95% sequence identity to SEQ ID NO: 4, and the other of the first and second half antibodies comprises a light chain sequence having at least about 95% sequence identity to SEQ ID NO: 16 and a heavy chain sequence having at least about 95% sequence identity to SEQ ID NO: 20; b) one of the first and second half antibodies comprises a light chain sequence having at least about 95% sequence identity to SEQ ID NO: 2 and a heavy chain sequence having at least about 95% sequence identity to SEQ ID NO: 4, and the other of the first and second half antibodies comprises a light chain sequence having at least about 95% sequence identity to SEQ ID NO: 30 and a heavy chain sequence having at least about 95% sequence identity to SEQ ID NO: 34; c) one of the first and second half antibodies comprises a light chain sequence having at least about 95% sequence identity to SEQ ID NO: 2 and a heavy chain sequence having at least about 95% sequence identity to SEQ ID NO: 4, and the other of the first and second half antibodies comprises a light chain sequence having at least about 95% sequence identity to SEQ ID NO: 44 and a heavy chain sequence having at least about 95% sequence identity to SEQ ID NO: 48; d) one of the first and second half antibodies comprises a light chain sequence having at least about 95% sequence identity to SEQ ID NO: 2 and a heavy chain sequence having at least about 95% sequence identity to SEQ ID NO: 6, and the other of the first and second half antibodies comprises a light chain sequence having at least about 95% sequence identity to SEQ ID NO: 16 and a heavy chain sequence having at least about 95% sequence identity to SEQ ID NO: 18; e) one of the first and second half antibodies comprises a light chain sequence having at least about 95% sequence identity to SEQ ID NO: 2 and a heavy chain sequence having at least about 95% sequence identity to SEQ ID NO: 6, and the other of the first and second half antibodies comprises a light chain sequence having at least about 95% sequence identity to SEQ ID NO: 30 and a heavy chain sequence having at least about 95% sequence identity to SEQ ID NO: 32; f) one of the first and second half antibodies comprises a light chain sequence having at least about 95% sequence identity to SEQ ID NO: 2 and a heavy chain sequence having at least about 95% sequence identity to SEQ ID NO: 6, and the other of the first and second half antibodies comprises a light chain sequence having at least about 95% sequence identity to SEQ ID NO: 44 and a heavy chain sequence having at least about 95% sequence identity to SEQ ID NO: 46; g) one of the first and second half antibodies comprises a light chain sequence having at least about 95% sequence identity to SEQ ID NO: 16 and a heavy chain sequence having at least about 95% sequence identity to SEQ ID NO: 18, and the other of the first and second half antibodies comprises a light chain sequence having at least about 95% sequence identity to SEQ ID NO: 30 and a heavy chain sequence having at least about 95% sequence identity to SEQ ID NO: 34; h) one of the first and second half antibodies comprises a light chain sequence having at least about 95% sequence identity to SEQ ID NO: 16 and a heavy chain sequence having at least about 95% sequence identity to SEQ ID NO: 18, and the other of the first and second half antibodies comprises a light chain sequence having at least about 95% sequence identity to SEQ ID NO: 44 and a heavy chain sequence having at least about 95% sequence identity to SEQ ID NO: 48; i) one of the first and second half antibodies comprises a light chain sequence having at least about 95% sequence identity to SEQ ID NO: 30 and a heavy chain sequence having at least about 95% sequence identity to SEQ ID NO: 32, and the other of the first and second half antibodies comprises a light chain sequence having at least about 95% sequence identity to SEQ ID NO: 44 and a heavy chain sequence having at least about 95% sequence identity to SEQ ID NO: 48; j) one of the first and second half antibodies comprises a light chain sequence having at least about 95% sequence identity to SEQ ID NO: 16 and a heavy chain sequence having at least about 95% sequence identity to SEQ ID NO: 20, and the other of the first and second half antibodies comprises a light chain sequence having at least about 95% sequence identity to SEQ ID NO: 30 and a heavy chain sequence having at least about 95% sequence identity to SEQ ID NO: 32; k) one of the first and second half antibodies comprises a light chain sequence having at least about 95% sequence identity to SEQ ID NO: 16 and a heavy chain sequence having at least about 95% sequence identity to SEQ ID NO: 20, and the other of the first and second half antibodies comprises a light chain sequence having at least about 95% sequence identity to SEQ ID NO: 44 and a heavy chain sequence having at least about 95% sequence identity to SEQ ID NO: 46; or l) one of the first and second half antibodies comprises a light chain sequence having at least about 95% sequence identity to SEQ ID NO: 30 and a heavy chain sequence having at least about 95% sequence identity to SEQ ID NO: 34, and the other of the first and second half antibodies comprises a light chain sequence having at least about 95% sequence identity to SEQ ID NO: 44 and a heavy chain sequence having at least about 95% sequence identity to SEQ ID NO: 46, optionally wherein a C-terminal lysine is missing from one or more heavy chains.

In some embodiments, the antibody comprises first and second half antibodies, wherein the first half antibody comprises a) a light chain sequence of SEQ ID NO: 2; b) a light chain sequence of SEQ ID NO: 16; c) a light chain sequence of SEQ ID NO: 30; or d) a light chain sequence of SEQ ID NO: 44.

In some embodiments, the antibody comprises first and second half antibodies, wherein the first half antibody comprises a) a heavy chain sequence of SEQ ID NO: 4; b) a heavy chain sequence of SEQ ID NO: 18; c) a heavy chain sequence of SEQ ID NO: 32; or d) a heavy chain sequence of SEQ ID NO: 46, optionally wherein a C-terminal lysine is missing from one or more heavy chains.

In some embodiments, the antibody comprises first and second half antibodies, wherein the first half antibody comprises a) a light chain sequence of SEQ ID NO: 2 and a heavy chain sequence of SEQ ID NO: 4; b) a light chain sequence of SEQ ID NO: 16 and a heavy chain sequence of SEQ ID NO: 18; c) a light chain sequence of SEQ ID NO: 30 and a heavy chain sequence of SEQ ID NO: 32; or d) a light chain sequence of SEQ ID NO: 44 and a heavy chain sequence of SEQ ID NO: 46, optionally wherein a C-terminal lysine is missing from one or more heavy chains.

In some embodiments, the antibody comprises first and second half antibodies, wherein the first half antibody comprises a) a heavy chain sequence of SEQ ID NO: 6; b) a heavy chain sequence of SEQ ID NO: 20; c) a heavy chain sequence of SEQ ID NO: 34; or d) a heavy chain sequence of SEQ ID NO: 48, optionally wherein a C-terminal lysine is missing from one or more heavy chains.

In some embodiments, the antibody comprises first and second half antibodies, wherein the first half antibody comprises a) a light chain sequence of SEQ ID NO: 2 and a heavy chain sequence of SEQ ID NO: 6; b) a light chain sequence of SEQ ID NO: 16 and a heavy chain sequence of SEQ ID NO: 20; c) a light chain sequence of SEQ ID NO: 30 and a heavy chain sequence of SEQ ID NO: 34; or d) a light chain sequence of SEQ ID NO: 44 and a heavy chain sequence of SEQ ID NO: 48, optionally wherein a C-terminal lysine is missing from one or more heavy chains.

In some embodiments, the antibody comprises first and second half antibodies, wherein the second half antibody comprises a) a light chain sequence of SEQ ID NO: 2; b) a light chain sequence of SEQ ID NO: 16; c) a light chain sequence of SEQ ID NO: 30; or d) a light chain sequence of SEQ ID NO: 44; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a heavy chain sequence of SEQ ID NO: 4; b) a heavy chain sequence of SEQ ID NO: 18; c) a heavy chain sequence of SEQ ID NO: 32; or d) a heavy chain sequence of SEQ ID NO: 46; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a light chain sequence of SEQ ID NO: 2 and a heavy chain sequence of SEQ ID NO: 4; b) a light chain sequence of SEQ ID NO: 16 and a heavy chain sequence of SEQ ID NO: 18; c) a light chain sequence of SEQ ID NO: 30 and a heavy chain sequence of SEQ ID NO: 32; or d) a light chain sequence of SEQ ID NO: 44 and a heavy chain sequence of SEQ ID NO: 46; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a heavy chain sequence of SEQ ID NO: 6; b) a heavy chain sequence of SEQ ID NO: 20; c) a heavy chain sequence of SEQ ID NO: 34; or d) a heavy chain sequence of SEQ ID NO: 48; wherein the light chain and heavy chain sequences of the second half antibody are not identical to the light chain and heavy chain sequences of the first half antibody, optionally wherein a C-terminal lysine is missing from one or more heavy chains.

In some embodiments, the antibody comprises first and second half antibodies, wherein the second half antibody comprises a) a light chain sequence of SEQ ID NO: 2 and a heavy chain sequence of SEQ ID NO: 6; b) a light chain sequence of SEQ ID NO: 16 and a heavy chain sequence of SEQ ID NO: 20; c) a light chain sequence of SEQ ID NO: 30 and a heavy chain sequence of SEQ ID NO: 34; or d) a light chain sequence of SEQ ID NO: 44 and a heavy chain sequence of SEQ ID NO: 48; wherein the light chain and heavy chain sequences of the second half antibody are not identical to the light chain and heavy chain sequences of the first half antibody.

In some embodiments, the antibody comprises first and second half antibodies, wherein: a) the first half antibody comprises a light chain sequence of SEQ ID NO: 2 and a heavy chain sequence of SEQ ID NO: 4, and the second half antibody comprises a light chain sequence of SEQ ID NO: 16 and a heavy chain sequence of SEQ ID NO: 20; b) the first half antibody comprises a light chain sequence of SEQ ID NO: 2 and a heavy chain sequence of SEQ ID NO: 4, and the second half antibody comprises a light chain sequence of SEQ ID NO: 30 and a heavy chain sequence of SEQ ID NO: 34; c) the first half antibody comprises a light chain sequence of SEQ ID NO: 2 and a heavy chain sequence of SEQ ID NO: 4, and the second half antibody comprises a light chain sequence of SEQ ID NO: 44 and a heavy chain sequence of SEQ ID NO: 48; d) the first half antibody comprises a light chain sequence of SEQ ID NO: 2 and a heavy chain sequence of SEQ ID NO: 6, and the second half antibody comprises a light chain sequence of SEQ ID NO: 16 and a heavy chain sequence of SEQ ID NO: 18; e) the first half antibody comprises a light chain sequence of SEQ ID NO: 2 and a heavy chain sequence of SEQ ID NO: 6, and the second half antibody comprises a light chain sequence of SEQ ID NO: 30 and a heavy chain sequence of SEQ ID NO: 32; f) the first half antibody comprises a light chain sequence of SEQ ID NO: 2 and a heavy chain sequence of SEQ ID NO: 6, and the second half antibody comprises a light chain sequence of SEQ ID NO: 44 and a heavy chain sequence of SEQ ID NO: 46; g) the first half antibody comprises a light chain sequence of SEQ ID NO: 16 and a heavy chain sequence of SEQ ID NO: 18, and the second half antibody comprises a light chain sequence of SEQ ID NO: 30 and a heavy chain sequence of SEQ ID NO: 34; h) the first half antibody comprises a light chain sequence of SEQ ID NO: 16 and a heavy chain sequence of SEQ ID NO: 18, and the second half antibody comprises a light chain sequence of SEQ ID NO: 44 and a heavy chain sequence of SEQ ID NO: 48; l) the first half antibody comprises a light chain sequence of SEQ ID NO: 30 and a heavy chain sequence of SEQ ID NO: 32, and the second half antibody comprises a light chain sequence of SEQ ID NO: 44 and a heavy chain sequence of SEQ ID NO: 48; j) the first half antibody comprises a light chain sequence of SEQ ID NO: 16 and a heavy chain sequence of SEQ ID NO: 20, and the second half antibody comprises a light chain sequence of SEQ ID NO: 30 and a heavy chain sequence of SEQ ID NO: 32; k) the first half antibody comprises a light chain sequence of SEQ ID NO: 16 and a heavy chain sequence of SEQ ID NO: 20, and the second half antibody comprises a light chain sequence of SEQ ID NO: 44 and a heavy chain sequence of SEQ ID NO: 46; or 1) the first half antibody comprises a light chain sequence of SEQ ID NO: 30 and a heavy chain sequence of SEQ ID NO: 34, and the second half antibody comprises a light chain sequence of SEQ ID NO: 44 and a heavy chain sequence of SEQ ID NO: 46; optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 4, and the second half antibody comprises a light chain sequence of SEQ ID NO: 16 and a heavy chain sequence of SEQ ID NO: 20, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 4, and the second half antibody comprises a light chain sequence of SEQ ID NO: 30 and a heavy chain sequence of SEQ ID NO: 34, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 4, and the second half antibody comprises a light chain sequence of SEQ ID NO: 44 and a heavy chain sequence of SEQ ID NO: 48, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 6, and the second half antibody comprises a light chain sequence of SEQ ID NO: 16 and a heavy chain sequence of SEQ ID NO: 18, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 6, and the second half antibody comprises a light chain sequence of SEQ ID NO: 30 and a heavy chain sequence of SEQ ID NO: 32, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 6, and the second half antibody comprises a light chain sequence of SEQ ID NO: 44 and a heavy chain sequence of SEQ ID NO: 46, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 18, and the second half antibody comprises a light chain sequence of SEQ ID NO: 30 and a heavy chain sequence of SEQ ID NO: 34, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 18, and the second half antibody comprises a light chain sequence of SEQ ID NO: 44 and a heavy chain sequence of SEQ ID NO: 48, and optionally wherein a C-terminal lysine is missing from one or more heavy chains.

In some embodiments, the antibody comprises first and second half antibodies, wherein the first half antibody comprises a light chain sequence of SEQ ID NO: 30 and a heavy chain sequence of SEQ ID NO: 32, and the second half antibody comprises a light chain sequence of SEQ ID NO: 44 and a heavy chain sequence of SEQ ID NO: 48, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 20, and the second half antibody comprises a light chain sequence of SEQ ID NO:

30 and a heavy chain sequence of SEQ ID NO: 32, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 20, and the second half antibody comprises a light chain sequence of SEQ ID NO: 44 and a heavy chain sequence of SEQ ID NO: 46, and optionally wherein a C-terminal lysine is missing from one or more heavy chains.

In some embodiments, the antibody comprises first and second half antibodies, wherein the first half antibody comprises a light chain sequence of SEQ ID NO: 30 and a heavy chain sequence of SEQ ID NO: 34, and the second half antibody comprises a light chain sequence of SEQ ID NO: 44 and a heavy chain sequence of SEQ ID NO: 46, and optionally wherein a C-terminal lysine is missing from one or more heavy chains.

Also provided herein is an antibody that competes with an antibody disclosed herein for binding to a mixed-topology polyubiquitin. Also provided herein is an antibody that binds the same epitopes of a mixed-topology polyubiquitin as an antibody disclosed herein.

In some embodiments, an antibody provided herein is a bispecific antibody. In some embodiments, the antibody is a diabody, triabody, or tetrabody.

In some embodiments, the antibody is conjugated to a label. In some embodiments, the label is a fluorescent, enzymatic, or chromogenic label. In some embodiments, the label is a radioisotope, which is optionally a positron emitter, which is optionally $^{89}$Zr.

Also provided herein is a composition comprising an antibody disclosed herein, wherein the composition is substantially free of monospecific antibodies, unassembled half antibodies, or both monospecific antibodies and unassembled half antibodies.

Also provided herein is an immunoconjugate comprising an antibody disclosed herein and a cytotoxic agent.

Also provided herein is a pharmaceutical formulation comprising a pharmaceutically acceptable carrier and at least one of an the antibody or immunoconjugate disclosed herein. In some embodiments, the composition is substantially free of monospecific antibodies, unassembled half antibodies, or both monospecific antibodies and unassembled half antibodies.

Also provided herein is an isolated nucleic acid encoding: an antibody disclosed herein; a first half antibody of an antibody disclosed herein; or a second half antibody of an antibody disclosed herein. Also provided herein is a host cell comprising a nucleic acid disclosed herein. Also provided herein is a method of producing an antibody or half-antibody comprising culturing a host cell disclosed herein so that the antibody or half antibody is produced.

Also provided herein is a method of making an antibody disclosed herein, comprising forming the antibody from a first half antibody and a second half antibody.

Also provided herein is a method of detecting a mixed-topology polyubiquitin in a biological sample comprising contacting the biological sample with an antibody disclosed herein under conditions permissive for binding of the antibody to the mixed-topology polyubiquitin, and detecting whether a complex is formed between the antibody and mixed-topology polyubiquitin in the biological sample. In some embodiments, the mixed-topology polyubiquitin is covalently attached to a non-ubiquitin polypeptide. In some embodiments, the mixed-topology polyubiquitin is branched. In some embodiments, the mixed-topology polyubiquitin is unbranched. In some embodiments, the mixed-topology polyubiquitin comprises a first linkage and a second linkage different from the first linkage, and the first and second linkages are each independently a K11, K48, K63, or C-terminal to N-terminal linkage. In some embodiments, the mixed-topology polyubiquitin comprises a K11 linkage and a second linkage different from the K11 linkage. In some embodiments, the mixed-topology polyubiquitin comprises a K48 linkage and a second linkage different from the K48 linkage. In some embodiments, the mixed-topology polyubiquitin comprises a K63 linkage and a second linkage different from the K63 linkage. In some embodiments, the mixed-topology polyubiquitin comprises a C- to N-terminal linkage and a second linkage different from the C- to N-terminal linkage. In some embodiments, wherein the mixed-topology polyubiquitin comprises: a K11 linkage and a K48 linkage; a K11 linkage and a K63 linkage; a K11 linkage and a C- to N-terminal linkage; a K48 linkage and a K63 linkage; a K48 linkage and a C- to N-terminal linkage; or a K63 linkage and a C- to N-terminal linkage.

Also provided herein is a method of detecting a polyubiquitinated protein in a biological sample, the polyubiquitinated protein being polyubiquitinated at two or more positions with at least first and second polyubiquitins, with the first and second polyubiquitins having different linkages, comprising contacting the biological sample with an antibody provided herein under conditions permissive for binding of the antibody to the polyubiquitinated protein, and detecting whether a complex is formed between the antibody and polyubiquitinated protein in the biological sample. In some embodiments, the first and second polyubiquitins respectively comprise: a K11 linkage and a second linkage different from the K11 linkage; a K48 linkage and a second linkage different from the K48 linkage; a K63 linkage and a second linkage different from the K63 linkage; a C- to N-terminal linkage and a second linkage different from the C- to N-terminal linkage; a K11 linkage and a K48 linkage; a K11 linkage and a K63 linkage; a K41 linkage and a C- to N-terminal linkage; a K48 linkage and a K63 linkage; a K48 linkage and a C- to N-terminal linkage; or a K63 linkage and a C- to N-terminal linkage.

BRIEF DESCRIPTION OF THE FIGURES

FIGS. 1a-d. Engineering, purification, and characterization of a bispecific anti-K11/K48 polyubiquitin linkage-specific antibody. a, Knob and hole half antibodies were recombinantly expressed separately in CHO cells and affinity purified individually and then assembled in vitro. b, SDS-PAGE analysis of knob and hole half antibodies and assembled bispecific antibodies post purification. Samples were run in the absence (−) or presence (+) of DTT. The HL label denotes a half antibody species and the H2L2 label denotes a full antibody. In the reduced samples the heavy chains (H) and light chains (L) are indicated. c, Analytical size-exclusion analysis of the anti-K11 knob and anti-K48 hole half antibodies and the assembled anti-K11/K48 bispecific antibody. d, Mass spectrometry analysis of the purified anti-K11/K48 bispecific antibody. Top panel is in the absence of carboxypeptidase B (CPB) and the bottom panel is after digest with CPB.

FIGS. 2a-c. Characterization of the half antibodies and control bispecific antibodies. a, Analytical size-exclusion analysis of the anti-K11 hole and anti-gD knob half antibodies and the assembled anti-K11/gD and anti-K48/gD bispecific control antibodies. b, Mass spectrometry analysis of the affinity purified anti-K11 knob, anti-K11 hole, anti-K48 hole, and anti-gD knob half antibodies. Top panel for each half antibody is in the absence of carboxypeptidase B (CPB) and the bottom panel is after digest with CPB. Arrows in the top panels indicate a +128 Da addition to the anti-K11 knob, anti-K11 hole, and anti-gD knob half antibodies that disappears upon CPB treatment indicating that it is due to the heavy chain carboxy-terminal lysine still attached to a portion of the antibodies. c, Mass spectrometry analysis of the purified anti-K11/gD and anti-K48/gD control bispecific antibodies. Top panel for each bispecific is in the absence of carboxypeptidase B (CPB) and the bottom panel is after digest with CPB.

DETAILED DESCRIPTION OF CERTAIN EMBODIMENTS

I. Definitions

Figure 2A:
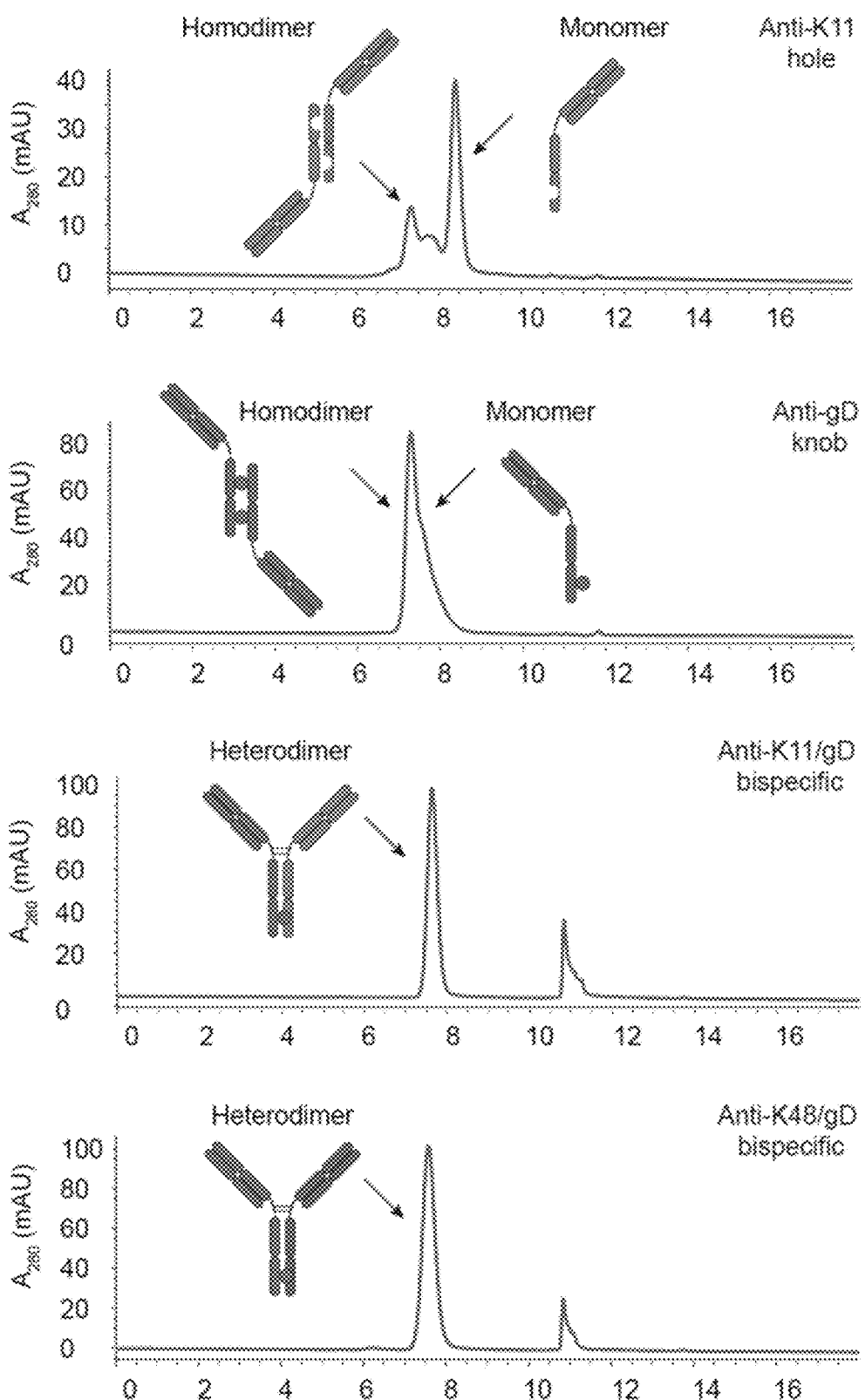

As used herein, VH refers to a heavy chain variable domain and VL refers to a light chain variable domain.

An "acceptor human framework" for the purposes herein is a framework comprising the amino acid sequence of a VL framework or a VH framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

As used herein, "about" refers to a value that is 10% more or less than a stated value, gives results functionally equivalent to the stated value, or rounds to the stated value.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

"Avidity" refers to the strength of the sum total of noncovalent interactions between a molecule (e.g., an antibody) and its binding partner (e.g., a target molecule comprising one or more antigens). The avidity of a molecule X for its partner Y can generally be represented by the dissociation constant (Kd). A bispecific antibody will generally have a greater avidity for a binding partner comprising epitopes recognized by both of the antigen binding sites of the bispecific antibody than for a binding partner comprising either of the epitopes individually. Avidity can be measured by common methods known in the art, including those described herein. Specific illustrative and exemplary embodiments for measuring binding avidity are described in the following. The term "functional affinity" is sometimes used in the art to refer to avidity.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

An "agonist antibody" as used herein is an antibody which mimics at least one of the functional activities of a polypeptide of interest.

An "antagonist antibody" or a "blocking antibody" is an antibody which inhibits or reduces biological activity of the antigen to which it specifically binds. Certain blocking antibodies or antagonist antibodies substantially or completely inhibit the biological activity of the antigen.

The term "antibody drug conjugate" (ADC) as used herein is equivalent to the term "immunoconjugate".

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "anti-mixed-topology polyubiquitin antibody" and "an antibody that binds to mixed-topology polyubiquitin" refer to an antibody that is capable of binding mixed-topology linked polyubiquitin with sufficient avidity such that the antibody is useful as a diagnostic and/or therapeutic agent in targeting mixed-topology polyubiquitin. In some embodiments, the extent of binding of an anti-mixed-topology polyubiquitin antibody to an unrelated, non-mixed-topology-linked polyubiquitin protein is less than about 10% of the binding of the antibody to mixed-topology polyubiquitin as measured, e.g., by a radioimmunoassay (RIA). In certain embodiments, an antibody that binds to mixed-topology polyubiquitin has a dissociation constant (Kd) of ≤1 µM, ≤100 nM, ≤10 nM, ≤1 nM, 0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-mixed-topology polyubiquitin antibody binds to epitopes of the mixed-topology polyubiquitin that are conserved among the mixed-topology polyubiquitin from different species.

As used herein, the term "anti-polyubiquitin antibody" refers to an antibody that is capable of specifically binding to a polyubiquitin molecule.

As used herein, the terms "anti-ubiquitin antibody" and "anti-monoubiquitin antibody" are used interchangeably, and refer to an antibody that is capable of specifically binding to a ubiquitin molecule.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In some embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

As used herein, "first," "second," etc. are used with reference to elements of a complex structure, e.g., a protein with tertiary/quaternary structure such as an antibody or other assembly such as a polyubiquitin, to refer to those elements (e.g., monomers, chains, domains) without any implication as to the ordering or positioning of the elements; thus a "first" element may be C- or N-terminal to a second element, or closer or farther from one end or another of the structure than a second element. Thus, for example, with reference to the halves of a bispecific antibody or to linkages in a mixed-topology polyubiquitin, the designation of a half or a linkage as first or second is arbitrary.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "rabbit antibody" is one which possesses an amino acid sequence which corresponds to that of an antibody produced by a rabbit or a rabbit cell or derived from a non-rabbit source that utilizes rabbit antibody repertoires or other rabbit antibody-encoding sequences.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda MD (1991), vols. 1-3. In some embodiments, for the VL, the subgroup is subgroup kappa I as in Kabat et al., supra. In some embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent. An immunoconjugate is equivalent to the term "antibody drug conjugate" (ADC).

An "individual" or "patient" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoresis (e.g., SDS-PAGE, isoelectric focusing (IEF), capillary electrophoresis) or chromatography (e.g., ion exchange or reverse phase HPLC). For a review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Mixed-topology polyubiquitin" refers to polyubiquitin comprising two or more different Ub to Ub linkages, i.e., different linkages at different positions in the polyubiquitin, and may be branched (wherein at least one monomer is connected to at least three other monomers or to a substrate polypeptide and at least two other monomers) or unbranched (wherein the monomers are not connected to more than two other monomers or to two monomers and a substrate polypeptide). Thus, in a branched mixed-topology polyubiquitin, there would be a ubiquitin at the branch point with its C-terminus linked to, e.g., lysine 11 of the previous ubiquitin, while, e.g., the lysine 11 and the lysine 48 of the ubiquitin at the branch point could both be linked to subsequent ubiquitins. In an unbranched mixed-topology polyubiquitin, none of the ubiquitins would be connected directly to more than two other ubiquitins, but at least one of the ubiquitins would be involved in two different ubiquitin to ubiquitin linkages, e.g., its C-terminus could be linked to lysine 11 of the previous ubiquitin while its lysine 48 is linked to the subsequent ubiquitin.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Or" is used in the inclusive sense, i.e., equivalent to "and/or," unless the context requires otherwise.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "substantially free of" means that the referenced entity is absent or, if present, is (i) in a sufficiently low quantity so as not to significantly alter a functional property or result of a composition, method, use, or step, as the case may be; (ii) is undetectable by at least one appropriate analytical method, such as mass spectrometry (e.g., MALDI-TOF or any MS procedure used in the Examples), blotting (e.g., Western for a polypeptide), or electrophoresis (e.g., SDS-PAGE with Coomassie blue or silver staining); or (iii) is present in an amount less than or equal to about 20%, 15%, 10%, 5%, 4%, 3%, 2%, 1%, 0.5%, or 0.1%, by mass or by mole fraction relative to the total amount of non-solvent material in the composition.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies disclosed herein are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In some aspects, antibodies that bind to mixed-topology polyubiquitin chains are provided. Such antibodies are useful, e.g., for detecting, modulating the activity of, or immunoprecipitating mixed-topology polyubiquitin chains.

A. Exemplary Antibodies

In some embodiments, an antibody has a greater avidity for a mixed-topology polyubiquitin than for a single-topology polyubiquitin, wherein the mixed-topology polyubiquitin comprises a first linkage and a second linkage, wherein the first linkage and the second linkage differ from each other. In some embodiments, an antibody is a multispecific antibody that binds a mixed-topology polyubiquitin comprising a first linkage and a second linkage, the antibody comprising a first VH/VL unit specific for the first linkage, and a second VH/VL unit specific for the second linkage, wherein the first linkage and the second linkage differ from each other. For example, an antibody can comprise a first antigen recognition site and a second antigen recognition site, wherein the first antigen recognition site is specific for the first linkage and the second antigen recognition site is specific for the second linkage. Because both antigen recognition sites can specifically engage a mixed-topology polyubiquitin whereas only one antigen recognition site can specifically engage a single-topology polyubiquitin, the antibody has greater avidity for the mixed-topology polyubiquitin.

In some embodiments, the first linkage is a K11, K48, K63, or C-terminal to N-terminal-linkage. In some embodiments, the second linkage is a K11, K48, K63, or C-terminal to N-terminal-linkage. In some embodiments, the first and second linkages are independently a K11, K48, K63, or C-terminal to N-terminal-linkage. Unless otherwise indicated, the first and second linkages are different.

The antibodies, antibody sequences, and sequence listing disclosed in U.S. Pat. No. 7,763,245 are incorporated herein by reference. In some embodiments, the first or second half antibody comprises the HVR-H1, HVR-H2, HVR-H3, HVR-L1, HVR-L2, and HVR-L3 of an antibody disclosed in U.S. Pat. No. 7,763,245 that binds a polyubiquitin. In some embodiments, the first or second half antibody comprises a combination of HVR-H1, HVR-H2, HVR-H3, HVR-L1, HVR-L2, and HVR-L3 selected from the HVRs disclosed in U.S. Pat. No. 7,763,245, wherein the half antibody binds a polyubiquitin.

The antibodies, antibody sequences, and sequence listing disclosed in U.S. Pat. No. 8,133,488 are incorporated herein by reference. In some embodiments, the first or second half antibody comprises the HVR-H1, HVR-H2, HVR-H3, HVR-L1, HVR-L2, and HVR-L3 of an antibody disclosed in U.S. Pat. No. 8,133,488 that binds a polyubiquitin. In some embodiments, the first or second half antibody comprises a combination of HVR-H1, HVR-H2, HVR-H3, HVR-L1, HVR-L2, and HVR-L3 selected from the HVRs disclosed in U.S. Pat. No. 8,133,488, wherein the half antibody binds a polyubiquitin.

The antibodies, antibody sequences, and sequence listing disclosed in U.S. Pat. No. 8,992,919 are incorporated herein by reference. In some embodiments, the first or second half antibody comprises the HVR-H1, HVR-H2, HVR-H3, HVR-L1, HVR-L2, and HVR-L3 of an antibody disclosed in U.S. Pat. No. 8,992,919 that binds a polyubiquitin. In some embodiments, the first or second half antibody comprises a combination of HVR-H1, HVR-H2, HVR-H3, HVR-L1, HVR-L2, and HVR-L3 selected from the HVRs disclosed in U.S. Pat. No. 8,992,919, wherein the half antibody binds a polyubiquitin.

The antibodies, antibody sequences, and sequence listing disclosed in U.S. Pat. No. 9,321,844 are incorporated herein by reference. In some embodiments, the first or second half antibody comprises the HVR-H1, HVR-H2, HVR-H3, HVR-L1, HVR-L2, and HVR-L3 of an antibody disclosed in U.S. Pat. No. 9,321,844 that binds a polyubiquitin. In some embodiments, the first or second half antibody comprises a combination of HVR-H1, HVR-H2, HVR-H3, HVR-L1, HVR-L2, and HVR-L3 selected from the HVRs disclosed in U.S. Pat. No. 9,321,844, wherein the half antibody binds a polyubiquitin.

Unless otherwise indicated, at least one of the HVRs of the second half antibody is not identical to the corresponding HVR of the first half antibody. In some embodiments, at least two of the HVRs of the second half antibody are not identical to the corresponding HVRs of the first half antibody. In some embodiments, at least three of the HVRs of the second half antibody are not identical to the corresponding HVRs of the first half antibody. In some embodiments, at least four of the HVRs of the second half antibody are not identical to the corresponding HVR of the first half antibody. In some embodiments, at least five of the HVRs of the second half antibody are not identical to the corresponding HVRs of the first half antibody. In some embodiments, the six HVRs of the second half antibody are not identical to the HVRs of the first half antibody.

In some embodiments, the first half antibody comprises an HVR-L1, HVR-L2, HVR-L3, HVR-H1, HVR-H2, and HVR-H3 comprising the amino acid sequences of SEQ ID NOs: 9, 10, 11, 12, 13, and 14, respectively. In some embodiments, the first half antibody comprises an HVR-L1, HVR-L2, HVR-L3, HVR-H1, HVR-H2, and HVR-H3 comprising the amino acid sequences of SEQ ID NOs: 23, 24, 25, 26, 27, and 28, respectively. In some embodiments, the first half antibody comprises an HVR-L1, HVR-L2, HVR-L3, HVR-H1, HVR-H2, and HVR-H3 comprising the amino acid sequences of SEQ ID NOs: 37, 38, 39, 40, 41, and 42, respectively. In some embodiments, the first half antibody comprises an HVR-L1, HVR-L2, HVR-L3, HVR-H1, HVR-H2, and HVR-H3 comprising the amino acid sequences of SEQ ID NOs: 51, 52, 53, 54, 55, and 56, respectively.

In some embodiments, the second half antibody comprises an HVR-L1, HVR-L2, HVR-L3, HVR-H1, HVR-H2, and HVR-H3 comprising the amino acid sequences of SEQ ID NOs: 9, 10, 11, 12, 13, and 14, respectively. In some embodiments, the second half antibody comprises an HVR-L1, HVR-L2, HVR-L3, HVR-H1, HVR-H2, and HVR-H3 comprising the amino acid sequences of SEQ ID NOs: 23, 24, 25, 26, 27, and 28, respectively. In some embodiments, the second half antibody comprises an HVR-L1, HVR-L2, HVR-L3, HVR-H1, HVR-H2, and HVR-H3 comprising the amino acid sequences of SEQ ID NOs: 37, 38, 39, 40, 41, and 42, respectively. In some embodiments, the second half antibody comprises an HVR-L1, HVR-L2, HVR-L3, HVR-H1, HVR-H2, and HVR-H3 comprising the amino acid sequences of SEQ ID NOs: 51, 52, 53, 54, 55, and 56, respectively.

In some embodiments, one of the first and second half antibodies comprises
  (i) HVR-L1 comprising the amino acid sequence of SEQ ID NO: 9,
  (ii) HVR-L2 comprising the amino acid sequence of SEQ ID NO: 10,
  (iii) HVR-L3 comprising the amino acid sequence of SEQ ID NO: 11,
  (iv) HVR-H1 comprising the amino acid sequence of SEQ ID NO: 12,
  (v) HVR-H2 comprising the amino acid sequence of SEQ ID NO: 13, and
  (vi) HVR-H3 comprising the amino acid sequence of SEQ ID NO: 14, and the other of the first and second half antibodies comprises
  (i) HVR-L1 comprising the amino acid sequence of SEQ ID NO: 23,
  (ii) HVR-L2 comprising the amino acid sequence of SEQ ID NO: 24,
  (iii) HVR-L3 comprising the amino acid sequence of SEQ ID NO: 25,
  (iv) HVR-H1 comprising the amino acid sequence of SEQ ID NO: 26,
  (v) HVR-H2 comprising the amino acid sequence of SEQ ID NO: 27, and
  (vi) HVR-H3 comprising the amino acid sequence of SEQ ID NO: 28.

In some embodiments, one of the first and second half antibodies comprises
- (i) HVR-L1 comprising the amino acid sequence of SEQ ID NO: 9,
- (ii) HVR-L2 comprising the amino acid sequence of SEQ ID NO: 10,
- (iii) HVR-L3 comprising the amino acid sequence of SEQ ID NO: 11,
- (iv) HVR-H1 comprising the amino acid sequence of SEQ ID NO: 12,
- (v) HVR-H2 comprising the amino acid sequence of SEQ ID NO: 13, and
- (vi) HVR-H3 comprising the amino acid sequence of SEQ ID NO: 14, and the other of the first and second half antibodies comprises
- (i) HVR-L1 comprising the amino acid sequence of SEQ ID NO: 37,
- (ii) HVR-L2 comprising the amino acid sequence of SEQ ID NO: 38,
- (iii) HVR-L3 comprising the amino acid sequence of SEQ ID NO: 39,
- (iv) HVR-H1 comprising the amino acid sequence of SEQ ID NO: 40,
- (v) HVR-H2 comprising the amino acid sequence of SEQ ID NO: 41, and
- (vi) HVR-H3 comprising the amino acid sequence of SEQ ID NO: 42.

In some embodiments, one of the first and second half antibodies comprises
- (i) HVR-L1 comprising the amino acid sequence of SEQ ID NO: 9,
- (ii) HVR-L2 comprising the amino acid sequence of SEQ ID NO: 10,
- (iii) HVR-L3 comprising the amino acid sequence of SEQ ID NO: 11,
- (iv) HVR-H1 comprising the amino acid sequence of SEQ ID NO: 12,
- (v) HVR-H2 comprising the amino acid sequence of SEQ ID NO: 13, and
- (vi) HVR-H3 comprising the amino acid sequence of SEQ ID NO: 14, and the other of the first and second half antibodies comprises
- (i) HVR-L1 comprising the amino acid sequence of SEQ ID NO: 51,
- (ii) HVR-L2 comprising the amino acid sequence of SEQ ID NO: 52,
- (iii) HVR-L3 comprising the amino acid sequence of SEQ ID NO: 53,
- (iv) HVR-H1 comprising the amino acid sequence of SEQ ID NO: 54,
- (v) HVR-H2 comprising the amino acid sequence of SEQ ID NO: 55, and
- (vi) HVR-H3 comprising the amino acid sequence of SEQ ID NO: 56.

In some embodiments, one of the first and second half antibodies comprises
- (i) HVR-L1 comprising the amino acid sequence of SEQ ID NO: 23,
- (ii) HVR-L2 comprising the amino acid sequence of SEQ ID NO: 24,
- (iii) HVR-L3 comprising the amino acid sequence of SEQ ID NO: 25,
- (iv) HVR-H1 comprising the amino acid sequence of SEQ ID NO: 26,
- (v) HVR-H2 comprising the amino acid sequence of SEQ ID NO: 27, and
- (vi) HVR-H3 comprising the amino acid sequence of SEQ ID NO: 28, and the other of the first and second half antibodies comprises
- (i) HVR-L1 comprising the amino acid sequence of SEQ ID NO: 37,
- (ii) HVR-L2 comprising the amino acid sequence of SEQ ID NO: 38,
- (iii) HVR-L3 comprising the amino acid sequence of SEQ ID NO: 39,
- (iv) HVR-H1 comprising the amino acid sequence of SEQ ID NO: 40,
- (v) HVR-H2 comprising the amino acid sequence of SEQ ID NO: 41, and
- (vi) HVR-H3 comprising the amino acid sequence of SEQ ID NO: 42.

In some embodiments, one of the first and second half antibodies comprises
- (i) HVR-L1 comprising the amino acid sequence of SEQ ID NO: 23,
- (ii) HVR-L2 comprising the amino acid sequence of SEQ ID NO: 24,
- (iii) HVR-L3 comprising the amino acid sequence of SEQ ID NO: 25,
- (iv) HVR-H1 comprising the amino acid sequence of SEQ ID NO: 26,
- (v) HVR-H2 comprising the amino acid sequence of SEQ ID NO: 27, and
- (vi) HVR-H3 comprising the amino acid sequence of SEQ ID NO: 28, and the other of the first and second half antibodies comprises
- (i) HVR-L1 comprising the amino acid sequence of SEQ ID NO: 51,
- (ii) HVR-L2 comprising the amino acid sequence of SEQ ID NO: 52,
- (iii) HVR-L3 comprising the amino acid sequence of SEQ ID NO: 53,
- (iv) HVR-H1 comprising the amino acid sequence of SEQ ID NO: 54,
- (v) HVR-H2 comprising the amino acid sequence of SEQ ID NO: 55, and
- (vi) HVR-H3 comprising the amino acid sequence of SEQ ID NO: 56.

In some embodiments, one of the first and second half antibodies comprises
- (i) HVR-L1 comprising the amino acid sequence of SEQ ID NO: 37,
- (ii) HVR-L2 comprising the amino acid sequence of SEQ ID NO: 38,
- (iii) HVR-L3 comprising the amino acid sequence of SEQ ID NO: 39,
- (iv) HVR-H1 comprising the amino acid sequence of SEQ ID NO: 40,
- (v) HVR-H2 comprising the amino acid sequence of SEQ ID NO: 41, and
- (vi) HVR-H3 comprising the amino acid sequence of SEQ ID NO: 42, and the other of the first and second half antibodies comprises
- (i) HVR-L1 comprising the amino acid sequence of SEQ ID NO: 51,
- (ii) HVR-L2 comprising the amino acid sequence of SEQ ID NO: 52,
- (iii) HVR-L3 comprising the amino acid sequence of SEQ ID NO: 53,
- (iv) HVR-H1 comprising the amino acid sequence of SEQ ID NO: 54,
- (v) HVR-H2 comprising the amino acid sequence of SEQ ID NO: 55, and (vi) HVR-H3 comprising the amino acid sequence of SEQ ID NO: 56.

In some embodiments, the first or second half antibody comprises a VL sequence with at least about 90%, 91%, 92%, 93%, 94%, 95%, 96%, 97%, 98%, 99%, or 100% sequence identity to SEQ ID NO: 7 and a VH sequence with at least about 90%, 91%, 92%, 93%, 94%, 95%, 96%, 97%, 98%, 99%, or 100% sequence identity to SEQ ID NO: 8. In some embodiments, the first or second half antibody comprises a VL sequence with at least about 90%, 91%, 92%, 93%, 94%, 95%, 96%, 97%, 98%, 99%, or 100% sequence identity to SEQ ID NO: 21 and a VH sequence with at least about 90%, 91%, 92%, 93%, 94%, 95%, 96%, 97%, 98%, 99%, or 100% sequence identity to SEQ ID NO: 22. In some embodiments, the first or second half antibody comprises a VL sequence with at least about 90%, 91%, 92%, 93%, 94%, 95%, 96%, 97%, 98%, 99%, or 100% sequence identity to SEQ ID NO: 35 and a VH sequence with at least about 90%, 91%, 92%, 93%, 94%, 95%, 96%, 97%, 98%, 99%, or 100% sequence identity to SEQ ID NO: 36. In some embodiments, the first or second half antibody comprises a VL sequence with at least about 90%, 91%, 92%, 93%, 94%, 95%, 96%, 97%, 98%, 99%, or 100% sequence identity to SEQ ID NO: 49 and a VH sequence with at least about 90%, 91%, 92%, 93%, 94%, 95%, 96%, 97%, 98%, 99%, or 100% sequence identity to SEQ ID NO: 50.

Unless otherwise indicated, at least one of the VL and VH sequences of the second half antibody is not identical to its counterpart in the first half antibody. In some embodiments, the VL sequence of the second half antibody is not identical to the VL sequence of the first half antibody. In some embodiments, the VH sequence of the second half antibody is not identical to the VH sequence of the first half antibody. In some embodiments, the VL and VH sequences of the second half antibody are not identical to the VL and VH sequences of the first half antibody.

In some embodiments, a) one of the first and second half antibodies comprises a VL sequence with at least about 90%, 91%, 92%, 93%, 94%, 95%, 96%, 97%, 98%, 99%, or 100% sequence identity to SEQ ID NO: 7 and a VH sequence with at least about 90%, 91%, 92%, 93%, 94%, 95%, 96%, 97%, 98%, 99%, or 100% sequence identity to SEQ ID NO: 8, and the other of the first and second half antibodies comprises a VL sequence with at least about 90%, 91%, 92%, 93%, 94%, 95%, 96%, 97%, 98%, 99%, or 100% sequence identity to SEQ ID NO: 21 and a VH sequence with at least about 90%, 91%, 92%, 93%, 94%, 95%, 96%, 97%, 98%, 99%, or 100% sequence identity to SEQ ID NO: 22. In some embodiments, one of the first and second half antibodies comprises a VL sequence with at least about 90%, 91%, 92%, 93%, 94%, 95%, 96%, 97%, 98%, 99%, or 100% sequence identity to SEQ ID NO: 7 and a VH sequence with at least about 90%, 91%, 92%, 93%, 94%, 95%, 96%, 97%, 98%, 99%, or 100% sequence identity to SEQ ID NO: 8, and the other of the first and second half antibodies comprises a VL sequence with at least about 90%, 91%, 92%, 93%, 94%, 95%, 96%, 97%, 98%, 99%, or 100% sequence identity to SEQ ID NO: 35 and a VH sequence with at least about 90%, 91%, 92%, 93%, 94%, 95%, 96%, 97%, 98%, 99%, or 100% sequence identity to SEQ ID NO: 36. In some embodiments, one of the first and second half antibodies comprises a VL sequence with at least about 90%, 91%, 92%, 93%, 94%, 95%, 96%, 97%, 98%, 99%, or 100% sequence identity to SEQ ID NO: 7 and a VH sequence with at least about 90%, 91%, 92%, 93%, 94%, 95%, 96%, 97%, 98%, 99%, or 100% sequence identity to SEQ ID NO: 8, and the other of the first and second half antibodies comprises a VL sequence with at least about 90%, 91%, 92%, 93%, 94%, 95%, 96%, 97%, 98%, 99%, or 100% sequence identity to SEQ ID NO: 49 and a VH sequence with at least about 90%, 91%, 92%, 93%, 94%, 95%, 96%, 97%, 98%, 99%, or 100% sequence identity to SEQ ID NO: 50. In some embodiments, one of the first and second half antibodies comprises a VL sequence with at least about 90%, 91%, 92%, 93%, 94%, 95%, 96%, 97%, 98%, 99%, or 100% sequence identity to SEQ ID NO: 21 and a VH sequence with at least about 90%, 91%, 92%, 93%, 94%, 95%, 96%, 97%, 98%, 99%, or 100% sequence identity to SEQ ID NO: 22, and the other of the first and second half antibodies comprises a VL sequence with at least about 90%, 91%, 92%, 93%, 94%, 95%, 96%, 97%, 98%, 99%, or 100% sequence identity to SEQ ID NO: 35 and a VH sequence with at least about 90%, 91%, 92%, 93%, 94%, 95%, 96%, 97%, 98%, 99%, or 100% sequence identity to SEQ ID NO: 36. In some embodiments, one of the first and second half antibodies comprises a VL sequence with at least about 90%, 91%, 92%, 93%, 94%, 95%, 96%, 97%, 98%, 99%, or 100% sequence identity to SEQ ID NO: 21 and a VH sequence with at least about 90%, 91%, 92%, 93%, 94%, 95%, 96%, 97%, 98%, 99%, or 100% sequence identity to SEQ ID NO: 22, and the other of the first and second half antibodies comprises a VL sequence with at least about 90%, 91%, 92%, 93%, 94%, 95%, 96%, 97%, 98%, 99%, or 100% sequence identity to SEQ ID NO: 49 and a VH sequence with at least about 90%, 91%, 92%, 93%, 94%, 95%, 96%, 97%, 98%, 99%, or 100% sequence identity to SEQ ID NO: 50. In some embodiments, one of the first and second half antibodies comprises a VL sequence with at least about 90%, 91%, 92%, 93%, 94%, 95%, 96%, 97%, 98%, 99%, or 100% sequence identity to SEQ ID NO: 35 and a VH sequence with at least about 90%, 91%, 92%, 93%, 94%, 95%, 96%, 97%, 98%, 99%, or 100% sequence identity to SEQ ID NO: 36, and the other of the first and second half antibodies comprises a VL sequence with at least about 90%, 91%, 92%, 93%, 94%, 95%, 96%, 97%, 98%, 99%, or 100% sequence identity to SEQ ID NO: 49 and a VH sequence with at least about 90%, 91%, 92%, 93%, 94%, 95%, 96%, 97%, 98%, 99%, or 100% sequence identity to SEQ ID NO: 50.

In some embodiments, the first or second half antibody comprises VH and VL sequences at least about 90%, 91%, 92%, 93%, 94%, 95%, 96%, 97%, 98%, 99%, or 100% identical to the VH and VL sequences of an antibody disclosed in U.S. Pat. No. 7,763,245 that binds a polyubiquitin. In some embodiments, the first or second half antibody comprises a combination of VH and VL sequences disclosed in U.S. Pat. No. 7,763,245, wherein the half antibody binds a polyubiquitin.

In some embodiments, the first or second half antibody comprises VH and VL sequences at least about 90%, 91%, 92%, 93%, 94%, 95%, 96%, 97%, 98%, 99%, or 100% identical to the VH and VL sequences of an antibody disclosed in U.S. Pat. No. 8,133,488 that binds a polyubiquitin. In some embodiments, the first or second half antibody comprises a combination of VH and VL sequences disclosed in U.S. Pat. No. 8,133,488, wherein the half antibody binds a polyubiquitin.

In some embodiments, the first or second half antibody comprises VH and VL sequences at least about 90%, 91%, 92%, 93%, 94%, 95%, 96%, 97%, 98%, 99%, or 100% identical to the VH and VL sequences of an antibody disclosed in U.S. Pat. No. 8,992,919 that binds a polyubiquitin. In some embodiments, the first or second half antibody comprises a combination of VH and VL sequences disclosed in U.S. Pat. No. 8,992,919, wherein the half antibody binds a polyubiquitin.

In some embodiments, the first or second half antibody comprises VH and VL sequences at least about 90%, 91%, 92%, 93%, 94%, 95%, 96%, 97%, 98%, 99%, or 100% identical to the VH and VL sequences of an antibody disclosed in U.S. Pat. No. 9,321,844 that binds a polyubiquitin. In some embodiments, the first or second half antibody comprises a combination of VH and VL sequences disclosed in U.S. Pat. No. 9,321,844, wherein the half antibody binds a polyubiquitin.

In some embodiments, the first or second half antibody comprises the VH and VL sequences of an antibody disclosed in U.S. Pat. No. 7,763,245 that binds a polyubiquitin. In some embodiments, the first or second half antibody comprises a combination of VH and VL sequences disclosed in U.S. Pat. No. 7,763,245, wherein the half antibody binds a polyubiquitin.

In some embodiments, the first or second half antibody comprises the VH and VL sequences of an antibody disclosed in U.S. Pat. No. 8,133,488 that binds a polyubiquitin. In some embodiments, the first or second half antibody comprises a combination of VH and VL sequences disclosed in U.S. Pat. No. 8,133,488, wherein the half antibody binds a polyubiquitin.

In some embodiments, the first or second half antibody comprises the VH and VL sequences of an antibody disclosed in U.S. Pat. No. 8,992,919 that binds a polyubiquitin. In some embodiments, the first or second half antibody comprises a combination of VH and VL sequences disclosed in U.S. Pat. No. 8,992,919, wherein the half antibody binds a polyubiquitin.

In some embodiments, the first or second half antibody comprises the VH and VL sequences of an antibody disclosed in U.S. Pat. No. 9,321,844 that binds a polyubiquitin. In some embodiments, the first or second half antibody comprises a combination of VH and VL sequences disclosed in U.S. Pat. No. 9,321,844, wherein the half antibody binds a polyubiquitin.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody comprising that sequence retains the ability to bind to a polyubiquitin. In certain embodiments, a total of 1 to 10 amino acids have been substituted, inserted and/or deleted in a VH sequence. In certain embodiments, substitutions, insertions, or deletions occur in regions outside the HVRs (i.e., in the FRs). Optionally, the antibody comprises a VH sequence discussed above, including post-translational modifications of that sequence.

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody comprising that sequence retains the ability to bind to a polyubiquitin. In certain embodiments, a total of 1 to 10 amino acids have been substituted, inserted and/or deleted in a VL sequence. In certain embodiments, substitutions, insertions, or deletions occur in regions outside the HVRs (i.e., in the FRs). Optionally, the antibody comprises a VL sequence discussed above, including post-translational modifications of that sequence.

In some embodiments, the antibody is humanized. In some embodiments, the antibody comprises HVRs as in any of the above embodiments, and further comprises a human acceptor framework, e.g. a human immunoglobulin framework or a human consensus framework. In some embodiments, the antibody comprises HVRs as in any of the above embodiments and rabbit framework regions.

In some aspects, an antibody that binds to the same epitopes as a bispecific antibody provided herein is provided. For example, in certain embodiments, an antibody is provided that binds to the same epitopes as an antibody comprising first and second half antibodies, wherein:

a) one of the first and second half antibodies comprises a VL sequence of SEQ ID NO: 7 and a VH sequence of SEQ ID NO: 8,
and the other of the first and second half antibodies comprises a VL sequence of SEQ ID NO: 21 and a VH sequence of SEQ ID NO: 22;

b) one of the first and second half antibodies comprises a VL sequence of SEQ ID NO: 7 and a VH sequence of SEQ ID NO: 8,
and the other of the first and second half antibodies comprises a VL sequence of SEQ ID NO: 35 and a VH sequence of SEQ ID NO: 36;

c) one of the first and second half antibodies comprises a VL sequence of SEQ ID NO: 7 and a VH sequence of SEQ ID NO: 8,
and the other of the first and second half antibodies comprises a VL sequence of SEQ ID NO: 49 and a VH sequence of SEQ ID NO: 50;

d) one of the first and second half antibodies comprises a VL sequence of SEQ ID NO: 21 and a VH sequence of SEQ ID NO: 22,
and the other of the first and second half antibodies comprises a VL sequence of SEQ ID NO: 35 and a VH sequence of SEQ ID NO: 36;

e) one of the first and second half antibodies comprises a VL sequence of SEQ ID NO: 21 and a VH sequence of SEQ ID NO: 22,
and the other of the first and second half antibodies comprises a VL sequence of SEQ ID NO: 49 and a VH sequence of SEQ ID NO: 50; or f) one of the first and second half antibodies comprises a VL sequence of SEQ ID NO: 35 and a VH sequence of SEQ ID NO: 36,
and the other of the first and second half antibodies comprises a VL sequence of SEQ ID NO: 49 and a VH sequence of SEQ ID NO: 50.

In some embodiments, an antibody that competes for binding to a mixed-topology polyubiquitin with a bispecific antibody comprising VH and VL sequences as in one of a) through f) in the preceding paragraph is provided.

In some embodiments, the antibody is a monoclonal antibody, including a chimeric, humanized or human antibody. In some embodiments, the antibody is an antibody fragment, e.g., a dimeric scFv, diabody, or F(ab')$_2$ fragment. In another embodiment, the antibody is a substantially full length antibody, e.g., an IgG1, IgG2a, IgG2b, IgG3, or IgG4 antibody, or other antibody class or isotype as defined herein.

In some embodiments, the antibody comprises at least one heavy chain with a C-terminal lysine. In some embodiments, the antibody comprises at least one heavy chain lacking a C-terminal lysine. In some embodiments, the antibody comprises only heavy chains without a C-terminal lysine. C-terminal lysines can be removed, e.g., enzymatically, such as by carboxypeptidase treatment, or genetically, such as by deletion or substitution of the lysine codon at the 3' end of a heavy chain coding sequence. Heavy chain C-terminal lysines are located far from antigen binding sites and dispensable for binding activity, and their removal can provide more homogeneous antibody preparations.

In some embodiments, the antibody comprises first and second half antibodies, wherein the first or second half antibody comprises
- a) a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 4;
- b) a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 18;
- c) a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 32; or
- d) a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 46, optionally wherein a C-terminal lysine is missing from one or more heavy chains.

In some embodiments, the antibody comprises first and second half antibodies, wherein the first or second half antibody comprises
- a) a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 6;
- b) a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 20;
- c) a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 34; or
- d) a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 48, optionally wherein a C-terminal lysine is missing from one or more chains.

In some embodiments, the antibody comprises first and second half antibodies, wherein
- a) one of the first and second half antibodies comprises a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 4, and the other of the first and second half antibodies comprises a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 20;

- b) one of the first and second half antibodies comprises a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 4, and the other of the first and second half antibodies comprises a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 34;

- c) one of the first and second half antibodies comprises a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 4, and the other of the first and second half antibodies comprises a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 48;

- d) one of the first and second half antibodies comprises a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 6, and the other of the first and second half antibodies comprises a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 18;

- e) one of the first and second half antibodies comprises a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 6, and the other of the first and second half antibodies comprises a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 32;

f) one of the first and second half antibodies comprises a light chain sequence having at least about 90%, 91%, 92%, 93%, 94%, 95%, 96%, 97%, 98%, 99%, or 100% sequence identity to SEQ ID NO: 2 and a heavy chain sequence having at least about 90%, 91%, 92%, 93%, 94%, 95%, 96%, 97%, 98%, 99%, or 100% sequence identity to SEQ ID NO: 6, and the other of the first and second half antibodies comprises a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 46;

g) one of the first and second half antibodies comprises a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 18, and the other of the first and second half antibodies comprises a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 34;

h) one of the first and second half antibodies comprises a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 18, and the other of the first and second half antibodies comprises a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 48;

i) one of the first and second half antibodies comprises a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 32, and the other of the first and second half antibodies comprises a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 48;

j) one of the first and second half antibodies comprises a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 20, and the other of the first and second half antibodies comprises a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 32;

k) one of the first and second half antibodies comprises a light chain sequence having at least about 90%, 91%, 92%, 93%, 94%, 95%, 96%, 97%, 98%, 99%, or 100% sequence identity to SEQ ID NO: 16 and a heavy chain sequence having at least about 90%, 91%, 92%, 93%, 94%, 95%, 96%, 97%, 98%, 99%, or 100% sequence identity to SEQ ID NO: 20, and the other of the first and second half antibodies comprises a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 46; or l) one of the first and second half antibodies comprises a light chain sequence having at least about 90%, 91%, 92%, 93%, 94%, 95%, 96%, 97%, 98%, 99%, or 100% sequence identity to SEQ ID NO: 30 and a heavy chain sequence having at least about 90%, 91%, 92%, 93%, 94%, 95%, 96%, 97%, 98%, 99%, or 100% sequence identity to SEQ ID NO: 34, and the other of the first and second half antibodies comprises a light chain sequence having at least about 90%, 91%, 92%, 93%, 94%, 95%, 96%, 97%, 98%, 99%, or 100% sequence identity to SEQ ID NO: 44 and a heavy chain sequence having at least about 90%, 91%, 92%, 93%, 94%, 95%, 96%, 97%, 98%, 99%, or 100% sequence identity to SEQ ID NO: 46, optionally wherein a C-terminal lysine is missing from one or more chains.

In some embodiments, the antibody comprises first and second half antibodies, wherein the first half antibody comprises a light chain sequence of SEQ ID NO: 2 and a heavy chain sequence of SEQ ID NO: 4, and the second half antibody comprises a light chain sequence of SEQ ID NO: 16 and a heavy chain sequence of SEQ ID NO: 20, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 4, and the second half antibody comprises a light chain sequence of SEQ ID NO: 30 and a heavy chain sequence of SEQ ID NO: 34, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 4, and the second half antibody comprises a light chain sequence of SEQ ID NO: 44 and a heavy chain sequence of SEQ ID NO: 48, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 6, and the second half antibody comprises a light chain sequence of SEQ ID NO: 16 and a heavy chain sequence of SEQ ID NO: 18, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 6, and the second half antibody comprises a light chain sequence of SEQ ID NO: 30 and a heavy chain sequence of SEQ ID NO: 32, and optionally wherein a C-terminal lysine is missing from one or more heavy chains.

In some embodiments, the antibody comprises first and second half antibodies, wherein the first half antibody comprises a light chain sequence of SEQ ID NO: 2 and a heavy chain sequence of SEQ ID NO: 6, and the second half antibody comprises a light chain sequence of SEQ ID NO: 44 and a heavy chain sequence of SEQ ID NO: 46, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 18, and the second half antibody comprises a light chain sequence of SEQ ID NO: 30 and a heavy chain sequence of SEQ ID NO: 34, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 18, and the second half antibody comprises a light chain sequence of SEQ ID NO: 44 and a heavy chain sequence of SEQ ID NO: 48, and optionally wherein a C-terminal lysine is missing from one or more heavy chains.

In some embodiments, the antibody comprises first and second half antibodies, wherein the first half antibody comprises a light chain sequence of SEQ ID NO: 30 and a heavy chain sequence of SEQ ID NO: 32, and the second half antibody comprises a light chain sequence of SEQ ID NO: 44 and a heavy chain sequence of SEQ ID NO: 48, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 20, and the second half antibody comprises a light chain sequence of SEQ ID NO: 30 and a heavy chain sequence of SEQ ID NO: 32, and optionally wherein a C-terminal lysine is missing from one or more heavy chains.

In some embodiments, the antibody comprises first and second half antibodies, wherein the first half antibody comprises a light chain sequence of SEQ ID NO: 16 and a heavy chain sequence of SEQ ID NO: 20, and the second half antibody comprises a light chain sequence of SEQ ID NO: 44 and a heavy chain sequence of SEQ ID NO: 46, and optionally wherein a C-terminal lysine is missing from one or more heavy chains.

In some embodiments, the antibody comprises first and second half antibodies, wherein the first half antibody comprises a light chain sequence of SEQ ID NO: 30 and a heavy chain sequence of SEQ ID NO: 34, and the second half antibody comprises a light chain sequence of SEQ ID NO: 44 and a heavy chain sequence of SEQ ID NO: 46, and optionally wherein a C-terminal lysine is missing from one or more heavy chains.

In a further aspect, an antibody according to any of the above embodiments may incorporate any of the features, singly or in combination, as described in Sections 1-7 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM, and optionally is ≥$10^{-13}$ M. (e.g. $10^{-8}$M or less, e.g. from $10^{-8}$ M to $10^{-13}$ M, e.g., from $10^{-9}$ M to $10^{-13}$ M).

In some embodiments, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN® 20) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In some embodiments, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN® 20) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, F(ab')$_2$ fragments, dimeric single chain Fv, and other fragments described below. For a review of certain antibody fragments, see Hudson et al. *Nat. Med* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

In some embodiments, the antibody is a diabody. Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl Acad. Sci. USA* 90: 6444-6448 (1993).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In some embodiments, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall' Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, Methods and *Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004), Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). In some embodiments, the antibody comprises first and second half antibodies, wherein the first half antibody comprises a first heavy chain constant region comprising a knob mutation and the second heavy chain comprises a second heavy chain constant region comprising a hole mutation; or wherein the first half antibody comprises a first heavy chain constant region comprising a hole mutation and the second heavy chain comprises a second heavy chain constant region comprising a knob mutation. In some embodiments, the antibody is an IgG1 antibody and the knob mutation comprises a T366W mutation. In some embodiments, the antibody is an IgG1 antibody and the hole mutation comprises at least one, at least two, or three mutations selected from T366S, L368A, and Y407V. In some embodiments, the antibody is an IgG4 antibody and the knob mutation comprises a T366W mutation. In some embodiments, the antibody is an IgG4 antibody and the hole mutation comprises at least one, at least two, or three mutations selected from T366S, L368A, and Y407V mutations. The foregoing numbering of the positions of mutation(s) is EU numbering. The actual position(s) of the mutation(s) in a heavy chain sequence may vary, e.g., depending on the length of the preceding variable region, such as by up to 10 positions.

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J Immunol.* 147: 60 (1991). In some embodiments, the antibody is a diabody. Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993).

Triabodies and tetrabodies are described in Hudson et al., *Nat. Med.* 9:129-134 (2003). In some embodiments, the antibody is a triabody. In some embodiments, the triabody comprises a first antigen recognition site, a second antigen recognition site, and a third antigen recognition site, wherein at least one of the antigen recognition sites differs from the other antigen recognition sites. In some embodiments, the triabody comprises first, second, and third antigen recognition sites that bind three different polyubiquitins. In some embodiments, the triabody comprises first, second, and third antigen recognition sites that bind any three polyubiquitins selected from a K11-linked polyubiquitin, a K48-linked polyubiquitin, a K63-linked polyubiquitin, and a C-terminal to N-terminal-linked polyubiquitin. Each antigen recognition site can comprise a combination of HVRs or of a VL and VH discussed above.

In some embodiments, the antibody is a tetrabody. In some embodiments, the tetrabody comprises a first antigen recognition site, a second antigen recognition site, a third antigen recognition site, and a fourth antigen recognition site, wherein at least one or at least two of the antigen recognition sites differ from the other antigen recognition sites. In some embodiments, the tetrabody comprises first, second, and third antigen recognition sites that bind three different polyubiquitins. In some embodiments, the tetrabody comprises first, second, and third antigen recognition sites that bind any three polyubiquitins selected from a K11-linked polyubiquitin, a K48-linked polyubiquitin, a K63-linked polyubiquitin, and a C-terminal to N-terminal-linked polyubiquitin. In some embodiments, the tetrabody comprises first, second, third, and fourth antigen recognition sites that bind four different polyubiquitins. In some embodiments, the tetrabody comprises first, second, third, and fourth antigen recognition sites that bind a K11-linked polyubiquitin, a K48-linked polyubiquitin, a K63-linked polyubiquitin, and a C-terminal to N-terminal-linked polyubiquitin. Each antigen recognition site can comprise a combination of HVRs or a combination of a VL and VH discussed above.

Engineered antibodies with three or more functional antigen binding sites, including "Octopus antibodies," are also included herein (see, e.g. US 2006/0025576A1). The term octopus antibody is used in the sense of those discussed in US 2006/0025576A1 and is not meant to refer to an antibody produced by or obtained from an octopus.

The antibody or fragment herein also includes a "Dual Acting FAb" or "DAF" comprising two antigen binding sites that binds two different antigens (see, US 2008/0069820, for example). For example, the two different antigens can be any of the polyubiquitins discussed above, such as K11-, K48-, K63-, or C-terminal to N-terminal-linked polyubiquitins.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |

TABLE 1-continued

| Original Residue | Exemplary Substitutions | Preferred Substitutions |
| --- | --- | --- |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, an antibody variant possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad Sci. USA* 83:7059-7063 (1986)) and Hellstrom, I et al., *Proc.*

Nat'l Acad. Sci. USA 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fe mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; K149 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In some embodiments, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In some such embodiments, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an antibody disclosed herein is provided, wherein the method comprises culturing a host cell comprising a nucleic acid encoding the antibody, as provided above, under conditions suitable for expression of the antibody, and optionally recovering the antibody from the host cell (or host cell culture medium).

In some embodiments, components of a multispecific antibody (e.g., a first half antibody and second half antibody) are expressed in separate cells or cell cultures and then combined in vitro. In other embodiments, all components of a multispecific antibody are expressed in the same cell or cell culture.

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, NJ), pp. 255-268 (2003).

C. Assays

Antibodies provided herein may be identified, screened for, or characterized for their physical/chemical properties and/or biological activities by various assays known in the art.

In some aspects, an antibody is tested for its antigen binding activity, e.g., by known methods such as ELISA, FACS or Western blot.

In another aspect, competition assays may be used to identify an antibody that competes with any of the antibodies described herein for binding to a mixed-topology polyubiquitin. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized mixed-topology polyubiquitin is incubated with a solution comprising a first labeled antibody that binds thereto (e.g., any of the antibodies described herein) and a second unlabeled antibody that is being tested for its ability to compete with the first antibody for binding to the mixed-topology polyubiquitin. The second antibody may be present in a hybridoma supernatant. As a control, mixed-topology polyubiquitin is incubated in a solution comprising the first labeled antibody but not the second unlabeled antibody. After incubation under conditions permissive for binding of the first antibody to mixed-topology polyubiquitin, excess unbound antibody is removed, and the amount of label associated with immobilized mixed-topology polyubiquitin is measured. If the amount of label associated with immobilized mixed-topology polyubiquitin is substantially reduced in the test sample relative to the control sample, then that indicates that the second antibody is competing with the first antibody for binding to the mixed-topology polyubiquitin. See Harlow and Lane (1988) *Antibodies: A Laboratory Manual* ch. 14 (Cold Spring Harbor Laboratory, Cold Spring Harbor, NY).

D. Immunoconjugates

Immunoconjugates comprising an antibody disclosed herein conjugated to one or more cytotoxic agents are provided, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor or other diseased cell or tissue, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) may selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, *vinca* alkaloid, taxane, trichothecene, CC1065, camptothecin, elinafide, and stereoisomers, isosteres, analogs, and derivatives thereof that have cytotoxic activity.

E. Methods and Compositions for Diagnostics and Detection

In certain embodiments, any of the antibodies provided herein is useful for detecting the presence of mixed-topology polyubiquitin in a biological sample. The term "detecting" as used herein encompasses quantitative or qualitative detection. A "biological sample" comprises, e.g., a cell or tissue (e.g., biopsy material, including cancerous or potentially cancerous colon, colorectal, small intestine, endometrial, pancreatic, breast, lung, prostate, or ovarian tissue).

In some embodiments, an antibody disclosed herein is for use in a method of diagnosis or detection. In a further aspect, a method of detecting the presence of mixed-topology polyubiquitin in a biological sample is provided. In certain embodiments, the method comprises contacting the biological sample with an antibody as described herein under conditions permissive for binding of the antibody to mixed-topology polyubiquitin, and detecting whether a complex is formed between the antibody and mixed-topology polyubiquitin in the biological sample. Such method may be an in vitro or in vivo method. In some embodiments, an antibody is used to select subjects eligible for therapy with an anti-mixed-topology polyubiquitin antibody, e.g. where mixed-topology polyubiquitin is a biomarker for selection of patients. In some embodiments, the biological sample is a cell or tissue (e.g., biopsy material, including cancerous or potentially cancerous tissue).

In some embodiments, a method of detecting a polyubiquitinated protein in a biological sample, the polyubiquitinated protein being polyubiquitinated at two or more positions with at least first and second polyubiquitins, with the first and second polyubiquitins having different linkages, is provided. In certain embodiments, the method comprises contacting the biological sample with an antibody as described herein under conditions permissive for binding of the antibody to the polyubiquitinated protein, and detecting whether a complex is formed between the antibody and the polyubiquitinated protein in the biological sample. Such method may be an in vitro or in vivo method. In some embodiments, an antibody is used to select subjects eligible for therapy with an antibody disclosed herein, e.g. where the polyubiquitinated protein polyubiquitinated at two or more positions with at least first and second polyubiquitins having different linkages is a biomarker for selection of patients. In some embodiments, the biological sample is a cell or tissue (e.g., biopsy material, including cancerous or potentially cancerous tissue).

In a further embodiment, an antibody disclosed herein is used in vivo to detect, e.g., by in vivo imaging, mixed-topology polyubiquitin or a polyubiquitinated protein polyubiquitinated at two or more positions with at least first and second polyubiquitins having different linkages in a subject, e.g., for the purposes of diagnosing, prognosing, or staging a disease, determining the appropriate course of therapy, or monitoring response to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a mixed-topology polyubiquitin in a subject, the method comprising administering a labeled antibody to a subject, and detecting the labeled anti-mixed-topology polyubiquitin antibody in the subject. In certain of such embodiments, the labeled antibody comprises (e.g., is conjugated to) a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr. Non-limiting exemplary methods of making and using $^{89}$Zr-labeled antibodies are described, e.g., in PCT Publication No. WO 2011/056983. In some embodiments, the labeled antibody is a cysteine engineered antibody conjugated to one or more zirconium complexes. See, e.g., WO 2011/056983.

In further embodiments, a method of diagnosis or detection comprises contacting a first antibody disclosed herein which is immobilized to a substrate with a biological sample to be tested for the presence of mixed-topology polyubiquitin or a polyubiquitinated protein polyubiquitinated at two or more positions with at least first and second polyubiquitins having different linkages, exposing the substrate to a second antibody that binds mixed-topology polyubiquitin or the polyubiquitinated protein, and detecting whether the second antibody is bound to a complex between the first antibody and mixed-topology polyubiquitin or the polyubiquitinated protein in the biological sample (sometimes referred to as a sandwich assay). A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous colon, colorectal, small intestine, endometrial, pancreatic or ovarian tissue). In certain embodiments, the first or second antibody is any of the antibodies described herein.

In certain embodiments, the antibodies disclosed herein are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^3$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

Presence of mixed-topology polyubiquitin or a polyubiquitinated protein polyubiquitinated at two or more positions with at least first and second polyubiquitins having different linkages in a sample can be analyzed by a number of methodologies using an antibody disclosed herein, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), quantitative blood based assays (as for example Serum ELISA. Typical protocols for evaluating the status of proteins are found, for example in Ausubel et al., eds., 1995, Current Protocols In Molecular Biology, Unit 15 (Immunoblotting). Multiplexed immunoassays such as those available from Rules Based Medicine or Meso Scale Discovery ("MSD") may also be used.

In some embodiments, a composition is provided that is substantially free of monospecific antibodies, unassembled half antibodies, or both monospecific antibodies and unassembled half antibodies. Monospecific antibodies are antibodies that do not comprise more than one type of antigen recognition site, e.g., antibodies with only one set of six CDRs or antibodies in which each set of six CDRs is identical. Antibodies in which a first set of CDRs vanes only slightly from any other sets of CDRs, e.g., with respect to a small number of amino acid residues, wherein the differences do not result in preferential binding to a different antigen, are also considered monospecific. An unassembled half antibody is not stably associated (covalently or noncovalently) with another half antibody, e.g., appears as a single heavy/light chain unit when analyzed by an appropriate technique, such as size exclusion chromatography, mass spectrometry, or electrophoresis.

F. Pharmaceutical Formulations

Pharmaceutical formulations of an antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In some aspects, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the antibodies or immunoconjugates provided herein may be used in methods, e.g., therapeutic methods.

In another aspect, an antibody or immunoconjugate disclosed herein for use as a medicament is provided. In further aspects, an antibody or immunoconjugate disclosed herein for use in a method of treatment is provided. In certain embodiments, an antibody or immunoconjugate disclosed herein for use in treating mixed-topology polyubiquitin-positive cancer is provided.

In a further aspect, the use of an antibody or immunoconjugate disclosed herein in the manufacture or preparation of a medicament is provided.

An "individual" according to any of the above embodiments may be a human.

In a further aspect, pharmaceutical formulations are provided, comprising any of the antibodies or immunoconjugate provided herein, e.g., for use in any of the above therapeutic methods. In some embodiments, a pharmaceutical formulation comprises any of the antibodies or immunoconjugates provided herein and a pharmaceutically acceptable carrier.

Antibodies or immunoconjugates provided herein can be used either alone or in combination with other agents in a therapy. For instance, an antibody or immunoconjugate provided herein may be co-administered with at least one additional therapeutic agent.

Such combination therapies noted above encompass combined administration (where two or more therapeutic agents are included in the same or separate formulations), and separate administration, in which case, administration of the antibody or immunoconjugate provided herein can occur prior to, simultaneously, and/or following, administration of the additional therapeutic agent and/or adjuvant.

An antibody or immunoconjugate (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments.

It is understood that any of the above formulations or therapeutic methods may be carried out using both an immunoconjugate and an antibody.

H. Articles of Manufacture

In another aspect, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate disclosed herein. The label or package insert indicates that the composition is used for treating the condition of choice. Moreover, the article of manufacture may comprise (a) a first container with a composition contained therein, wherein the composition comprises an antibody or immunoconjugate; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions provided herein. It is understood that various other embodiments may be practiced, given the general description provided above.

A. Analytical Methods

Size Exclusion Chromatography—Multi-Angle Light Scattering. 50 µg of antibody was injected onto a 3.5 µm, 7.8 mm×300 mm XBridge Protein BEH analytical SEC 200 Å column (Waters) at 1 mL/min using an Agilent 1260 Infinity HPLC with 20 mM histidine acetate, 300 mM NaCl, pH 5.5 as the mobile phase. Proteins eluted from the analytical SEC column were directly injected onto a Wyatt DAWN® HELEOS® II/Optilab® T-rEX™ multi-angle light scattering detector to measure molar mass and polydispersity.

Mass Spectrometry. 30 µg of antibody was deglycosylated with 2 units of PNGaseF (NEB) in the presence or absence of 2 units of carboxypeptidase B (Roche) at 37° C. overnight prior to mass spectrometry analysis. 2 µg of antibody was then injected onto a 3 µm, 4.6×50 mm reverse-phase chromatography PLRP-S column (Agilent) at 1 mL/min using an Agilent 1290 Infinity UHPLC. A 0-100% buffer B gradient over 3 minutes was performed with 0.05% trifluoroacetic acid (TFA) in water (buffer A) and 0.05% TFA in acetonitrile (buffer B), followed by a 100% buffer B wash for 1 minute. Proteins eluted from the reverse-phase column were directly injected onto an Agilent 6230 electrospray ionization time-of-flight mass spectrometer (ESI-TOF) for intact mass measurement.

B. Antibody Cloning, Expression, and Annealing

Bispecific antibodies were generated using a knobs-into-holes heterodimerization approach. For a general discussion of this approach, see Merchant, A. M. et al. An efficient route to human bispecific IgG. *Nat Biotechnol* 16, 677-681, doi: 10.1038/nbt0798-677 (1998).

T366W (knob) or T366S, L368A, and Y407V (hole) mutations were introduced into the CH3 domains of anti-K11 and anti-K48 polyubiquitin linkage-specific antibodies. As a control an anti-gD antibody recognizing an irrelevant protein was used. The knob and hole mutations were chosen to allow preferential heterodimerization of the respective heavy chains of the antibodies.

The heavy chain variable domains were those of SEQ ID NO:8 (for anti-K11 polyubiquitin linkage-specificity), SEQ ID NO: 22 (for anti-K48 polyubiquitin linkage-specificity), and a non-specific anti-gD control antibody. These variable domains were subcloned into a modified pRK vector (Genentech) containing the human IgG1 heavy chain constant domains with either the knob (T366W) or hole (T366S, L368A, and Y407V) mutations in the CH3 domain.

Due to the lengths of variable regions, the actual positions of the knob and hole mutations can vary slightly, e.g., by 1 to 10 positions. For example, in SEQ ID NOs: 4 and 6, the T to W and T to S substitutions, respectively, are reflected at the $369^{th}$ rather than the $366^{th}$ amino acid residue. It is understood that references to knob and hole mutations at positions such as 366, 368, and 407 of a heavy chain are to be interpreted with adjustments, if appropriate, in light of the length of the variable region.

The light chain variable domains were similarly subcloned into a modified pRK vector (Genentech) containing the human kappa light chain constant domain. The pRK vector carries a constitutive strong signal peptide for extracellular expression in mammalian cells. The anti-K11 antibody was cloned as both knob and hole mutants (encoding heavy chains comprising SEQ ID NOs: 4 and 6, respectively), the anti-K48 was cloned as a hole mutant (encoding a heavy chain comprising SEQ ID NO: 20), and the anti-gD was cloned as a knob mutant.

The sequence table also provides a knob mutant of the anti-K11 antibody (SEQ ID NO: 18); knob and hole mutants of an anti-K63 heavy chain (SEQ ID NOs: 32 and 34, respectively); and knob and hole mutants of an anti-linear polyubiquitin heavy chain (SEQ ID NOs: 46 and 48, respectively).

To preserve the pairing of the cognate light and heavy chains we expressed either the knob or hole heavy chain mutants with their respective light chains separately in CHO cells and affinity purified them individually (FIG. 1a). Light chain and heavy chain plasmids for a given knob or hole half antibody were transiently co-transfected into CHO cells using PEI as previously described (see Wong, A. W., Baginski, T. K. & Reilly, D. E. Enhancement of DNA uptake in FUT8-deleted CHO cells for transient production of afucosylated antibodies. *Biotechnol Bioeng* 106, 751-763, doi: 10.1002/bit.22749 (2010)). Half antibodies were purified over MabSelect™ SuRe™ resin (GE Healthcare), eluted with 50 mM sodium citrate, 150 mM NaCl, pH 3.0, followed by pH adjustment to 5.0 with 10% (v/v) of 200 mM arginine, 137 mM succinate, pH 9.0.

The affinity-purified knob and hole antibodies are a mixture of monomers (half antibodies) and homodimers as seen by SDS-PAGE, analytical size-exclusion chromatography (SEC), multi-angle light scattering (MALS), and liquid chromatography-mass spectrometry (LC-MS) (FIG. 1b, 1c, 2a, 2b, Tables 2, 3), consistent with previously described knob and hole antibodies. See, e.g., Shatz, W. et al. Knobs-into-holes antibody production in mammalian cell lines reveals that asymmetric afucosylation is sufficient for full antibody-dependent cellular cytotoxicity. *MAbs* 5, 872-881, doi:10.4161/mabs.26307 (2013); Elliott, J. M. et al. Antiparallel conformation of knob and hole aglycosylated half-antibody homodimers is mediated by a CH2-CH3 hydrophobic interaction. *J Mol Biol* 426, 1947-1957, doi: 10.1016/j.jmb.2014.02.015 (2014); Spiess, C. et al. Bispecific antibodies with natural architecture produced by co-culture of bacteria expressing two distinct half-antibodies. *Nat Biotechnol* 31, 753-758, doi: 10.1038/nbt.2621 (2013). Monomer, homodimer, and heterodimer peaks are indicated in FIGS. 1c and 2a, and molecular weights were verified with light scattering (see Table 1).

The theoretical mass of the anti-K48 hole/anti-K11 knob bispecific is 144,613.19 Da, corresponding to the major peak in FIG. 1d. The predicted peak positions for the anti-K48 hole and anti-K11 knob homodimers are indicated based on their theoretical masses of 144,485.90 Da and 144,740.48 Da, respectively. Treatment with CPB results in the loss of the 144,745.26 Da peak indicating that it is not anti-K11 knob homodimer, but rather a portion of the bispecific with the carboxy-terminal lysine residue still attached. The theoretical mass of the anti-K11/gD bispecific is 145,623.14 Da and the anti-K48/gD bispecific is 145,701.11 Da, corresponding to the major peaks in the respective panels of FIG. 2c. The predicted peak positions for the anti-K11 hole homodimers, anti-K48 hole homodimers, and anti-gD knob homodimers are indicated based on their theoretical masses of 144,329.96 Da, 144,485.90, and 146,916.32 Da, respectively.

TABLE 2

Molar masses of purified half antibodies and assembled bispecifics.

|  | Peak Elution (min.) | SEC-MALS Mw (g/mol) | Polydispersity Mw/Mn |
|---|---|---|---|
| Anti-K11 knob | 7.741 | $1.472 \times 10^5$ (± 14.413%) | 1.041 (± 018.109%) |
| Anti-K11 hole | 7.314 | $1.889 \times 10^5$ (± 13.846%) | 1.103 (± 11.301%) |
|  | 8.390 | $7.751 \times 10^4$ (± 1.102%) | 1.050 (± 1.011%) |
| Anti-K48 hole | 7.241 | $1.799 \times 10^5$ (± 10.213%) | 1.064 (± 6.204%) |
|  | 8.308 | $7.747 \times 10^4$ (± 1.102%) | 1.004 (± 1.007%) |
| Anti-gD knob | 7.283 | $1.677 \times 10^5$ (± 03.568%) | 1.052 (± 7.137%) |
| Anti-K11/K48 bispecific | 7.835 | $1.795 \times 10^5$ (± 01.512%) | 1.008 (± 0.877%) |
| Anti-K11/gD bispecific | 7.637 | $1.810 \times 10^5$ (± 0.988%) | 1.010 (± 1.201%) |
| Anti-K48/gD bispecific | 7.575 | $1.646 \times 10^5$ (±1.242%) | 1.003 (± 0.546%) |

Antibodies were injected over an XBridge Protein BEH analytical SEC column coupled to a DAWN® HELEOS® II Multi-Angle Light Scatter detector for molar mass and polydispersity measurement. The elution time of individual peaks off the SEC column is given in minutes.

TABLE 3

Mass spectrometry analysis of half antibodies and assembled bispecifics.

| | Theoretical Mass (Da) | Experimental Mass (Da) | Mass Difference (Da) |
|---|---|---|---|
| Anti-K11 knob half antibody | 72,370.24 | 72,370.69 | +0.45 |
| Anti-K11 hole half antibody | 72,164.98 | 72,165.09 | +0.11 |
| Anti-K48 hole half antibody | 72,242.95 | 72,243.24 | +0.29 |
| Anti-gD knob half antibody | 73,458.16 | 73,458.17 | +0.01 |
| Anti-K11/K48 bispecific | 144,613.19 | 144,617.30 | +4.11 |
| Anti-K11 knob homodimer | 144,740.48 | N/O$^a$ | |
| Anti-K48 hole homodimer | 144,485.90 | N/O | |
| Anti-K11/gD bispecific | 145,623.14 | 145,626.85 | +3.71 |
| Anti-K11 hole homodimer | 144,329.96 | N/O | |
| Anti-gD knob homodimer | 146,916.32 | N/O | |
| Anti-K48/gD bispecific | 145,701.11 | 145,703.68 | +2.57 |
| Anti-K48 hole homodimer | 144,485.90 | N/O | |
| Anti-gD knob homodimer | 146,916.32 | N/O | |

Antibodies were deglycosylated with PNGaseF and analyzed by liquid chromatography-mass spectrometry (LC-MS). The theoretical masses are for the non-reduced, deglycosylated antibodies and assume complete removal of the carboxy-terminal lysine residue during mammalian cell expression. The mass difference is reported as the difference between the experimental mass and the theoretical mass. N/O$^a$, not observed.

Figure 2B:
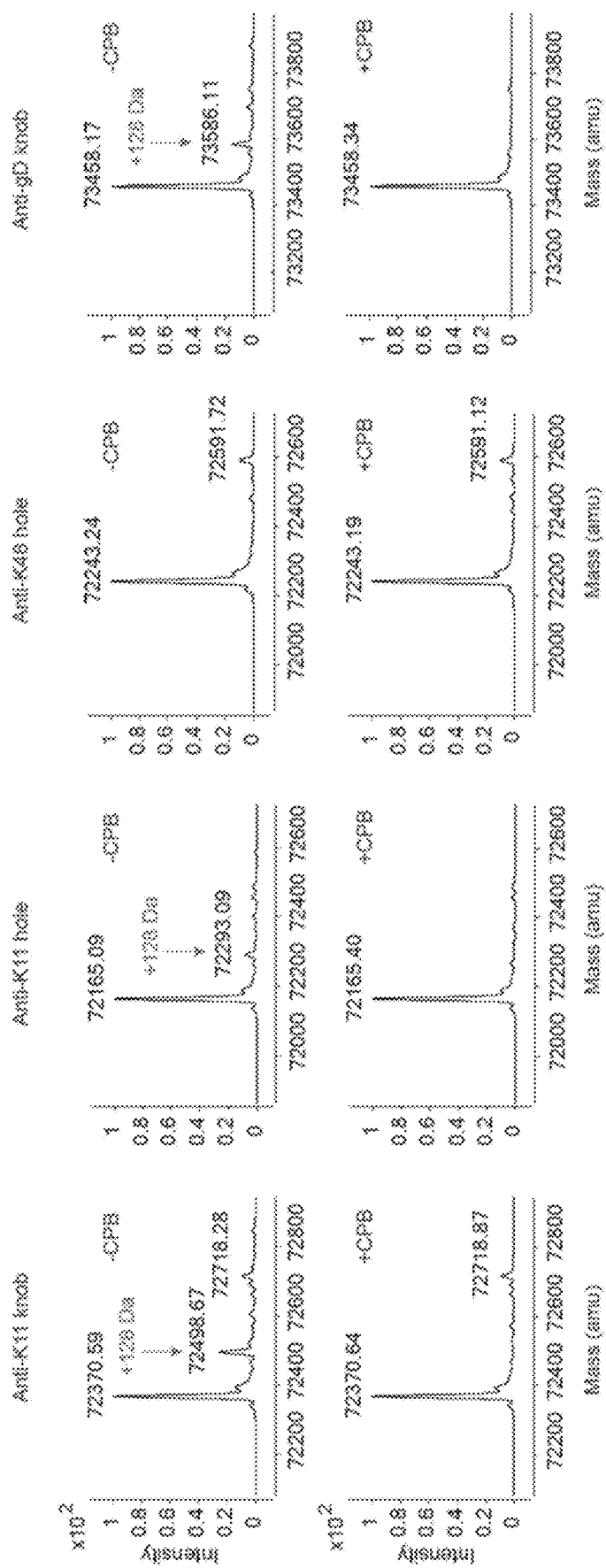

By SEC-MALS the anti-K48 hole antibody shows approximately 2000 homodimer and 80% monomer (FIG. 1c, Table 2). The proportions are less clear for the anti-K11 knob antibody as the homodimer and monomer co-elute on SEC, evidenced by a broad elution peak containing a lagging-edge shoulder that shows high polydispersity by MALS (FIG. 1c, Table 2). Both knob and hole homodimers are non-covalent in nature (i.e. the hinge disulfides are not formed) as they are disrupted in the reverse-phase chromatography step of LC-MS leading to detection of only monomers by MS (FIG. 2b, Table 3). This is consistent with the anti-parallel orientation of the knob/knob or hole/hole Fc domains seen in X-ray crystal structures of homodimers. See Elliott, J. M. et al. Antiparallel conformation of knob and hole aglycosylated half-antibody homodimers is mediated by a CH2-CH3 hydrophobic interaction. *J Mol Biol* 426, 1947-1957, doi:10.1016/j.jmb.2014.02.015 (2014).

Bispecific antibodies were assembled from half antibodies in vitro using annealing, reduction, and oxidation. The anti-K11/K48 bispecific antibody was assembled in vitro from the affinity purified anti-K11 knob and anti-K48 hole antibodies using a modified version of the previously described method of annealing, reduction, and oxidation (Shatz, W. et al. Knobs-into-holes antibody production in mammalian cell lines reveals that asymmetric afucosylation is sufficient for full antibody-dependent cellular cytotoxicity. *MAbs* 5, 872-881, doi:10.4161/mabs.26307 (2013).) (FIG. 1a). Briefly, the desired knob and hole half antibodies were mixed at a 1:1 mass ratio and the pH of the mixture was adjusted to 8.5 with 15% (v/v) of 800 mM arginine, pH 10.0. A 200-fold molar excess of reduced glutathione (Sigma Aldrich) in 800 mM arginine, pH 10.0 was added and the assembly reaction was incubated at room temperature for 72 hours with exposure to air to allow annealing of the knob and hole half antibodies and formation of the hinge disulfides. Anti-K11/gD and anti-K48/gD control bispecific antibodies were similarly assembled.

The resulting heterodimers were further purified using hydrophobic interaction (HIC) and cation-exchange (CEX) chromatography to remove any excess half antibodies and homodimers. The bispecific antibodies migrate as a ~150 kDa band on SDS-PAGE, elute as a sharp peak on analytical SEC, and are monodisperse with a molar mass consistent with that of a full antibody (FIG. 1b, 1c, 2a, Table 2).

C. Antibody Purification and Characterization

Assembled bispecific antibodies were purified by hydrophobic interaction chromatography (HIC). Briefly, the assembly reaction was conditioned with 3 volumes of buffer A (25 mM sodium phosphate, 1 M ammonium sulfate, pH 6.5) to a final concentration of 0.75 M ammonium sulfate. The assembly reaction was filtered, loaded onto a 5 μm, 7.8×75 mm ProPac HIC-10 column (Dionex), followed by washing with buffer A. A 0-100% buffer B (25 mM sodium phosphate, pH 6.5, 25% isopropanol) linear gradient over 40 column volumes (CVs) was performed to separate the bispecific antibody from any unreacted half antibodies or aggregated protein. Identity of the eluting peaks was monitored by SDS-PAGE and mass spectrometry (see below for method details).

The bispecific antibodies were further purified by cation-exchange chromatography (CEX). Briefly, the HIC pooled material was dialyzed into 20 mM sodium acetate, pH 5.0, loaded onto a 10 μm Mono S® 5/50 GL column (GE Healthcare), and washed with buffer A (20 mM sodium acetate, pH 5.0). A 0-100% buffer B (20 mM sodium acetate, pH 5.0, 1 M NaCl) linear gradient over 40 CVs was performed and the desired fractions pooled. The purified bispecific antibodies were formulated in 20 mM histidine acetate, 240 mM sucrose, 0.02% polysorbate 20 (TWEEN® 20), pH 5.5.

LC-MS was used to confirm the identity of the purified, annealed species (FIG. 1d, 2c, Table 3). To reduce heterogeneity the antibodies were deglycosylated with PNGaseF before analysis. The major species in the anti-K11/K48 assembly is indeed the bispecific with an observed mass of 144,617.30 Da that is within 4.11 Da of the theoretical mass (144,613.19 Da).

No anti-K48 hole homodimers with a theoretical mass of 144,485.90 Da were observed. An additional peak of 144,745.26 Da was seen which is close the theoretical mass of the anti-K11 knob homodimer (144,740.48 Da). This additional peak is 128 Da larger than the experimental mass of 144,617.30 Da observed for the anti-K11/K48 heterodimer. Recombinant antibodies purified from mammalian cells typically have the carboxy-terminal lysine residue on the heavy chain removed due to the activity of carboxypeptidases during expression. See Harris, R. J. Processing of C-terminal lysine and arginine residues of proteins isolated from mammalian cell culture. *J Chromatogr A* 705, 129-134 (1995); Harris, R. J., Wagner, K. L. & Spellman, M. W. Structural characterization of a recombinant CD4-IgG hybrid molecule. *Eur J Biochem* 194, 611-620 (1990).

The theoretical masses of the recombinant antibodies calculated here assume complete removal of the carboxy-terminal lysine. If removal of this lysine were incomplete resulting in a fraction of the bispecific with one heavy chain containing the additional residue we would also expect to see a peak at +128 Da, corresponding to the mass of a lysine residue. Further analysis of the half antibodies reveals that the anti-K11 knob, anti-K11 hole, and anti-gD knob all contain a minor fraction of antibody with the carboxy-terminal lysine still attached (FIG. 2b).

To demonstrate that the peak at 144,745.26 Da observed in the purified anti-K11/K48 bispecific is not due to contaminating anti-K11 knob homodimer, but rather a portion of the bispecific with one heavy chain carboxy-terminal lysine residue still attached, we treated the antibody with carboxypeptidase B (CPB). This results in the loss of the 144,745.26 Da peak, confirming that it is due to the presence of the carboxy-terminal lysine residue. Thus, the anti-K11/K48 bispecific antibody is highly pure and free of any homodimers.

D. Fluorescent Labeling of Antibodies

The anti-K11 monospecific antibody and the anti-K11/K48 bispecific antibody were labeled with Alexa Fluor® 488 and Alexa Fluor® 546, respectively, according to the manufacturer's instructions using Alexa Fluor® Protein Labeling Kits (ThermoFisher). Unreacted free dye was removed through extensive dialysis. Six and 8 moles of Alexa Fluor® 488 and Alexa Fluor® 546, respectively, per mole of antibody was conjugated.

Although the foregoing invention has been described in some detail by way of illustration and example for purposes of clarity of understanding, the descriptions and examples should not be construed as limiting the scope of the invention.

TABLE OF SEQUENCES

| SEQ ID NO | Description | Sequence |
|---|---|---|
| 1 | anti-K11 LC (with signal sequence underlined) | MGWSCIILFLVATATGVHSDIQMTQSPSSLSASVGDRVTITCRASQI VGTFVAWYQQKPGKAPKLLIYSASFLYSGVPSRFSGSGSGTDFTLTI SSLQPEDFATYYCQQSYTTPPTFGQGTKVEIKRTVAAPSVFIFPPSD EQLKSGTASVVCLLNNFYPREAKVQWKVDNALQSGNSQESVTEQDSK DSTYSLSSTLTLSKADYEKHKVYACEVTHQGLSSPVTKSFNRGEC |
| 2 | anti-K11 mature LC | DIQMTQSPSSLSASVGDRVTITCRASQIVGTFVAWYQQKPGKAPKLL IYSASFLYSGVPSRFSGSGSGTDFTLTISSLQPEDFATYYCQQSYTT PPTFGQGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 3 | anti-K11 knob HC (with signal sequence underlined) | MGWSCIILFLVATATGAYAEVQLVESGGGLVQPGGSLRLSCAASGFT FSNSYISWVRQAPGKGLEWVAAINPAGGYTYYADSVKGRFTISADTS KNTAYLQMNSLRAEDTAVYYCAREWYFGGYVMDYWGQGTLVTVSSAS TKGPSVFPLAPSSKSTSGGTAALGCLVKDYFPEPVTVSWNSGALTSG VHTFPAVLQSSGLYSLSSVVTVPSSSLGTQTYICNVNHKPSNTKVDK KVEPKSCDKTHTCPPCPAPELLGGPSVFLFPPKPKDTLMISRTPEVT CVVVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLWCLVKGFYPSDIAVEWESNGQPENNYKTTPPVLDSD GSFFLYSKLTVDKSRWQQGNVFSCSVMHEALHNHYTQKSLSLSPGK |
| 4 | anti-K11 mature knob HC | EVQLVESGGGLVQPGGSLRLSCAASGFTFSNSYISWVRQAPGKGLEW VAAINPAGGYTYYADSVKGRFTISADTSKNTAYLQMNSLRAEDTAVY YCAREWYFGGYVMDYWGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPAPIEKTISKAKGQPREPQVYTLPPSREEMTKNQVSLWCLVKGFY PSDIAVEWESNGQPENNYKTTPPVLDSDGSFFLYSKLTVDKSRWQQG NVFSCSVMHEALHNHYTQKSLSLSPGK |
| 5 | anti-K11 hole HC (with signal sequence underlined) | MGWSCIILFLVATATGAYAEVQLVESGGGLVQPGGSLRLSCAASGFT FSNSYISWVRQAPGKGLEWVAAINPAGGYTYYADSVKGRFTISADTS KNTAYLQMNSLRAEDTAVYYCAREWYFGGYVMDYWGQGTLVTVSSAS TKGPSVFPLAPSSKSTSGGTAALGCLVKDYFPEPVTVSWNSGALTSG VHTFPAVLQSSGLYSLSSVVTVPSSSLGTQTYICNVNHKPSNTKVDK KVEPKSCDKTHTCPPCPAPELLGGPSVFLFPPKPKDTLMISRTPEVT CVVVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLSCAVKGFYPSDIAVEWESNGQPENNYKTTPPVLDSD GSFFLVSKLTVDKSRWQQGNVFSCSVMHEALHNHYTQKSLSLSPGK |
| 6 | anti-K11 mature hole HC | EVQLVESGGGLVQPGGSLRLSCAASGFTFSNSYISWVRQAPGKGLEW VAAINPAGGYTYYADSVKGRFTISADTSKNTAYLQMNSLRAEDTAVY YCAREWYFGGYVMDYWGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPAPIEKTISKAKGQPREPQVYTLPPSREEMTKNQVSLSCAVKGFY PSDIAVEWESNGQPENNYKTTPPVLDSDGSFFLVSKLTVDKSRWQQG NVFSCSVMHEALHNHYTQKSLSLSPGK |
| 7 | anti-K11 LCVR (HVRs underlined) | DIQMTQSPSSLSASVGDRVTITCRASQIVGTFVAWYQQKPGKAPKLL IYSASFLYSGVPSRFSGSGSGTDFTLTISSLQPEDFATYYCQQSYTT PPTFGQGTKVEIK |

TABLE OF SEQUENCES

| SEQ ID NO | Description | Sequence |
|---|---|---|
| 8 | anti-K11 HCVR (HVRs underlined) | EVQLVESGGGLVQPGGSLRLSCAASGFTFSNSYISWVRQAPGKGLEW VAAINPAGGYTYYADSVKGRFTISADTSKNTAYLQMNSLRAEDTAVY YCAREWYFGGYVMDYWGQGTLVTSS |
| 9 | anti-K11 HVR-L1 | RASQIVGTFVA |
| 10 | anti-K11 HVR-L2 | SASFLYS |
| 11 | anti-K11 HVR-L3 | QQSYTTPPT |
| 12 | anti-K11 HVR-H1 | GFTFSNSYIS |
| 13 | anti-K11 HVR-H2 | AINPAGGYTYYADSVKG |
| 14 | anti-K11 HVR-H3 | AREWYFGGYVMDY |
| 15 | anti-K48 LC (with signal sequence underlined) | MGWSCIILFLVATATGVHSDIQMTQSPSSLSASVGDRVTITCRASQS VSSAVAWYQQKPGKAPKLLIYSASSLYSGVPSRFSGSRSGTDFTLTI SSLQPEDFATYYCQQSYSSLITFGQGTKVEIKRTVAAPSVFIFPPS DEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 16 | anti-K48 mature LC | DIQMTQSPSSLSASVGDRVTITCRASQSVSSAVAWYQQKPGKAPKLL IYSASSLYSGVPSRFSGSRSGTDFTLTISSLQPEDFATYYCQQSYS SLITFGQGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC |
| 17 | anti-K48 knob HC (with signal sequence underlined) | MGWSCIILFLVATATGAYAEVQLVESGGGLVQPGGSLRLSCAASGFN ISYSSMHWVRQAPGKGLEWVASIYSYYSYTSYADSVKGRFTISADTS KNTAYLQMNSLRAEDTAVYYCARSYSYHLGMDYWGQGTLVTVSSAST KGPSVFPLAPSSKSTSGGTAALGCLVKDYFPEPVTVSWNSGALTSGV HTFPAVLQSSGLYSLSSVVTVPSSSLGTQTYICNVNHKPSNTKVDKK VEPKSCDKTHTCPPCPAPELLGGPSVFLFPPKPKDTLMISRTPEVTC VVVDVSHEDPEVKFNWYVDGVEVHNAKTKPREEQYNSTYRVVSVLTV LHQDWLNGKEYKCKVSNKALPAPIEKTISKAKGQPREPQVYTLPPSR EEMTKNQVSLWCLVKGFYPSDIAVEWESNGQPENNYKTTPPVLDSDG SFFLYSKLTVDKSRWQQGNVFSCSVMHEALHNHYTQKSLSLSPGK |
| 18 | anti-K48 mature knob HC | EVQLVESGGGLVQPGGSLRLSCAASGFNISYSSMHWVRQAPGKGLEW VASIYSYYSYTSYADSVKGRFTISADTSKNTAYLQMNSLRAEDTAVY YCARSYSYHLGMDYWGQGTLVTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPIEKTISKAKGQPREPQVYTLPPSREEMTKNQVSLWCLVKGFYP SDIAVEWESNGQPENNYKTTPPVLDSDGSFFLYSKLTVDKSRWQQGN VFSCSVMHEALHNHYTQKSLSLSPGK |
| 19 | anti-K48 hole HC (with signal sequence underlined) | MGWSCIILFLVATATGAYAEVQLVESGGGLVQPGGSLRLSCAASGFN ISYSSMHWVRQAPGKGLEWVASIYSYYSYTSYADSVKGRFTISADTS KNTAYLQMNSLRAEDTAVYYCARSYSYHLGMDYWGQGTLVTVSSAST KGPSVFPLAPSSKSTSGGTAALGCLVKDYFPEPVTVSWNSGALTSGV HTFPAVLQSSGLYSLSSVVTVPSSSLGTQTYICNVNHKPSNTKVDKK VEPKSCDKTHTCPPCPAPELLGGPSVFLFPPKPKDTLMISRTPEVTC VVVDVSHEDPEVKFNWYVDGVEVHNAKTKPREEQYNSTYRVVSVLTV LHQDWLNGKEYKCKVSNKALPAPIEKTISKAKGQPREPQVYTLPPSR EEMTKNQVSLSCAVKGFYPSDIAVEWESNGQPENNYKTTPPVLDSDG SFFLVSKLTVDKSRWQQGNVFSCSVMHEALHNHYTQKSLSLSPGK |
| 20 | anti-K48 mature hole HC | EVQLVESGGGLVQPGGSLRLSCAASGFNISYSSMHWVRQAPGKGLEW VASIYSYYSYTSYADSVKGRFTISADTSKNTAYLQMNSLRAEDTAVY YCARSYSYHLGMDYWGQGTLVTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPIEKTISKAKGQPREPQVYTLPPSREEMTKNQVSLSCAVKGFYP SDIAVEWESNGQPENNYKTTPPVLDSDGSFFLVSKLTVDKSRWQQGN VFSCSVMHEALHNHYTQKSLSLSPGK |

TABLE OF SEQUENCES

| SEQ ID NO | Description | Sequence |
|---|---|---|
| 21 | anti-K48 LCVR (HVRs underlined) | DIQMTQSPSSLSASVGDRVTITC<u>RASQSVSSAVA</u>WYQQKPGKAPKLLIYS<u>ASSLYS</u>GVPSRFSGSRSGTDFTLTISSLQPEDFATYYC<u>QQSSYSSLIT</u>FGQGTKVEIK |
| 22 | anti-K48 HCVR (HVRs underlined) | EVQLVESGGGLVQPGGSLRLSCAASG<u>FNISYSSMH</u>WVRQAPGKGLEWVAS<u>IYSYYSYTSYADSVKG</u>RFTISADTSKNTAYLQMNSLRAEDTAVYYC<u>ARSYSYHLGMDY</u>WGQGTLVTVSS |
| 23 | anti-K48 HVR-L1 | RASQSVSSAVA |
| 24 | anti-K48 HVR-L2 | SASSLYS |
| 25 | anti-K48 HVR-L3 | QQSSYSSLIT |
| 26 | anti-K48 HVR-H1 | GFNISYSSMH |
| 27 | anti-K48 HVR-H2 | SIYSYYSYTSYADSVKG |
| 28 | anti-K48 HVR-H3 | ARSYSYHLGMDY |
| 29 | anti-K63 LC (with signal sequence underlined) | <u>MGWSCIILFLVATATGVHS</u>DIQMTQSPSSLSASVGDRVTITCRASQSVSSAVAWYQQKPGEAPKLLIYSARSLYSGVPSRFSGSRSGTDFTLTISSLQPEDFATYYCQQYSYSSLFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 30 | anti-K63 mature LC | DIQMTQSPSSLSASVGDRVTITCRASQSVSSAVAWYQQKPGEAPKLLIYSARSLYSGVPSRFSGSRSGTDFTLTISSLQPEDFATYYCQQYSYSSLFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 31 | anti-K63 knob HC (with signal sequence underlined) | <u>MGWSCIILFLVATATGAYA</u>EVQLVESGGGLVQPGGSLRLSCAASGFNVKTGLIHWVRQAPGKGLEWVAYITPYYGSTSYADSVKGRFTISADTSKNTAYLQMNSLRAEDTAVYYCAREYYRWYTAIDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 32 | anti-K63 mature knob HC | EVQLVESGGGLVQPGGSLRLSCAASGFNVKTGLIHWVRQAPGKGLEWVAYITPYYGSTSYADSVKGRFTISADTSKNTAYLQMNSLRAEDTAVYYCAREYYRWYTAIDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 33 | anti-K63 hole HC (with signal sequence underlined) | <u>MGWSCIILFLVATATGAYA</u>EVQLVESGGGLVQPGGSLRLSCAASGFNVKTGLIHWVRQAPGKGLEWVAYITPYYGSTSYADSVKGRFTISADTSKNTAYLQMNSLRAEDTAVYYCAREYYRWYTAIDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 34 | anti-K63 mature hole HC | EVQLVESGGGLVQPGGSLRLSCAASGFNVKTGLIHWVRQAPGKGLEWVAYITPYYGSTSYADSVKGRFTISADTSKNTAYLQMNSLRAEDTAVYYCAREYYRWYTAIDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLSCAVKGFY |

TABLE OF SEQUENCES

| SEQ ID NO | Description | Sequence |
|---|---|---|
| | | PSDIAVEWESNGQPENNYKTTPPVLDSDGSFFLVSKLTVDKSRWQQG<br>NVFSCSVMHEALHNHYTQKSLSLSPGK |
| 35 | anti-K63 LCVR (HVRs underlined) | DIQMTQSPSSLSASVGDRVTITC<u>RASQSVSSAVA</u>WYQQKPGEAPKLL<br>IY<u>SARSLYS</u>GVPSRFGSRSGTDFTLTISSLQPEDFATYYC<u>QQYSSY</u><br><u>SSLFT</u>FGQGTKVEIK |
| 36 | anti-K63 HCVR (HVRs underlined) | EVQLVESGGGLVQPGGSLRLSCAASG<u>FNVKTGLIH</u>WVRQAPGKGLEW<br>VAY<u>ITPYYGSTSYADSVKG</u>RFTISADTSKNTAYLQMNSLRAEDTAVY<br>YCAR<u>EYYRWYTAIDY</u>WGQGTLVTVSS |
| 37 | anti-K63 HVR-L1 | RASQSVSSAVA |
| 38 | anti-K63 HVR-L2 | SARSLYS |
| 39 | anti-K63 HVR-L3 | QQYSSYSSLFT |
| 40 | anti-K63 HVR-H1 | GFNVKTGLIH |
| 41 | anti-K63 HVR-H2 | YITPYYGSTSYADSVKG |
| 42 | anti-K63 HVR-H3 | AREYYRWYTAIDY |
| 43 | anti-linear LC (with signal sequence underlined) | <u>MGWSCIILFLVATATGVHS</u>DIQMTQSPSSLSASVGDRVTITCRASQD<br>VSTAVAWYQQKPGKAPKLLIYSAKFLYSGVPSRFSGSGSGTDFTLTI<br>SSLQPEDFATYYCQQSYTTPPTFGQGTKVEIKRTVAAPSVFIFPPSD<br>EQLKSGTASVVCLLNNFYPREAKVQWKVDNALQSGNSQESVTEQDSK<br>DSTYSLSSTLTLSKADYEKHKVYACEVTHQGLSSPVTKSFNRGEC |
| 44 | anti-linear mature LC | DIQMTQSPSSLSASVGDRVTITCRASQDVSTAVAWYQQKPGKAPKLL<br>IYSAKFLYSGVPSRFSGSGSGTDFTLTISSLQPEDFATYYCQQSYTT<br>PPTFGQGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC |
| 45 | anti-linear knob HC (with signal sequence underlined) | <u>MGWSCIILFLVATATGAYA</u>EVQLVESGGGLVQPGGSLRLSCAASGFT<br>FSNTYISWVRQAPGKGLEWVASITPSSGQTDYADSVKGRFTISADTS<br>KNTAYLQMNSLRAEDTAVYYCARTWLLRWVMDLWGQGTLVTVSSAST<br>KGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSR<br>EEMTKNQVSLWCLVKGFYPSDIAVEWESNGQPENNYKTTPPVLDSDG<br>SFFLYSKLTVDKSRWQQGNVFSCSVMHEALHNHYTQKSLSLSPGK |
| 46 | anti-linear mature knob HC | EVQLVESGGGLVQPGGSLRLSCAASGFTFSNTYISWVRQAPGKGLEW<br>VASTTPSSGQTDYADSVKGRFTISADTSKNTAYLQMNSLRAEDTAVY<br>YCARTWLLRWVMDLWGQGTLVTVSSASTKGPSVFPLAPSSKSTSGGT<br>AALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPE<br>LLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPAPIEKTISKAKGQPREPQVYTLPPSREEMTKNQVSLWCLVKGFYP<br>SDIAVEWESNGQPENNYKTTPPVLDSDGSFFLYSKLTVDKSRWQQGN<br>VFSCSVMHEALHNHYTQKSLSLSPGK |
| 47 | anti-linear hole HC (with signal sequence underlined) | <u>MGWSCIILFLVATATGAYA</u>EVQLVESGGGLVQPGGSLRLSCAASGFT<br>FSNTYISWVRQAPGKGLEWVASITPSSGQTDYADSVKGRFTISADTS<br>KNTAYLQMNSLRAEDTAVYYCARTWLLRWVMDLWGQGTLVTVSSAST<br>KGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSR<br>EEMTKNQVSLSCAVKGFYPSDIAVEWESNGQPENNYKTTPPVLDSDG<br>SFFLVSKLTVDKSRWQQGNVFSCSVMHEALHNHYTQKSLSLSPGK |
| 48 | anti-linear mature hole HC | EVQLVESGGGLVQPGGSLRLSCAASGFTFSNTYISWVRQAPGKGLEW<br>VASITPSSGQTDYADSVKGRFTISADTSKNTAYLQMNSLRAEDTAVY<br>YCARTWLLRWVMDLWGQGTLVTVSSASTKGPSVFPLAPSSKSTSGGT<br>AALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAPE |

TABLE OF SEQUENCES

| SEQ ID NO | Description | Sequence |
|---|---|---|
| | | LLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPIEKTISKAKGQPREPQVYTLPPSREEMTKNQVSLSCAVKGFYP SDIAVEWESNGQPENNYKTTPPVLDSDGSFFLVSKLTVDKSRWQQGN VFSCSVMHEALHNHYTQKSLSLSPGK |
| 49 | anti-linear LCVR (HVRs underlined) | DIQMTQSPSSLSASVGDRVTITC<u>RASQDVSTAVA</u>WYQQKPGKAPKLL IY<u>SAKFLYS</u>GVPSRFSGSGSGTDFTLTISSLQPEDFATYYC<u>QQSYTT PPT</u>FGQGTKVEIK |
| 50 | anti-linear HCVR (HVRs underlined) | EVQLVESGGGLVQPGGSLRLSCAASG<u>FTFSNTYIS</u>WVRQAPGKGLEW VAS<u>ITPSSGQTDYADSVKG</u>RFTISADTSKNTAYLQMNSLRAEDTAVY YCA<u>RTWLLRWVMDL</u>WGQGTLVTVSS |
| 51 | anti-linear HVR-L1 | RASQDVSTAVA |
| 52 | anti-linear HVR-L2 | SAKFLYS |
| 53 | anti-linear HVR-L3 | QQSYTTPPT |
| 54 | anti-linear HVR-H1 | GFTFSNTYIS |
| 55 | anti-linear HVR-H2 | SITPSSGQTDYADSVKG |
| 56 | anti-linear HVR-H3 | ARTWLLRWVMDL |

HC = heavy chain;
LC = light chain;
HCVR = heavy chain variable region;
LCVR = light chain variable region;
HVR = hypervariable region.

What is claimed is:

1. A nucleic acid encoding a multispecific antibody that binds a mixed-topology polyubiquitin comprising a first linkage and a second linkage, the antibody comprising a first VH/VL unit specific for the first linkage, and a second VH/VL unit specific for the second linkage, wherein the first linkage and the second linkage are a K11 linkage, and a K48 linkage, or a K48 linkage and a K11 linkage, respectively, wherein the multispecific-antibody comprises first and second half antibodies, wherein, a) one of the first and second half antibodies comprises
(i) HVR-L1 comprising the amino acid sequence of SEQ ID NO: 9,
(ii) HVR-L2 comprising the amino acid sequence of SEQ ID NO: 10,
(iii) HVR-L3 comprising the amino acid sequence of SEQ ID NO: 11,
(iv) HVR-H1 comprising the amino acid sequence of SEQ ID NO: 12,
(v) HVR-H2 comprising the amino acid sequence of SEQ ID NO: 13, and
(vi) HVR-H3 comprising the amino acid sequence of SEQ ID NO: 14, and
the other of the first and second half antibodies comprises
(i) HVR-L1 comprising the amino acid sequence of SEQ ID NO: 23,
(ii) HVR-L2 comprising the amino acid sequence of SEQ ID NO: 24,
(iii) HVR-L3 comprising the amino acid sequence of SEQ ID NO: 25,
(iv) HVR-H1 comprising the amino acid sequence of SEQ ID NO: 26,
(v) HVR-H2 comprising the amino acid sequence of SEQ ID NO: 27, and
(vi) HVR-H3 comprising the amino acid sequence of SEQ ID NO: 28;

b) one of the first and second half antibodies comprises
(i) HVR-L1 comprising the amino acid sequence of SEQ ID NO: 9,
(ii) HVR-L2 comprising the amino acid sequence of SEQ ID NO: 10,
(iii) HVR-L3 comprising the amino acid sequence of SEQ ID NO: 11,
(iv) HVR-H1 comprising the amino acid sequence of SEQ ID NO: 12,
(v) HVR-H2 comprising the amino acid sequence of SEQ ID NO: 13, and
(vi) HVR-H3 comprising the amino acid sequence of SEQ ID NO: 14, and
the other of the first and second half antibodies comprises
(i) HVR-L1 comprising the amino acid sequence of SEQ ID NO: 37,
(ii) HVR-L2 comprising the amino acid sequence of SEQ ID NO: 38,
(iii) HVR-L3 comprising the amino acid sequence of SEQ ID NO: 39,
(iv) HVR-H1 comprising the amino acid sequence of SEQ ID NO: 40,
(v) HVR-H2 comprising the amino acid sequence of SEQ ID NO: 41, and
(vi) HVR-H3 comprising the amino acid sequence of SEQ ID NO: 42;

c) one of the first and second half antibodies comprises
(i) HVR-L1 comprising the amino acid sequence of SEQ ID NO: 9,
(ii) HVR-L2 comprising the amino acid sequence of SEQ ID NO: 10,
(iii) HVR-L3 comprising the amino acid sequence of SEQ ID NO: 11,
(iv) HVR-H1 comprising the amino acid sequence of SEQ ID NO: 12,
(v) HVR-H2 comprising the amino acid sequence of SEQ ID NO: 13, and
(vi) HVR-H3 comprising the amino acid sequence of SEQ ID NO: 14, and
the other of the first and second half antibodies comprises
(i) HVR-L1 comprising the amino acid sequence of SEQ ID NO: 51,
(ii) HVR-L2 comprising the amino acid sequence of SEQ ID NO: 52,
(iii) HVR-L3 comprising the amino acid sequence of SEQ ID NO: 53,
(iv) HVR-H1 comprising the amino acid sequence of SEQ ID NO: 54,
(v) HVR-H2 comprising the amino acid sequence of SEQ ID NO: 55, and
(vi) HVR-H3 comprising the amino acid sequence of SEQ ID NO: 56;

d) one of the first and second half antibodies comprises
(i) HVR-L1 comprising the amino acid sequence of SEQ ID NO: 23,
(ii) HVR-L2 comprising the amino acid sequence of SEQ ID NO: 24,
(iii) HVR-L3 comprising the amino acid sequence of SEQ ID NO: 25,
(iv) HVR-H1 comprising the amino acid sequence of SEQ ID NO: 26,
(v) HVR-H2 comprising the amino acid sequence of SEQ ID NO: 27, and
(vi) HVR-H3 comprising the amino acid sequence of SEQ ID NO: 28, and
the other of the first and second half antibodies comprises
(i) HVR-L1 comprising the amino acid sequence of SEQ ID NO: 37,
(ii) HVR-L2 comprising the amino acid sequence of SEQ ID NO: 38,
(iii) HVR-L3 comprising the amino acid sequence of SEQ ID NO: 39,
(iv) HVR-H1 comprising the amino acid sequence of SEQ ID NO: 40,
(v) HVR-H2 comprising the amino acid sequence of SEQ ID NO: 41, and
(vi) HVR-H3 comprising the amino acid sequence of SEQ ID NO: 42;
e) one of the first and second half antibodies comprises
(i) HVR-L1 comprising the amino acid sequence of SEQ ID NO: 23,
(ii) HVR-L2 comprising the amino acid sequence of SEQ ID NO: 24,
(iii) HVR-L3 comprising the amino acid sequence of SEQ ID NO: 25,
(iv) HVR-H1 comprising the amino acid sequence of SEQ ID NO: 26,
(v) HVR-H2 comprising the amino acid sequence of SEQ ID NO: 27, and
(vi) HVR-H3 comprising the amino acid sequence of SEQ ID NO: 28, and
the other of the first and second half antibodies comprises
(i) HVR-L1 comprising the amino acid sequence of SEQ ID NO: 51,
(ii) HVR-L2 comprising the amino acid sequence of SEQ ID NO: 52,
(iii) HVR-L3 comprising the amino acid sequence of SEQ ID NO: 53,
(iv) HVR-H1 comprising the amino acid sequence of SEQ ID NO: 54,
(v) HVR-H2 comprising the amino acid sequence of SEQ ID NO: 55, and
(vi) HVR-H3 comprising the amino acid sequence of SEQ ID NO: 56; or
f) one of the first and second half antibodies comprises
(i) HVR-L1 comprising the amino acid sequence of SEQ ID NO: 37,
(ii) HVR-L2 comprising the amino acid sequence of SEQ ID NO: 38,
(iii) HVR-L3 comprising the amino acid sequence of SEQ ID NO: 39,
(iv) HVR-H1 comprising the amino acid sequence of SEQ ID NO: 40,
(v) HVR-H2 comprising the amino acid sequence of SEQ ID NO: 41, and
(vi) HVR-H3 comprising the amino acid sequence of SEQ ID NO: 42, and the other of the first and second half antibodies comprises
(i) HVR-L1 comprising the amino acid sequence of SEQ ID NO: 51,
(ii) HVR-L2 comprising the amino acid sequence of SEQ ID NO: 52,
(iii) HVR-L3 comprising the amino acid sequence of SEQ ID NO: 53,
(iv) HVR-H1 comprising the amino acid sequence of SEQ ID NO: 54,
(v) HVR-H2 comprising the amino acid sequence of SEQ ID NO: 55, and
(vi) HVR-H3 comprising the amino acid sequence of SEQ ID NO: 56.

2. The nucleic acid encoding a multispecific antibody of claim 1, wherein the multispecific antibody is: a knob-in-hole bispecific antibody; a bispecific antibody comprising a leucine zipper; a cross-linked pair of antibodies; an antibody Fc-heterodimeric molecule; a diabody; a triabody; a tetrabody; a single-chain Fv dimer; a trispecific antibody; an octopus antibody; or a dual acting FAb.

3. The nucleic acid encoding a multispecific antibody of claim 1, wherein the first linkage and the second linkage are: a K11 linkage and a K48 linkage.

4. The nucleic acid encoding a multispecific antibody of claim 1, wherein the multispecific antibody comprises first and second half antibodies, wherein the first half antibody comprises:
a) a VL sequence of SEQ ID NO: 7 and a VH sequence of SEQ ID NO: 8; or
b) a VL sequence of SEQ ID NO: 21 and a VH sequence of SEQ ID NO: 22.

5. The nucleic acid encoding a multispecific antibody of claim 1, wherein the multispecific antibody comprises first and second half antibodies, wherein the second half antibody comprises:
a) a VL sequence of SEQ ID NO: 7 and a VH sequence of SEQ ID NO: 8; or
b) a VL sequence of SEQ ID NO: 21 and a VH sequence of SEQ ID NO: 22;
wherein the VL and VH sequences of the second half antibody are not identical to the VL and VH sequences of the first half antibody.

6. The nucleic acid encoding a multispecific antibody of claim 1, wherein the multispecific antibody comprises first and second half antibodies, wherein:
one of the first and second half antibodies comprises a VL sequence of SEQ ID NO: 7 and a VH sequence of SEQ ID NO: 8;
and the other of the first and second half antibodies comprises a VL sequence of SEQ ID NO: 21 and a VH sequence of SEQ ID NO: 22.

7. The nucleic acid encoding a multispecific antibody of claim 1, wherein the multispecific antibody is a monoclonal antibody.

8. The nucleic acid encoding a multispecific antibody of claim 1, wherein the multispecific antibody is an IgG antibody.

9. The nucleic acid encoding a multispecific antibody of claim 1, wherein the bispecific antibody comprises first and second half antibodies, wherein the first half antibody comprises a first heavy chain constant region comprising a knob mutation and the second half antibody comprises a second heavy chain constant region comprising a hole mutation, or wherein the first half antibody comprises a first heavy chain constant region comprising a hole mutation and the second half antibody comprises a second heavy chain constant region comprising a knob mutation.

10. The nucleic acid encoding a multispecific antibody of claim 9, wherein the multispecific antibody is an IgG1 antibody and wherein the knob mutation comprises a T366W mutation.

11. The nucleic acid encoding a multispecific antibody of claim 1, wherein the multispecific antibody comprises first and second half antibodies, wherein the first half antibody comprises:
   a) a light chain sequence of SEQ ID NO: 2 and a heavy chain sequence of SEQ ID NO: 4; or
   b) a light chain sequence of SEQ ID NO: 16 and a heavy chain sequence of SEQ ID NO: 18;
   optionally wherein the multispecific antibody comprises one or more heavy chains and a C-terminal lysine is missing from the one or more heavy chains.

12. The nucleic acid encoding a multispecific antibody of claim 1, wherein the multispecific antibody comprises first and second half antibodies, wherein the first half antibody comprises:
   a) a light chain sequence of SEQ ID NO: 2 and a heavy chain sequence of SEQ ID NO: 6; or
   b) a light chain sequence of SEQ ID NO: 16 and a heavy chain sequence of SEQ ID NO: 20;
   optionally wherein the multispecific antibody comprises one or more heavy chains and a C-terminal lysine is missing from the one or more heavy chains.

13. The nucleic acid encoding a multispecific antibody of claim 1, wherein the multispecific antibody comprises first and second half antibodies, wherein:
   a) the first half antibody comprises a light chain sequence of SEQ ID NO: 2 and a heavy chain sequence of SEQ ID NO: 4,
   and the second half antibody comprises a light chain sequence of SEQ ID NO: 16 and a heavy chain sequence of SEQ ID NO: 20; or
   b) the first half antibody comprises a light chain sequence of SEQ ID NO: 2 and a heavy chain sequence of SEQ ID NO: 6,
   and the second half antibody comprises a light chain sequence of SEQ ID NO: 16 and a heavy chain sequence of SEQ ID NO: 18;
   optionally wherein the multispecific antibody comprises one or more heavy chains and a C-terminal lysine is missing from the one or more heavy chains.

14. A host cell comprising the nucleic acid of claim 1.

15. A method of producing an antibody or half antibody comprising culturing the host cell of claim 14 under conditions suitable for producing the antibody or half antibody, thereby producing the antibody or half antibody.

* * * * *

UNITED STATES PATENT AND TRADEMARK OFFICE
CERTIFICATE OF CORRECTION

| | |
|---|---|
| PATENT NO. | : 12,215,143 B2 |
| APPLICATION NO. | : 17/576344 |
| DATED | : February 4, 2025 |
| INVENTOR(S) | : Dixit et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 433 days.

Signed and Sealed this
Tenth Day of June, 2025

Coke Morgan Stewart
*Acting Director of the United States Patent and Trademark Office*